(12) United States Patent
Tocchini-Valentini et al.

(10) Patent No.: US 8,512,945 B2
(45) Date of Patent: Aug. 20, 2013

(54) METHOD OF RNA CLEAVAGE AND RECOMBINATION

(76) Inventors: Glauco P. Tocchini-Valentini, Rome (IT); Giancarlo Deidda, Rome (IT); Nicoletta Rossi, Rome (IT)

( * ) Notice: Subject to any disclaimer, the term of this patent is extended or adjusted under 35 U.S.C. 154(b) by 1073 days.

(21) Appl. No.: 10/821,777

(22) Filed: Apr. 9, 2004

(65) Prior Publication Data

US 2005/0043259 A1 Feb. 24, 2005

Related U.S. Application Data

(63) Continuation-in-part of application No. 10/296,574, filed as application No. PCT/IB01/01189 on May 30, 2001, now abandoned.

(60) Provisional application No. 60/208,432, filed on May 31, 2000, provisional application No. 60/462,624, filed on Apr. 14, 2003.

(51) Int. Cl.
*C12Q 1/68* (2006.01)
*C07H 21/02* (2006.01)
*A61K 48/00* (2006.01)

(52) U.S. Cl.
CPC .................................. *C12Q 1/6883* (2013.01)
USPC .......................... 435/6.1; 536/23.1; 514/44 R

(58) Field of Classification Search
USPC .............. 536/23.1, 24.5; 435/6, 6.1; 514/44
See application file for complete search history.

(56) References Cited

FOREIGN PATENT DOCUMENTS

WO  WO 01/09246 A2  12/2001
WO  WO 01/09246 A3  12/2001

OTHER PUBLICATIONS

Abelson et al., tRNA splicing, 1998, The Journal of Biological Chemistry, vol. 273, pp. 12685-12688.*
Reyes et al., A synthetic substrate for tRNA splicing, 1987, Analytical Chemistry, vol. 166, pp. 90-106.*
J.L. Diener and P.B. Moore, "Solution Structure of a Substrate for teh Archaeal Pre-tRNA Splicing Endonucleoses: The Bulge-Helix-Bulge Motif," Mol. Cell 1:883-894, 1998.
S. Fabbri, et al., "Conservation of Substrate Recognition Mechanisms by tRNA Splicing Endonucleases," Science 280:284-286, 1998.
P. Fruscoloni, et al., "Cleavage of Non-tRNA Substrates by Eurkaryal tRNA Splicing Endonucleases," EMBO Rep. 21(31):217-221, 2001.
H. Li, et al., "Crystal Structure and Evolution of a Transfer RNA Splicing Enzyme," Science 280:279-284, 1998.
M. Nashimoto, et al., "RNA Heptamers that Direct RNA Cleavage by Mammalian tRNA 3' Processing Endoribonuctease," Nuc. Acids Res. 26(11):2565-2571, 1998.
Fruscoloni P, et al., "Cleavage of non-tRNA substrates by eukaryal tRNA splicing endonucleases," EMBO Rep. 2:217-221 (2001).
Tocchini-Valentini G, et al., "Structure, function, and evolution of the tRNA endonucleases of Archaea: an example of subfunctionalization," PNAS, 102:8933-8938 (2005).
Tocchini-Valentini G, et al., "Coevolution of tRNA intron motifs and tRNA endonuclease architecture in Archaea," PNAS, 102:15418-15422 (2005).
Tocchini-Valentini G, et al., "The dawn of dominance by the mature domain in tRNA splicing," PNAS, 104:12300-12305 (2007).
Anderson A. et al., "Long-distance splicing", PNAS, 105(19):6793-6794, 2008.
Di Segni G. et al., "Cis- and trans-splicing of mRNAs mediated by tRNA sequences in eukaryotic cells", PNAS, 105 (19):6864-6889, 2008.
Di Segni G., et al., "A pre-tRNA carrying intron features typical of Archaea is spliced in yeast", RNA, 11:70-76, 2005.

* cited by examiner

*Primary Examiner* — Dana Shin
(74) *Attorney, Agent, or Firm* — Quarles & Brady LLP

(57) ABSTRACT

A method of cleaving a target RNA molecule is disclosed. In one embodiment the method comprises the step of exposing the target molecule to an eukaryotic tRNA splicing endonuclease, wherein the target molecule is in the bulge-helix-bulge conformation, wherein cleavage occurs within the bulge-helix-bulge and cleavage products are generated, and wherein the target molecule does not comprise a tRNA structure.

6 Claims, 21 Drawing Sheets

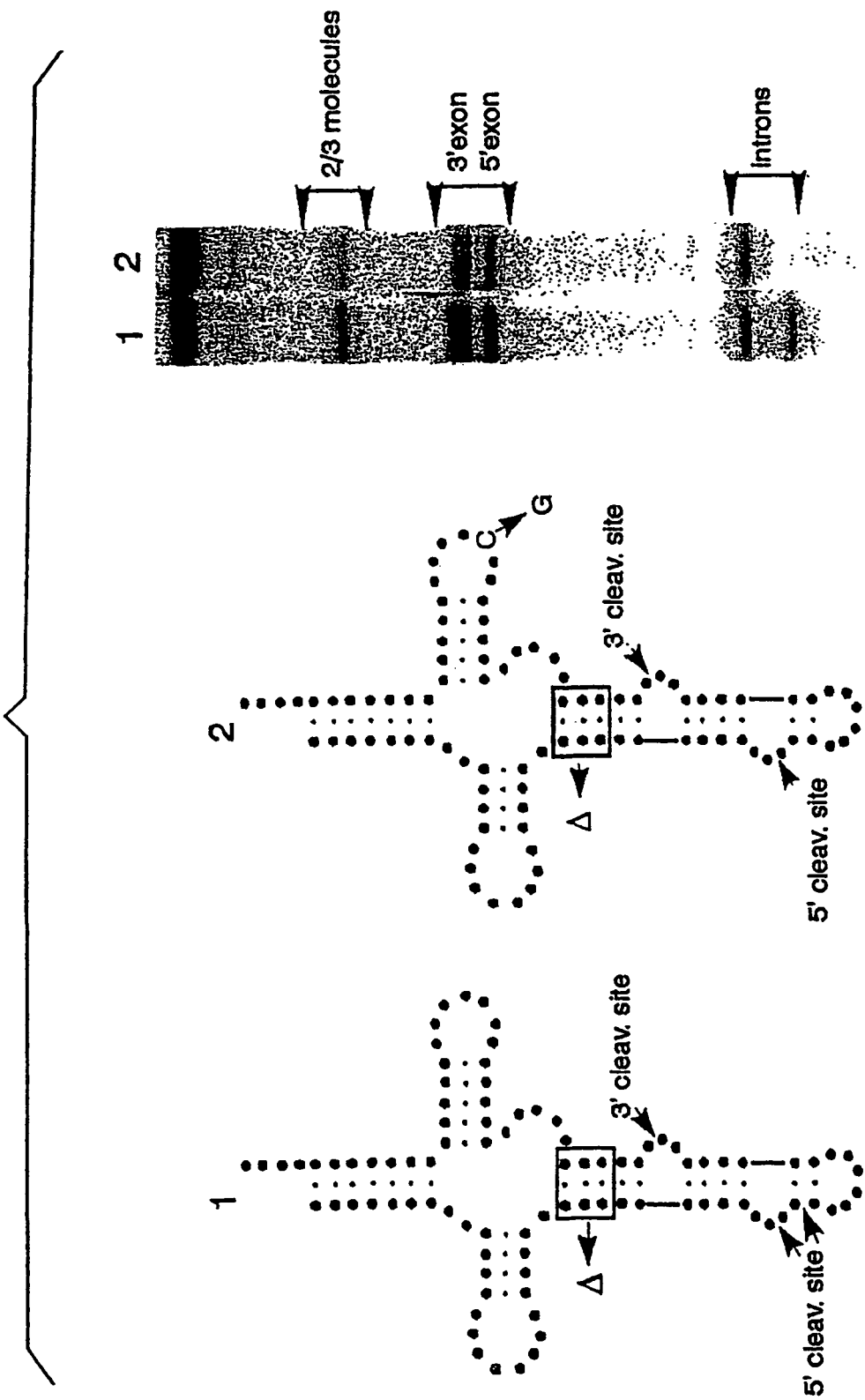

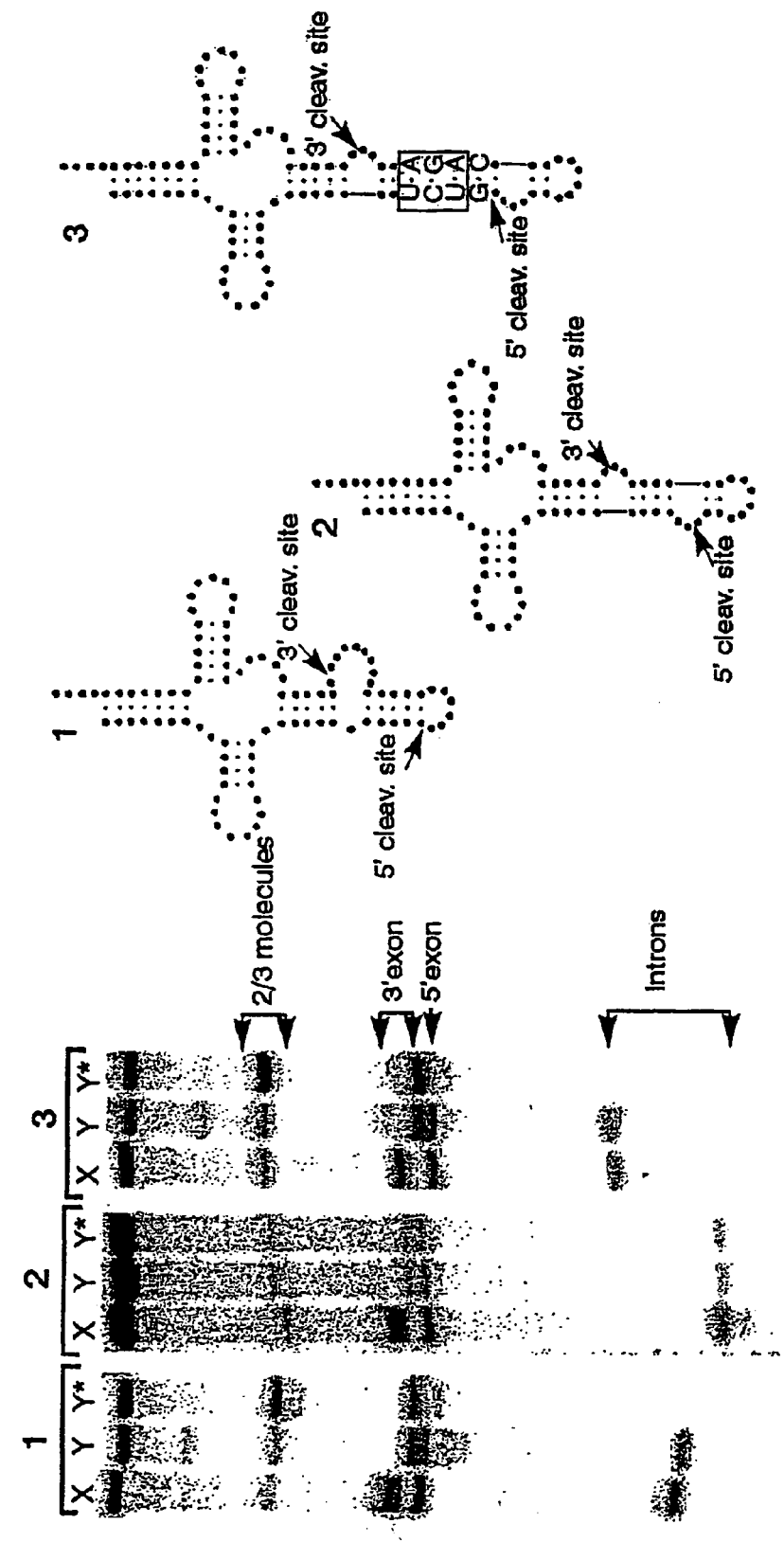

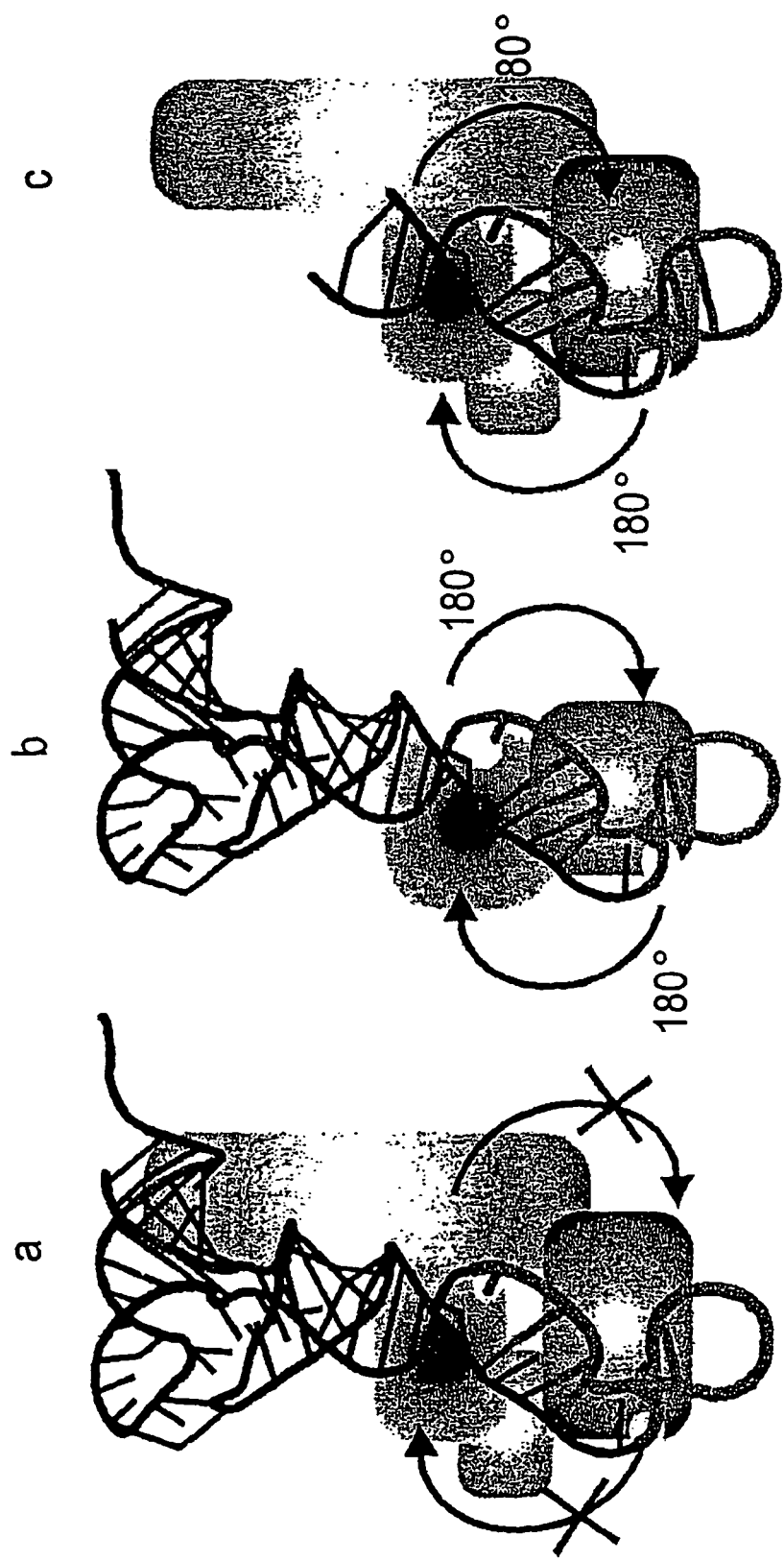

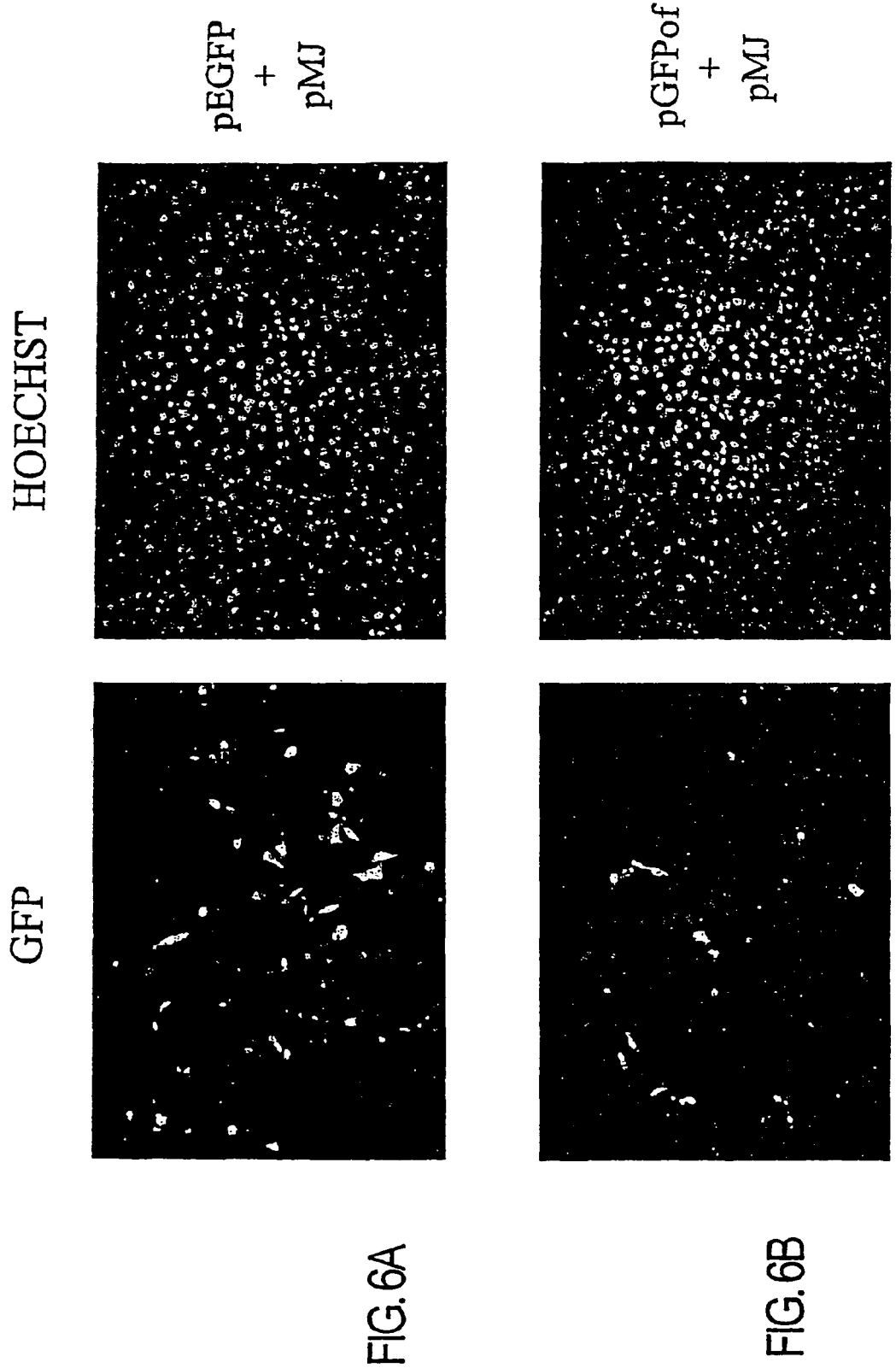

SPLICING ANALYSIS BY RT-PCR

Sequence analysis of GFP-BHB RT-PCR products pEGFP-WT             pMJ and pGFPof a)   b)

c)   d)

pOPTI-MJ and pGFPof    pMUT-MJ and pGFPof

L - Liver
SM - Skeletal Muscle
B - Brain
S - Spleen
K - Kidney
H - Heart

SEQUENCE LISTING

<160> NUMBER OF SEQ ID NOS: 85

<210> SEQ ID NO 1
<211> LENGTH: 80

```
<212> TYPE: DNA
<213> ORGANISM: Artificial
<220> FEATURE:
<223> OTHER INFORMATION: Synthetic oligonucleotide

<400> SEQUENCE: 1
gagctcaagc ttcgaattcc cggtcgtgac tccagaggct tacaccggag atatcacgac    60
cggttgtgag caagggcgag                                                80

<210> SEQ ID NO 2
<211> LENGTH: 65
<212> TYPE: DNA
<213> ORGANISM: Artificial
<220> FEATURE:
<223> OTHER INFORMATION: Synthetic oligonucleotide

<400> SEQUENCE: 2
atcacgagat ctccaccatg gactacaaag acgatgacga taaactcgag ctcaagcttc    60
gaatt                                                                65

<210> SEQ ID NO 3
<211> LENGTH: 30
<212> TYPE: DNA
<213> ORGANISM: Artificial
<220> FEATURE:
<223> OTHER INFORMATION: Synthetic oligonucleotide

<400> SEQUENCE: 3
tcgggatcct ctacaaatgt ggtatggctg                                     30

<210> SEQ ID NO 4
<211> LENGTH: 67
<212> TYPE: DNA
<213> ORGANISM: Artificial
<220> FEATURE:
<223> OTHER INFORMATION: Synthetic oligonucleotide

<400> SEQUENCE: 4
gcttcgaatt cccggtcgtg acttctccag aggcttacac cggagaagat atcacgaccg    60
gttgtga                                                              67

<210> SEQ ID NO 5
<211> LENGTH: 67
<212> TYPE: DNA
<213> ORGANISM: Artificial
<220> FEATURE:
<223> OTHER INFORMATION: Synthetic oligonucleotide

<400> SEQUENCE: 5
gcttcgaatt cccggtcgtg actccagagg taactgacta aaccggagat atcacgaccg    60
gttgtga                                                              67

<210> SEQ ID NO 6
<211> LENGTH: 67
<212> TYPE: DNA
<213> ORGANISM: Artificial
<220> FEATURE:
<223> OTHER INFORMATION: Synthetic oligonucleotide

<400> SEQUENCE: 6
ataagaatgc ggccgcccgg tcgtgatatc tccggtgtaa gcctctggag tcacgaccgg    60
ggacggg                                                              67
```

<210> SEQ ID NO 7
<211> LENGTH: 73
<212> TYPE: DNA
<213> ORGANISM: Artificial
<220> FEATURE:
<223> OTHER INFORMATION: Synthetic oligonucleotide

<400> SEQUENCE: 7
ataagaatgc ggccgcccgg tcgtgatatc ttctccggtg taagcctctg gagaagtcac    60
gaccggggac ggg    73

<210> SEQ ID NO 8
<211> LENGTH: 71
<212> TYPE: DNA
<213> ORGANISM: Artificial
<220> FEATURE:
<223> OTHER INFORMATION: Synthetic oligonucleotide

<400> SEQUENCE: 8
tcacgaccgg ggacgggggc ccagacggag ggcgagtcct tgtagcgcat ctacacattg    60
atcctagcag a    71

<210> SEQ ID NO 9
<211> LENGTH: 21
<212> TYPE: DNA
<213> ORGANISM: Artificial
<220> FEATURE:
<223> OTHER INFORMATION: Synthetic oligonucleotide

<400> SEQUENCE: 9
cgtcagatcc gctagcgcta c    21

<210> SEQ ID NO 10
<211> LENGTH: 21
<212> TYPE: DNA
<213> ORGANISM: Artificial
<220> FEATURE:
<223> OTHER INFORMATION: Synthetic oligonucleotide

<400> SEQUENCE: 10
cgtcgccgtc cagctcgacc a    21

<210> SEQ ID NO 11
<211> LENGTH: 21
<212> TYPE: DNA
<213> ORGANISM: Artificial
<220> FEATURE:
<223> OTHER INFORMATION: Synthetic oligonucleotide

<400> SEQUENCE: 11
tagatgcgct acaaggactc g    21

<210> SEQ ID NO 12
<211> LENGTH: 30
<212> TYPE: DNA
<213> ORGANISM: Artificial
<220> FEATURE:
<223> OTHER INFORMATION: Synthetic oligonucleotide

<400> SEQUENCE: 12
tcgggatcct ctacaaatgt ggtatggctg    30

<210> SEQ ID NO 13
<211> LENGTH: 62
<212> TYPE: DNA
<213> ORGANISM: Artificial

```
<220> FEATURE:
<223> OTHER INFORMATION: Synthetic oligonucleotide

<400> SEQUENCE: 13
atcacgagat ctccaccatg gactacaaag acgatgacga taaaatggtg agagataaaa    60
tg                                                                  62

<210> SEQ ID NO 14
<211> LENGTH: 39
<212> TYPE: DNA
<213> ORGANISM: Artificial
<220> FEATURE:
<223> OTHER INFORMATION: Synthetic oligonucleotide

<400> SEQUENCE: 14
ataagaatgc ggccgcggat ccttatggtt ttacatagg                           39

<210> SEQ ID NO 15
<211> LENGTH: 30
<212> TYPE: DNA
<213> ORGANISM: Artificial
<220> FEATURE:
<223> OTHER INFORMATION: Synthetic oligonucleotide

<400> SEQUENCE: 15
ataaagaatt ctctgtttat ttggttaagg                                     30

<210> SEQ ID NO 16
<211> LENGTH: 29
<212> TYPE: DNA
<213> ORGANISM: Artificial
<220> FEATURE:
<223> OTHER INFORMATION: Synthetic oligonucleotide

<400> SEQUENCE: 16
aacagagaat tctttatcat gttagctcc                                      29

<210> SEQ ID NO 17
<211> LENGTH: 30
<212> TYPE: DNA
<213> ORGANISM: Artificial
<220> FEATURE:
<223> OTHER INFORMATION: Synthetic oligonucleotide

<400> SEQUENCE: 17
tcagttcggc cgcaattact catagcaatc                                     30

<210> SEQ ID NO 18
<211> LENGTH: 29
<212> TYPE: DNA
<213> ORGANISM: Artificial
<220> FEATURE:
<223> OTHER INFORMATION: Synthetic oligonucleotide

<400> SEQUENCE: 18
gtaattgcgg ccgaactgag tgagcaacc                                      29

<210> SEQ ID NO 19
<211> LENGTH: 20
<212> TYPE: DNA
<213> ORGANISM: Artificial
<220> FEATURE:
<223> OTHER INFORMATION: Synthetic oligonucleotide

<400> SEQUENCE: 19
ggcaccaccc cggtgaacag                                                20
```

```
<210> SEQ ID NO 20
<211> LENGTH: 21
<212> TYPE: DNA
<213> ORGANISM: Artificial
<220> FEATURE:
<223> OTHER INFORMATION: Synthetic oligonucleotide

<400> SEQUENCE: 20
gtatggctga ttatgatcta g                                            21

<210> SEQ ID NO 21
<211> LENGTH: 49
<212> TYPE: DNA
<213> ORGANISM: Artificial
<220> FEATURE:
<223> OTHER INFORMATION: Synthetic oligonucleotide

<400> SEQUENCE: 21
ttgacgagtt cttctgaggg gatccattcc tagagctcgc tgatcagcc              49

<210> SEQ ID NO 22
<211> LENGTH: 37
<212> TYPE: DNA
<213> ORGANISM: Artificial
<220> FEATURE:
<223> OTHER INFORMATION: Synthetic oligonucleotide

<400> SEQUENCE: 22
aggacctcta gaagatctgc ctgctattgt cttccca                           37

<210> SEQ ID NO 23
<211> LENGTH: 21
<212> TYPE: DNA
<213> ORGANISM: Artificial
<220> FEATURE:
<223> OTHER INFORMATION: Synthetic oligonucleotide

<400> SEQUENCE: 23
ctctgactga ccgcgttact c                                            21

<210> SEQ ID NO 24
<211> LENGTH: 20
<212> TYPE: DNA
<213> ORGANISM: Artificial
<220> FEATURE:
<223> OTHER INFORMATION: Synthetic oligonucleotide

<400> SEQUENCE: 24
tgccgttctt gtcgaacacg                                              20

<210> SEQ ID NO 25
<211> LENGTH: 80
<212> TYPE: DNA
<213> ORGANISM: Artificial
<220> FEATURE:
<223> OTHER INFORMATION: Synthetic oligonucleotide

<400> SEQUENCE: 25
gagctcaagc ttcgaattcc cggtcgtgac tccagaggct tacaccggag atatcacgac  60
cggttgtgag caagggcgag                                              80

<210> SEQ ID NO 26
<211> LENGTH: 65
<212> TYPE: DNA
<213> ORGANISM: Artificial
```

```
<220> FEATURE:
<223> OTHER INFORMATION: Synthetic oligonucleotide

<400> SEQUENCE: 26
atcacgagat ctccaccatg gactacaaag acgatgacga taaactcgag ctcaagcttc      60
gaatt                                                                  65

<210> SEQ ID NO 27
<211> LENGTH: 30
<212> TYPE: DNA
<213> ORGANISM: Artificial
<220> FEATURE:
<223> OTHER INFORMATION: Synthetic oligonucleotide

<400> SEQUENCE: 27
tcgggatcct ctacaaatgt ggtatggctg                                       30

<210> SEQ ID NO 28
<211> LENGTH: 67
<212> TYPE: DNA
<213> ORGANISM: Artificial
<220> FEATURE:
<223> OTHER INFORMATION: Synthetic oligonucleotide

<400> SEQUENCE: 28
gcttcgaatt cccggtcgtg acttctccag aggcttacac cggagaagat atcacgaccg      60
gttgtga                                                                67

<210> SEQ ID NO 29
<211> LENGTH: 67
<212> TYPE: DNA
<213> ORGANISM: Artificial
<220> FEATURE:
<223> OTHER INFORMATION: Synthetic oligonucleotide

<400> SEQUENCE: 29
gcttcgaatt cccggtcgtg actccagagg taactgacta aaccggagat atcacgaccg      60
gttgtga                                                                67

<210> SEQ ID NO 30
<211> LENGTH: 67
<212> TYPE: DNA
<213> ORGANISM: Artificial
<220> FEATURE:
<223> OTHER INFORMATION: Synthetic oligonucleotide

<400> SEQUENCE: 30
ataagaatgc ggccgcccgg tcgtgatatc tccggtgtaa gcctctggag tcacgaccgg      60
ggacggg                                                                67

<210> SEQ ID NO 31
<211> LENGTH: 73
<212> TYPE: DNA
<213> ORGANISM: Artificial
<220> FEATURE:
<223> OTHER INFORMATION: Synthetic oligonucleotide

<400> SEQUENCE: 31
ataagaatgc ggccgcccgg tcgtgatatc ttctccggtg taagcctctg gagaagtcac      60
gaccggggac ggg                                                         73

<210> SEQ ID NO 32
<211> LENGTH: 71
```

```
<212> TYPE: DNA
<213> ORGANISM: Artificial
<220> FEATURE:
<223> OTHER INFORMATION: Synthetic oligonucleotide

<400> SEQUENCE: 32
tcacgaccgg ggacgggggc ccagacggag ggcgagtcct tgtagcgcat ctacacattg    60
atcctagcag a                                                        71

<210> SEQ ID NO 33
<211> LENGTH: 21
<212> TYPE: DNA
<213> ORGANISM: Artificial
<220> FEATURE:
<223> OTHER INFORMATION: Synthetic oligonucleotide

<400> SEQUENCE: 33
cgtcagatcc gctagcgcta c                                             21

<210> SEQ ID NO 34
<211> LENGTH: 21
<212> TYPE: DNA
<213> ORGANISM: Artificial
<220> FEATURE:
<223> OTHER INFORMATION: Synthetic oligonucleotide

<400> SEQUENCE: 34
cgtcgccgtc cagctcgacc a                                             21

<210> SEQ ID NO 35
<211> LENGTH: 21
<212> TYPE: DNA
<213> ORGANISM: Artificial
<220> FEATURE:
<223> OTHER INFORMATION: Synthetic oligonucleotide

<400> SEQUENCE: 35
tagatgcgct acaaggactc g                                             21

<210> SEQ ID NO 36
<211> LENGTH: 62
<212> TYPE: DNA
<213> ORGANISM: Artificial
<220> FEATURE:
<223> OTHER INFORMATION: Synthetic oligonucleotide

<400> SEQUENCE: 36
atcacgagat ctccaccatg gactacaaag acgatgacga taaaatggtg agagataaaa    60
tg                                                                  62

<210> SEQ ID NO 37
<211> LENGTH: 39
<212> TYPE: DNA
<213> ORGANISM: Artificial
<220> FEATURE:
<223> OTHER INFORMATION: Synthetic oligonucleotide

<400> SEQUENCE: 37
ataagaatgc ggccgcggat ccttatggtt ttacatagg                           39

<210> SEQ ID NO 38
<211> LENGTH: 30
<212> TYPE: DNA
<213> ORGANISM: Artificial
<220> FEATURE:
<223> OTHER INFORMATION: Synthetic oligonucleotide
```

```
<400> SEQUENCE: 38
ataaagaatt ctctgtttat ttggttaagg                                      30

<210> SEQ ID NO 39
<211> LENGTH: 29
<212> TYPE: DNA
<213> ORGANISM: Artificial
<220> FEATURE:
<223> OTHER INFORMATION: Synthetic oligonucleotide

<400> SEQUENCE: 39
aacagagaat tctttatcat gttagctcc                                       29

<210> SEQ ID NO 40
<211> LENGTH: 30
<212> TYPE: DNA
<213> ORGANISM: Artificial
<220> FEATURE:
<223> OTHER INFORMATION: Synthetic oligonucleotide

<400> SEQUENCE: 40
tcagttcggc cgcaattact catagcaatc                                      30

<210> SEQ ID NO 41
<211> LENGTH: 29
<212> TYPE: DNA
<213> ORGANISM: Artificial
<220> FEATURE:
<223> OTHER INFORMATION: Synthetic oligonucleotide

<400> SEQUENCE: 41
gtaattgcgg ccgaactgag tgagcaacc                                       29

<210> SEQ ID NO 42
<211> LENGTH: 20
<212> TYPE: DNA
<213> ORGANISM: Artificial
<220> FEATURE:
<223> OTHER INFORMATION: Synthetic oligonucleotide

<400> SEQUENCE: 42
ggcaccaccc cggtgaacag                                                 20

<210> SEQ ID NO 43
<211> LENGTH: 21
<212> TYPE: DNA
<213> ORGANISM: Artificial
<220> FEATURE:
<223> OTHER INFORMATION: Synthetic oligonucleotide

<400> SEQUENCE: 43
gtatggctga ttatgatcta g                                               21

<210> SEQ ID NO 44
<211> LENGTH: 79
<212> TYPE: DNA
<213> ORGANISM: Artificial
<220> FEATURE:
<223> OTHER INFORMATION: Synthetic oligonucleotide

<400> SEQUENCE: 44
gactcagatc tccaccatgg actacaaaga cgatgacgat aaagccggca gagataaaat     60
gggcaagaag atcaccggt                                                  79
```

```
<210> SEQ ID NO 45
<211> LENGTH: 81
<212> TYPE: DNA
<213> ORGANISM: Artificial
<220> FEATURE:
<223> OTHER INFORMATION: Synthetic oligonucleotide

<400> SEQUENCE: 45
ggcgctcagc ttgctgatgc cgttcttgtc gaacacgatc actctgtcgc cgtccagcag      60
accggtgatc ttcttgccca t                                                81

<210> SEQ ID NO 46
<211> LENGTH: 81
<212> TYPE: DNA
<213> ORGANISM: Artificial
<220> FEATURE:
<223> OTHER INFORMATION: Synthetic oligonucleotide

<400> SEQUENCE: 46
ggcatcagca agctgagcgc caggcactat ggcaatgtgg aaggcaattt cctgagcctg      60
agcctggtgg aagccctgta c                                                81

<210> SEQ ID NO 47
<211> LENGTH: 81
<212> TYPE: DNA
<213> ORGANISM: Artificial
<220> FEATURE:
<223> OTHER INFORMATION: Synthetic oligonucleotide

<400> SEQUENCE: 47
ttcgaagctc aggggcttgt tgtccttata cttcacctcc agccagccca ggttgatcag      60
gtacagggct ccaccaggc t                                                 81

<210> SEQ ID NO 48
<211> LENGTH: 81
<212> TYPE: DNA
<213> ORGANISM: Artificial
<220> FEATURE:
<223> OTHER INFORMATION: Synthetic oligonucleotide

<400> SEQUENCE: 48
aacaagcccc tgagcttcga agagctgtat gaatatgcca ggaacgtgga ggaaagactg      60
tgtctgaagt acctggtgta t                                                81

<210> SEQ ID NO 49
<211> LENGTH: 81
<212> TYPE: DNA
<213> ORGANISM: Artificial
<220> FEATURE:
<223> OTHER INFORMATION: Synthetic oligonucleotide

<400> SEQUENCE: 49
gaagtcggcg ccatacttca ggccggtctt cacgatatag ccctggtcc tcaggtcctt       60 ataccagg tacttcagac a                                                  81

<210> SEQ ID NO 50
<211> LENGTH: 81
<212> TYPE: DNA
<213> ORGANISM: Artificial
<220> FEATURE:
<223> OTHER INFORMATION: Synthetic oligonucleotide

<400> SEQUENCE: 50
ctgaagtatg gcgccgactt cagactgtac gaaaggggcg ccaacatcga caaggagcac      60
```

```
agcgtgtatc tggtgaaggt g                                              81

<210> SEQ ID NO 51
<211> LENGTH: 81
<212> TYPE: DNA
<213> ORGANISM: Artificial
<220> FEATURE:
<223> OTHER INFORMATION: Synthetic oligonucleotide

<400> SEQUENCE: 51
gtgggccact ctcacgaagc cggtcagctc gctcagcagg aagctgctgt cttcagggaa    60
caccttcacc agatacacgc t                                              81

<210> SEQ ID NO 52
<211> LENGTH: 81
<212> TYPE: DNA
<213> ORGANISM: Artificial
<220> FEATURE:
<223> OTHER INFORMATION: Synthetic oligonucleotide

<400> SEQUENCE: 52
ggcttcgtga gagtggccca cagcgtgaga aagaagctgc tgatcgccat cgtggacgcc    60
gacggcgaca tcgtgtatta c                                              81

<210> SEQ ID NO 53
<211> LENGTH: 86
<212> TYPE: DNA
<213> ORGANISM: Artificial
<220> FEATURE:
<223> OTHER INFORMATION: Synthetic oligonucleotide

<400> SEQUENCE: 53
cctctacaaa tgtggtatgg ctgctacgcg gccgcggatc cttaaggctt cacataggtc    60
atattgtaat acacgatgtc gccgtc                                         86

<210> SEQ ID NO 54
<211> LENGTH: 30
<212> TYPE: DNA
<213> ORGANISM: Artificial
<220> FEATURE:
<223> OTHER INFORMATION: Synthetic oligonucleotide

<400> SEQUENCE: 54
atcgacaagg agttcagcgt gtatctggtg                                     30

<210> SEQ ID NO 55
<211> LENGTH: 30
<212> TYPE: DNA
<213> ORGANISM: Artificial
<220> FEATURE:
<223> OTHER INFORMATION: Synthetic oligonucleotide

<400> SEQUENCE: 55
cagatacacg ctgaactcct tgtcgatgtt                                     30

<210> SEQ ID NO 56
<211> LENGTH: 36
<212> TYPE: DNA
<213> ORGANISM: Artificial
<220> FEATURE:
<223> OTHER INFORMATION: Synthetic oligonucleotide

<400> SEQUENCE: 56
gcccacagcg tgagacctca gctgctgatc gccatc                              36
```

```
<210> SEQ ID NO 57
<211> LENGTH: 36
<212> TYPE: DNA
<213> ORGANISM: Artificial
<220> FEATURE:
<223> OTHER INFORMATION: Synthetic oligonucleotide

<400> SEQUENCE: 57
gatggcgatc agcagctgag gtctcacgct gtgggc                              36

<210> SEQ ID NO 58
<211> LENGTH: 29
<212> TYPE: DNA
<213> ORGANISM: Artificial
<220> FEATURE:
<223> OTHER INFORMATION: Synthetic oligonucleotide

<400> SEQUENCE: 58
tagggaagct tcgtcagatc cgctagcgc                                     29

<210> SEQ ID NO 59
<211> LENGTH: 37
<212> TYPE: DNA
<213> ORGANISM: Artificial
<220> FEATURE:
<223> OTHER INFORMATION: Synthetic oligonucleotide

<400> SEQUENCE: 59
agaatggcgc cgggcctttc tttatgtttt tggcgtc                            37

<210> SEQ ID NO 60
<211> LENGTH: 91
<212> TYPE: DNA
<213> ORGANISM: Artificial
<220> FEATURE:
<223> OTHER INFORMATION: Synthetic oligonucleotide

<400> SEQUENCE: 60
cgtcagatcc gctagcgcta ccggactcag atcaattcgc tgactagccc ggagatatcc   60
tggaccggtt gaagacgcca aaaacataaa g                                  91

<210> SEQ ID NO 61
<211> LENGTH: 58
<212> TYPE: DNA
<213> ORGANISM: Artificial
<220> FEATURE:
<223> OTHER INFORMATION: Synthetic oligonucleotide

<400> SEQUENCE: 61
gatctggatc caccatggtc cggtccagga ctccagaggg ctagtcactc gagatcta     58

<210> SEQ ID NO 62
<211> LENGTH: 58
<212> TYPE: DNA
<213> ORGANISM: Artificial
<220> FEATURE:
<223> OTHER INFORMATION: Synthetic oligonucleotide

<400> SEQUENCE: 62
tagatctcga gtgactagcc ctctggagtc ctggaccgga ccatggtgga tccagatc     58

<210> SEQ ID NO 63
<211> LENGTH: 58
<212> TYPE: DNA
<213> ORGANISM: Artificial
```

```
<220> FEATURE:
<223> OTHER INFORMATION: Synthetic oligonucleotide

<400> SEQUENCE: 63
gatctggatc caccatggtc cggtccagga tatctccggg ctagtcactc gagatcta        58

<210> SEQ ID NO 64
<211> LENGTH: 58
<212> TYPE: DNA
<213> ORGANISM: Artificial
<220> FEATURE:
<223> OTHER INFORMATION: Synthetic oligonucleotide

<400> SEQUENCE: 64
tagatctcga gtgactagcc cggagatatc ctggaccgga ccatggtgga tccagatc        58

<210> SEQ ID NO 65
<211> LENGTH: 22
<212> TYPE: DNA
<213> ORGANISM: Artificial
<220> FEATURE:
<223> OTHER INFORMATION: Synthetic oligonucleotide

<400> SEQUENCE: 65
cccactgctt actggcttat cg                                               22

<210> SEQ ID NO 66
<211> LENGTH: 23
<212> TYPE: DNA
<213> ORGANISM: Artificial
<220> FEATURE:
<223> OTHER INFORMATION: Synthetic oligonucleotide

<400> SEQUENCE: 66
cccatactgt tgagcaattc acg                                              23

<210> SEQ ID NO 67
<211> LENGTH: 21
<212> TYPE: DNA
<213> ORGANISM: Artificial
<220> FEATURE:
<223> OTHER INFORMATION: Synthetic oligonucleotide

<400> SEQUENCE: 67
tgagctattc cagaagtagt g                                                21

<210> SEQ ID NO 68
<211> LENGTH: 22
<212> TYPE: DNA
<213> ORGANISM: Artificial
<220> FEATURE:
<223> OTHER INFORMATION: Synthetic oligonucleotide

<400> SEQUENCE: 68
gggagtggca ccttccaggg tc                                               22

<210> SEQ ID NO 69
<211> LENGTH: 38
<212> TYPE: DNA
<213> ORGANISM: Artificial
<220> FEATURE:
<223> OTHER INFORMATION: Synthetic oligonucleotide

<400> SEQUENCE: 69
gatatcacga ccggtttcgt ttactttgac caacaaga                              38
```

```
<210> SEQ ID NO 70
<211> LENGTH: 21
<212> TYPE: DNA
<213> ORGANISM: Artificial
<220> FEATURE:
<223> OTHER INFORMATION: Synthetic oligonucleotide

<400> SEQUENCE: 70
ttcaggctgc gcaactgttg g                                                   21

<210> SEQ ID NO 71
<211> LENGTH: 38
<212> TYPE: DNA
<213> ORGANISM: Artificial
<220> FEATURE:
<223> OTHER INFORMATION: Synthetic oligonucleotide

<400> SEQUENCE: 71
tcttgttggt caaagtaaac gaaaccggtc gtgatatc                                 38

<210> SEQ ID NO 72
<211> LENGTH: 93
<212> TYPE: RNA
<213> ORGANISM: Artificial
<220> FEATURE:
<223> OTHER INFORMATION: Synthetic RNA

<400> SEQUENCE: 72
gcggauuuag cucaguuggg agagcgccag acuccagagg cuuacaccgg agauaucugg         60
agguccugug uucgauccac agaauucgca cca                                     93

<210> SEQ ID NO 73
<211> LENGTH: 44
<212> TYPE: RNA
<213> ORGANISM: Artificial
<220> FEATURE:
<223> OTHER INFORMATION: Synthetic RNA

<400> SEQUENCE: 73 ccgucguga cuccagaggc uuacaccgga gauaucacga ccgg                           44

<210> SEQ ID NO 74
<211> LENGTH: 50
<212> TYPE: RNA
<213> ORGANISM: Artificial
<220> FEATURE:
<223> OTHER INFORMATION: Synthetic RNA

<400> SEQUENCE: 74 ccgucguga cuucuccaga ggcuuacacc ggagaagaua ucacgaccgg                     50

<210> SEQ ID NO 75
<211> LENGTH: 50
<212> TYPE: RNA
<213> ORGANISM: Artificial
<220> FEATURE:
<223> OTHER INFORMATION: Synthetic RNA

<400> SEQUENCE: 75 ccgucguga cuccagaggu aacugacuaa accggagaua ucacgaccgg                     50

<210> SEQ ID NO 76
<211> LENGTH: 72
<212> TYPE: DNA
<213> ORGANISM: Artificial
<220> FEATURE:
<223> OTHER INFORMATION: PCR product
```

```
<400> SEQUENCE: 76
atgacgataa actcgagctc aagcttcgaa ttcccggtcg tgactccaga tcacgaccgg    60
ttgtgagcaa gg                                                       72

<210> SEQ ID NO 77
<211> LENGTH: 28
<212> TYPE: DNA
<213> ORGANISM: Artificial
<220> FEATURE:
<223> OTHER INFORMATION: PCR product

<400> SEQUENCE: 77
gactccagag gcttacaccg gagatatc                                      28

<210> SEQ ID NO 78
<211> LENGTH: 89
<212> TYPE: DNA
<213> ORGANISM: Artificial
<220> FEATURE:
<223> OTHER INFORMATION: PCR product

<400> SEQUENCE: 78
atgacgataa actcgagctc aagcttcgaa ttcccggtcg tgactccaga ggcttacacc    60
ggagatatca cgaccggttg tgagcaagg                                     89

<210> SEQ ID NO 79
<211> LENGTH: 46
<212> TYPE: DNA
<213> ORGANISM: Artificial
<220> FEATURE:
<223> OTHER INFORMATION: PCR product

<400> SEQUENCE: 79
tccgtctggg cccccgtccc cggtcgtgac tccagatcac gaccgg                  46

<210> SEQ ID NO 80
<211> LENGTH: 28
<212> TYPE: DNA
<213> ORGANISM: Artificial
<220> FEATURE:
<223> OTHER INFORMATION: PCR product

<400> SEQUENCE: 80
gactccagag gcttacaccg gagatatc                                      28

<210> SEQ ID NO 81
<211> LENGTH: 63
<212> TYPE: DNA
<213> ORGANISM: Artificial
<220> FEATURE:
<223> OTHER INFORMATION: PCR product

<400> SEQUENCE: 81
tccgtctggg cccccgtccc cggtcgtgac tccagaggct tacaccggag atatcacgac    60
cgg                                                                 63

<210> SEQ ID NO 82
<211> LENGTH: 28
<212> TYPE: RNA
<213> ORGANISM: Artificial
<220> FEATURE:
<223> OTHER INFORMATION: Synthetic RNA

<400> SEQUENCE: 82
```

```
ccgguccagg acuccagagg gcuaguca                                      28

<210> SEQ ID NO 83
<211> LENGTH: 28
<212> TYPE: RNA
<213> ORGANISM: Artificial
<220> FEATURE:
<223> OTHER INFORMATION: Synthetic RNA

<400> SEQUENCE: 83
ccgguccagg auaucuccgg gcuaguca                                      28

<210> SEQ ID NO 84
<211> LENGTH: 28
<212> TYPE: RNA
<213> ORGANISM: Artificial
<220> FEATURE:
<223> OTHER INFORMATION: Synthetic RNA

<400> SEQUENCE: 84
ugacuagccc ggagauaucc uggaccgg                                      28

<210> SEQ ID NO 85
<211> LENGTH: 64
<212> TYPE: RNA
<213> ORGANISM: Artificial
<220> FEATURE:
<223> OTHER INFORMATION: Synthetic tRNA nuclease substrate

<400> SEQUENCE: 85
cuuacgcuga guacuucgac ucuaaggguc gagagaccag agaaaucgaa guacucagcg    60
uaag                                                                64
```

METHOD OF RNA CLEAVAGE AND RECOMBINATION

CROSS-REFERENCE TO RELATED APPLICATION

This application claims priority to provisional patent application Ser. No. 60/462,624, filed Apr. 14, 2003, and is a continuation-in-part of U.S. Ser. No. 10/296,574, filed Jan. 7, 2003, which is a §371 of PCT/IB01/01189, which claims priority to Ser. No. 60/208,432, filed on May 31, 2000. All applications listed above are incorporated herein by reference.

STATEMENT REGARDING FEDERALLY SPONSORED RESEARCH OR DEVELOPMENT

Not applicable.

BACKGROUND OF THE INVENTION

Accuracy in tRNA splicing is essential for the formation of functional tRNAs and, hence for gene expression. In Bacteria, tRNA introns are self-splicing group I introns and the splicing mechanism is autocatalytic. In Eukarya, tRNA introns are small and invariably interrupt the anticodon loop one base 3' to the anticodon. In Archaea, the introns are also small and often reside in the same location as eukaryal tRNA introns.

In both Eukaryotes and Archaea, the specificity for recognition of the pre-tRNA resides in the endonucleases. These enzymes remove the intron by making two independent endonucleotytic cleavages. The archaeal enzyme acts without any reference to the mature domain (mature-domain independent mode, MDI) but instead recognizes a structure, the bulge-helix-bulge (BHB) motif, that defines the intron-exon boundaries. The eukaryal enzyme normally acts in a mature-domain dependent mode (MDD); the enzyme recognizes a tripartite set of RNA elements. One subset of recognition elements is localized in the mature domain, while two other subsets are localized at the exon-intron boundaries. A pivotal role is played by a base-pair located near the site of 3' cleavage, the so-called anticodon-intron pair (A-I pair). A purine is strongly preferred at the position preceding the 5' cleavage site.

The primary and secondary structures at the exon-intron junctions of the archaeal and eukaryal pre-tRNAs do not show evident similarities, with the exception of the three-nucleotide bulged structure, closed by the A-I pair and containing the 3' cleavage site, that resembles half of the BHB. The endonuclease are evolutionarily related, but their substrate recognition properties appear drastically different. It has previously been shown, however, that the *Xenopus* and the yeast endonucleases retain the ability to operate in the MDI mode.

BRIEF SUMMARY OF THE INVENTION

In one embodiment, the present invention is a method of cleaving a target RNA molecule comprising the step of exposing in vitro or in vivo the target molecule to an eukaryotic tRNA splicing endonuclease, wherein the target molecule is in the bulge-helix-bulge conformation, wherein cleavage occurs within the bulge-helix-bulge and cleavage products are generated, and wherein the target molecule does not comprise a tRNA structure.

In a preferred embodiment, the bulge-helix-bulge conformation is obtained by hybridizing the target RNA with an oligonucleotide designed to form a bulge-helix-bulge conformation.

In another preferred embodiment, the bulge-helix-bulge conformation is obtained by hybridizing the target RNA with a second RNA wherein the hybridized target RNA and second RNA form a bulge-helix-bulge conformation.

In other embodiments, the target molecule is an mRNA molecule and the oligonucleotide comprises either an RNA molecule, a DNA molecule or a molecule wherein at least one nucleotide is not a ribonucleotide.

In another embodiment, the present invention is a method of cleaving a target RNA molecule comprising the step of exposing the target molecule in a cell to heterologous archeael tRNA splicing endonuclease, wherein the target molecule is in the bulge-helix-bulge conformation, wherein cleavage occurs between the second and third nucleotides at the bulges and cleavage products are generated, and wherein the target molecule does not comprise a tRNA structure. Preferably, the bulge-helix-bulge conformation is created by two mRNA molecules, wherein the two mRNA molecules are the target RNA molecule and a second RNA molecule and additionally comprises the step of ligation of cleavage products from the target RNA and the second RNA, wherein a fusion RNA is formed comprising at least one cleavage product from the first target RNA molecule and at least one cleavage product from the second target RNA molecule.

This invention is also a method for recombining a target RNA molecule that is in the bulge-helix-bulge (BHB) conformation with an exogenous, or targeting, RNA molecule. As described above, the target RNA molecule has been shown to be cleaved within the bulge-helix-bulge. When the cleaved target RNA molecule and the exogenous RNA molecule are exposed to an appropriate ligase, RNA chimeras form, recombining the target RNA molecule and the exogenous RNA molecule across the bulge-helix-bulge. The method of the present invention can be used for recombining RNA molecules that can be used for altering RNA function. The recombination may be used to destroy RNA function, modify RNA, or even restore RNA function.

In another embodiment, the endonuclease, preferably the tRNA endonuclease of the archeobacterium *Metahnococcus Jannaschii* (MJ), when expressed in an eucaryotic organism can be used to modulate gene expression at the post-transcriptional level. The endonuclease recognizes and splices RNA molecules when the latter have Bulge-Helix-Bulge (BHB) structures. Since the ends that the endonuclease creates are ligated by an endogenous RNA ligase, it is possible to activate, inactivate and fuse RNA molecules.

In another embodiment, the invention is a line of transgenic mice that expresses a heterologous tRNA endonuclease in a manner that is constitutive in various tissues.

Other features, objects and advantages of the present invention will be apparent to one of skill in the art after review of the specification and claims.

BRIEF DESCRIPTION OF THE SEVERAL VIEWS OF THE DRAWING

FIG. 1B depicts a substrate cleaved in both the mature-domain dependent and the mature-domain independent modes.

FIG. 2B shows that the yeast endonuclease mutant sen2-3 cleaves pre-tR-NA$^{Archeuka}$ at both sites. FIG. 2C is a comparison of models of enzyme-substrate interaction.

FIG. 7 depicts splicing analysis of mRNAs deriving from NIH3T3 cells transfected with pMJ or put-MJ plasmids, and pGFP of, pGFPof+3 and pGFPof-STOP target constructs.

FIG. 9 is a splicing analysis on mRNAs derived from NIH3T3 cells transfected with pMJ or put-MJ plasmids, and pGFP-BHB or pGFP-BHB target constructs.

FIG. 15A is a northern blot analysis.

DETAILED DESCRIPTION OF THE INVENTION

In one embodiment, the present invention is a method of RNA cleavage involving substrate recognition by tRNA splicing endonucleases. Example 1 describes features required for eukaryotic endonuclease cleavage. Example 2 describes in vitro experiments designed to cleave a mouse mRNA. Example 3 describes in vivo cleavage and re-ligation of mRNAs in mouse cells.

In another example, the present invention is a method for recombining a target RNA molecule that is the bulge-helix-bulge (BHB) conformation with an exogenous, or targeting, RNA molecule. Examples 4 and 5 disclose a splicing reaction in mouse cells.

In another embodiment, the present invention is a method of RNA cleavage or RNA cleavage and religation in a mammal. Example 6 demonstrates one embodiment of this aspect of the invention.

RNA Cleavage by tRNA Splicing Endonucleases

In one embodiment, the present invention is a method of cleaving a double-stranded RNA molecule, wherein the molecule has assumed a bulge-helix-bulge (BHB) conformation. (For a more complete understanding of the structural requirements for the BHB conformation, one should closely examine all figures.) The bulge-helix-bulge conformation comprises an RNA bulge on one strand, a 4 base-pair helix, and an RNA bulge on the opposite strand. The bulges are typically 3 nucleotides in length and the cleavage sites are as described in FIG. 1. In general, the BHB is cleaved (going in the direction 5'-3') at the bond between the second and third nucleotide at the bulges.

In one method of the present invention, one would expose a BHB-containing RNA to a tRNA splicing endonuclease, an enzyme known to be present in all eukaryotic cells and in archeobacteria. The cleavage reaction can be performed both in vitro and in vivo (see Materials and Methods). While the material presented below in the Examples describes certain preferable and typical cleavage reactions, one of skill in the art will know that modifications in reaction conditions, such as enzyme and substrate concentration and buffer and reaction condition components, would be modified to produce successful cleavage reactions.

The cleavage is in the absence of the mature domain of the tRNA structure or sequence. The molecule to be cleaved does not require the D, T and acceptor arm of tRNA structure.

Figure 4:
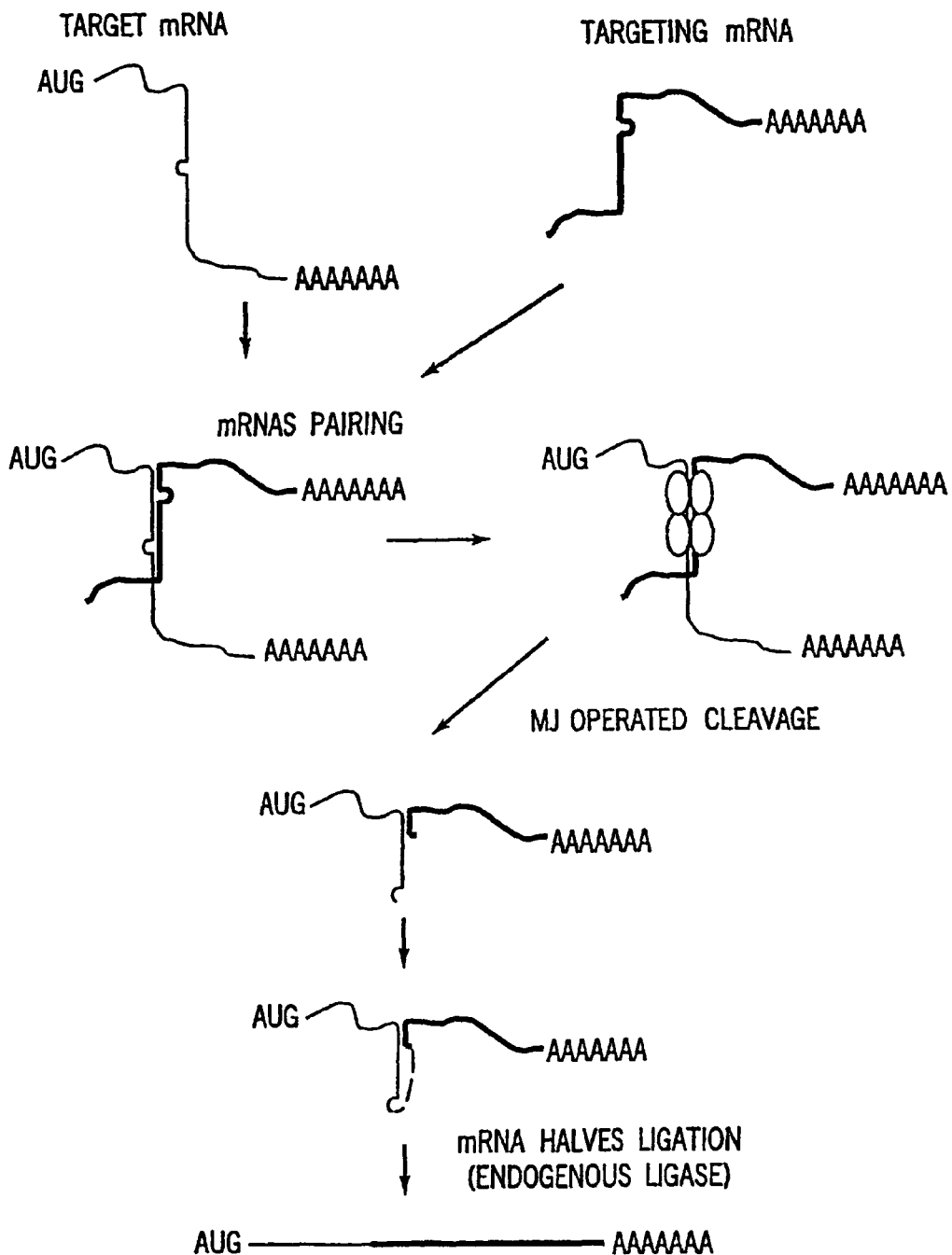
FIG. 4 is a diagram of BHB-mediated trans-splicing.

The BHB could result by the folding of an RNA molecule (BHB in cis) or it could be generated using two different RNA molecules (BHB in trans) (see FIG. 4). One could also design an oligonucleotide capable of forming a BHB structure when hybridized to a target RNA. Therefore, in principle one may target the cleavage site to any desired location on an RNA molecule.

Creation of Oligonucleotides

One of skill in the art of molecular biology would understand how to create an oligonucleotide that would result the bulge-helix-bulge conformation and appropriate splicing site. Preferably, such an oligonucleotide would be at least between 50 and 70 nucleotides long. Most preferably, the oligonucleotide would be between 58 and 62 nucleotides. In this oligonucleotide, at least approximately 25 (±5 nucleotides) nucleotides would be needed on either side of the bulge-helix-bulge conformation.

The oligonucleotide is preferably RNA or a modified RNA molecule. However, we envision that a DNA oligonucleotide would also be suitable.

Selection of tRNA Splicing Endonuclease

Preferably, one would use in in vitro experiments eukaryal (preferably yeast, *Xenopus*, *C. elegans*) and archaeal tRNA splicing endonucleases (preferably *M. jannaschii*). In in vivo embodiments (preferably mammalian cells) one would preferably utilize endogenous tRNA splicing endonucleases and express one of a battery of archaeal enzymes (*Archeoglobus fulgidus, Pyrobaculum aerophilum, Halobacterium* sp. NRC-1, *Methanocuccus jannaschii*). Typically the archaeal enzymes can be expressed in a mouse in a conditional fashion (space and time) utilizing specific mouse promoters. The genes coding for the archaeal enzymes can be cloned from the genome of the original organisms.

Preferred Applications

One could construct a BHB in trans with any cellular RNA and, therefore, provide cleavage at a desired sequence. Preferred applications include using the RNA cleavage method to cut a target RNA into defined ends with a 2',3' cyclic phosphate capable of being ligated. One would also use the present invention to degrade particular targeted RNAs.

One could use the present invention to demonstrate the presence of particular RNAs. For example, one could label an oligonucleotide, wherein the oligonucleotide is capable of forming the BHB structure with the RNA target, and look for cleavage products after the duplex has been exposed to the endonuclease. This may be by means of FRET (fluorescence resonance energy transfer), where one would observe a fluorescent signal if the two ends of a fluorescently labeled oligonucleotide probe were separated.

Therapeutically, one could use the method of the present invention to treat or remove unwanted RNAs from cells. Particular examples would be viral RNAs. In one embodiment, one would express oligonucleotide probes, wherein the probe is capable of forming the BHB structure with a target RNA, into the desired cell. Endogenous tRNA splicing endonucleases or archaeal enzymes expressed in mammalian cells would then cleave the target RNA.

In a preferred form of the present invention, one would avoid the presence of ADAR enzymes ("Adenosine Deaminases Acting on RNA") by either providing a substitute ADAR substrate (such as excess double-stranded RNA) or designing a target oligonucleotide that is appropriate for cleavage by the tRNA splicing endonuclease but not cleavage by the ADAR.

Proteins are traditionally identified on the basis of their individual actions as catalysts, signaling molecules, or building blocks. Our post-genomic view is expanding the protein's roles into an element in a network of protein:protein interactions as well, in which it has a contextual or cellular function within functional modules. The network of protein interaction forms a highly non-homogenous scale-free network in which a few highly connected proteins (hubs) play a central role in mediating interaction among numerous, less connected proteins. The method disclosed in this application allows for the production of fusion proteins, without altering the chromatin structure. In perspective, the fusion of two hubs can be used to generate an algebra of the networks.

Laboratory applications of the present invention include, but are not limited to, tagging proteins and conditional production of RNA hairpins. Clinical applications of the present invention include, but are not limited to, mechanisms for correcting mutations and antiviral therapies.

Use of Archaeal Enzymes in In Vivo Cleavage and Formation of Fusion RNAs

In another form of the present invention, one would cleave in vivo two different RNAs, as described above, and re-ligate the fragments. This embodiment is described in FIGS. 4-6 of the present invention. Typically, one would cotransfect a cell with two plasmids: one coding for an RNA that could form a BHB in trans with another RNA coded by the second plasmid. One could in vivo conditionally (space and time) activate an mRNA containing a BHB inserted in the coding sequence. Excision of the intron and ligation reconstitutes the correct reading frame.

In a preferred form of this embodiment, the in vivo cleavage and formation of fusion RNA is within a cell selected from mammalian cells, plant cells and eubacterial cells. Preferably, the cleavage and re-ligation is within mammalian cells. Additionally, the present invention is the creation and use of transgenic mammalian expression systems. Example 6 describes the creation and use of a transgenic mouse.

In principle, one could generate a zoo of mice conditionally (in space and time) expressing the archaeal enzyme. These mutant mice could be used to correct specific genetic defects or to generate fusion proteins.

The Examples below describe a preferred manner of setting up such an in vivo or in vitro embodiment. Of course, one of skill in the art would understand that modifications in enzyme and substrate concentration and reaction conditions would be within the scope of the invention and not affect the ultimate creation of cleavage products and formation of fusion RNA.

EXAMPLES

Materials and Methods: Targeted RNA Cleavage by tRNA Splicing Endonuclease (Examples 1 and 2)

Amplification

PCR was performed in 100 µl reaction containing 5-10 fmole of template, 100 µM of each primer, 125 µM dNTP, 1.5 mM $MgCl_2$, 50 mM KCl, 10 mM Tris-HCl pH 8.2, 5 U of native Taq Polymerase (Perkin-Elmer) under the following conditions: 95° C. 30 seconds, 55° C. 10 seconds, 72° C. 2 minutes for 18 cycles. The DNA phenol extracted and ethanol precipitated.

Transcription

Transcription of templates by T7 RNA polymerase was performed in 40 mM Tris HCl pH 8.0, 6 mM $MgCl_2$, 10 mM dithiothreitol, 2 mM spermidine, 500 µM ATP, CTP and GTP and 100 µM UTP, 2.5 mM 5' GMP, 2.5 µM $[a^{32}P]$ UTP (800 Ci/mmole, Amersham) using 5 U/µl T7 RNA polymerase (Pharmacia), 0<1 U/µl RNAguard (Pharmacia) at 37° C. for 90 minutes. After phenol extraction and ethanol precipitation, transcripts were purified on a 8% denaturing acrylamide gel, eluted and ethanol precipitated.

Endonuclease Assay

Labeled precursors (0.7 nM) were incubated in 30 µl reaction mixture containing 10 mM HEPES pH 7.5, 7 mM $MgCl_2$, 70 mM $NH_4Cl$, 2.5 mM dithiothreitol, 10% glycerol (v/v) with 10 µl of purified endonuclease at 22° C. for 30 minutes. Cleavage products were analyzed by gel electrophoresis on 12% denaturing polyacrylamide gels.

tRNA Synthesis

Pre-tRNA$^{Phe}$ and pre-tRNA$^{Phe(U-A\ G-C)V}$ were synthesized as described (E. Mattoccia, et al., *Cell* 55:731-738, 1988; M. I. Baldi, et al., *Science* 255:1404-1408, 1992; E. Di Nicola Negri, et al., *Cell* 89:859, 1997). Templates for the synthesis of the Archaeuka precursors were constructed by polymerase chain reaction (PCR). The PCR templates were the full-length pre-tRNAs. One primer contained the T7 promoter and part of the 5' exon. The other was comprised of the desired sequence of the 3' exon. Conditions for PCR, transcription by T7 RNA polymerase, and endonclease assays were as described (E. Mattoccia, et al., supra, 1988; M. I. Baldi, et al., supra, 1992; E. Di Nicola Negri, et al., supra, 1997). *Xenopus laevis* endonuclease was purified as in D. Gandini Atardi (D. Gandcini Atardi, et al., *Methods Enzymol.* 181:510-517, 1989).

Transcription

We utilized Ambion Megascript kits.

Transcription products were purified on 8 M urea polyacrylamide gels. After elution the products were alcohol precipitated.

Annealing to Produce dsRNA

Annealing was at 60' at 68° C. in 50 mM TRIS-HCl pH 7 300 mM NaCl 2 mM EDTA, with slow cooling to 35° C., purification on polyacrylamide gels, elution and alcohol precipitation. The concentration of each strand was 0.01 mg/ml.

X.I. Endonuclease Assay

The assay was for 90' at 25° C. in 30 ml total volume 10 mM Hepes pH 7.5, 70 mM NH4Cl 7 mM MgCl2m 2.5 nN DTT, 10% glycerol, substrate 2 nM.

M.J. Endonuclease Assay

The assay was for 30' at 65° C. in 30 ml total volume 40 mTRIS-HCl pH 7.5 5 mM $MgCl_2$, 10% glycerol, 50 mM, substrate 2 nM.

Incubation mixtures were treated with SDS, prot K and phenol, followed by alcohol precipitation. Products were analyzed in 8 M urea polyacrylamide gels. Samples were treated with urea for 5' at 65° C. or with formamide for 5' at 95° C.

Example 1

Eukaryal tRNA splicing endonucleases use the mature domains of pre-tRNAs as their primary recognition elements. However, they can also cleave in a mode that is independent of the mature domain, when substrates are able to form the bulge-helix-bulge structure (BHB), which is cleaved by archaeal tRNA endonucleases. We present evidence that the eukaryal enzymes cleave their substrates after forming a structure that resembles the BHB. Consequently, these enzymes can cleave substrates that lack the mature domain altogether. That raises the possibility that these enzymes could also cleave non-tRNA substrates that have a BHB. As predicted, they can do so both in vitro and in vivo.

Introduction

Accuracy in tRNA splicing is essential for the formation of functional tRNAs, and hence for cell viability. In both Archaea and Eukarya the specificity of splicing resides in recognition of tRNA precursors by tRNA splicing endonucleases (Belfort and Weiner, *Cell* 89:1003-1006, 1997; Trotta and Abelson, The RNA World, pp. 561-583, 1999). Archaeal tRNA splicing endonucleases cleave pre-tRNAs only using an RNA structure comprised of two bulges of three nucleotides each (where cleavage occurs) separated by four base pairs. This structure, called the bulge-helix-bulge (BHB) (FIG. 1A, 2) (Daniels, et al., *J. Biol. Chem.* 260:3132-3134, 1985; Diener and Moore, *Mol. Cell.* 1:883-894, 1998), functions independently of the part of the molecules that constitutes the mature tRNA, so we refer to this type of recognition of the cleavage sites as being the mature-domain independent mode.

In contrast, eukaryal tRNA splicing endonucleases require interaction with the mature tRNA domain for orientation, so we refer to that recognition as the mature-domain dependent mode (Mattoccia, et al., *Cell* 55:731-738, 1988; Reyes and Abelson, *Cell* 55:719-730, 1988).

Recognition of pre-tRNAs by eukaryal tRNA splicing endonucleases normally requires the mature tRNA domain, as well as a base-pair, called the anticodon-intron (A-I) pair (FIG. 1A), which is formed between nucleotides in the anticodon loop and the intron (Baldi, et al., *Science* 255:1404-1408, 1992). The A-I pair must be at a fixed distance from the mature domain for cleavage to occur and cleavage near this base pair generates the 3' splice site. An independent cleavage event, also at a fixed distance from the mature domain (usually at a purine), generates the 5' splice site.

The two modes of substrate recognition are characterized by two distances. In the mature-domain independent mode the helix of the BHB sets the distance between the two bulges; in the mature-domain dependent mode the distance is fixed relative to reference in the mature domain.

While the subunit structures of the eukaryal and archaeal enzymes differ significantly (Trotta and Abelson, supra, 1999), as do the superficial structures of the cleavage sites, we have demonstrated that both the *Xenopus* and yeast tRNA splicing endonucleases can operate in the mature-domain independent mode, characteristic of Archaea (Fabbri, et al., *Science* 280:284-286, 1998). The results reported in this paper explain why the eukaryal endonucleases retain the ability to operate in the mature-domain independent mode when their natural substrates do not have a BHB.

Results and Discussion

Figure 1A:
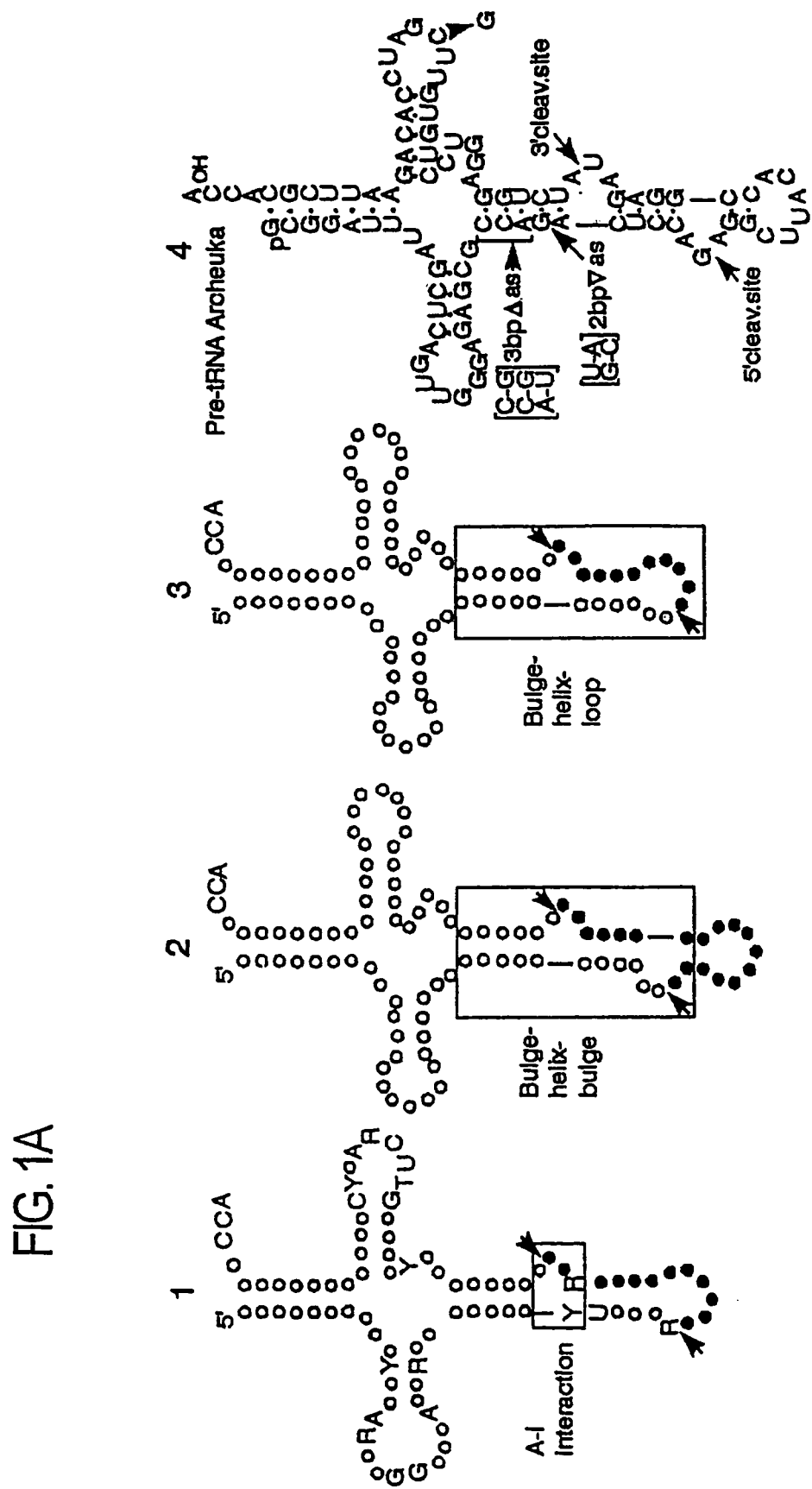
FIG. 1A depicts the A-1 interaction. Pre-tRNA$^{Archeuka}$ (molecule 4) is provided as SEQ ID NO:72 in the sequence listing.

FIG. 1A depicts the A-I interaction. A conserved purine residue in the intron three nucleotides from the 3' cleavage site (molecule 1, R in box) must pair with a pyrimidine in the anticodon loop 6 nucleotides upstream of the 5' cleavage site (molecule 1, Y in box) to form the A-I (for anticodon-intron) interaction (Baldi, et al., supra, 1992). BHB (molecule 2): Two bulges of three nucleotides each (where cleavage occurs) rigidly separated by four base pairs (Daniels, et al., supra, 1985; Diener and Moore, supra, 1998). BHL (molecule 3): A three-nucleotide 3' site bulge, a four base-pair helix and a loop containing the 5' site. Pre-tRNA$^{Archeuka}$ (provided as SEQ ID NO:72 in the sequence listing) and its variants (molecule 4): The hybrid pre-tRNA molecule pre4RNA$^{Archeuka}$ is a substrate for both the eukaryal and archaeal endonucleases. It consists of two regions derived from yeast pre-tRNA$^{Phe}$ (nucleotides (nt) 1-31 and not 38-76) joined by a 25 nt insert that corresponds to the BHB motif of the archaeal pre-tRNATrp. It has a typical eukaryal mature domain with cleavage sites located at the prescribed distance from the reference elements and a correctly-positioned A-I base pair, all of which should ensure correct recognition by the eukaryal endonuclease when the enzyme operates in the mature-domain dependent mode. In addition, the presence of the BHB motif confers substrate characteristics that are recognizable by the eukaryal enzyme when it operates in the mature-domain independent mode. FIG. 1B depicts a substrate cleaved in both the mature-domain dependent and the mature domain independent modes. Products of digestion by the *Xenopus* tRNA splicing endonuclease. Molecule 1: Pre-tRNA$^{Archeuka}$ 3 bpΔas; molecule 2: Pre-tRNA$^{Archeuka}$ 3 bpΔas, C56G.

Figure 2A:
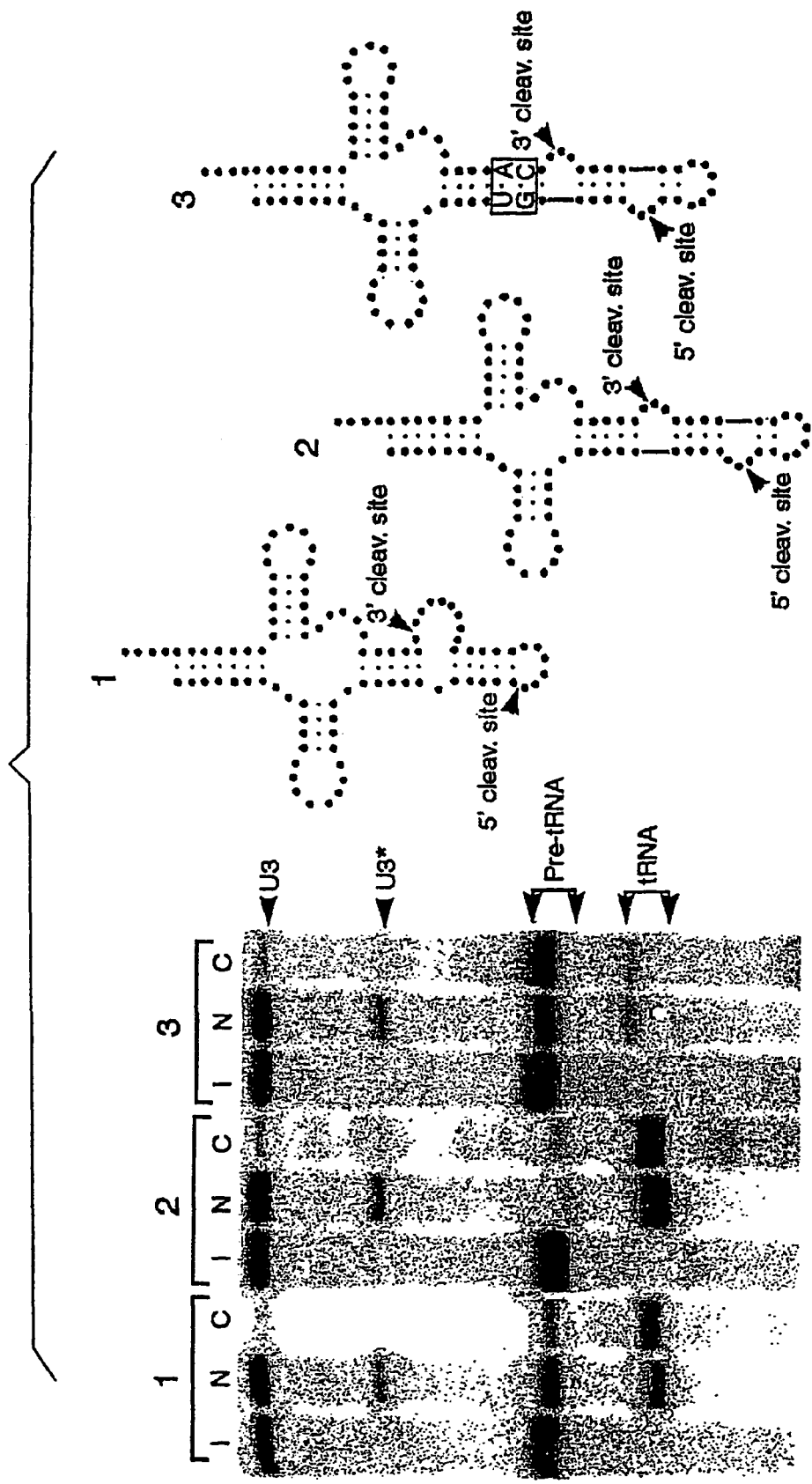
FIG. 2A shows the *Xenopus* endonuclease can cleave in vivo in the mature-domain independent mode.

FIG. 2A shows that the *Xenopus* endonuclease can cleave in vivo in the mature-domain independent mode. Low amounts of $^{32}$P-labeled RNAs corresponding to Pre-tRNA$^{Phe}$ (1); Pre-tRNA$^{Archeuka}$ (2) and Pre-tRNA$^{Archeuka}$ 2 bpVas (3) were injected into nuclei of *Xenopus* oocytes and 2 hours later the intracellular distribution of the injected primary pre-tRNA transcripts and of the mature tRNAs were determined by analysis of total nuclear (N) and cytoplasmic (C)RNAs. The injected precursor RNAs in the cytoplasm probably resulted from inefficient nuclear retention, I., input.

FIG. 2B shows that the yeast endonuclease mutant sen2-3 cleaves pre-tRNA$^{Archeuka}$ at both sites. Molecule 1, pre-tRNA$^{Phe}$; molecule 2, pre-tRNA$^{Archeuka}$; molecule 3, Pre-tRNA$^{Archeuka}$ 3 bp∇BHB, C8G, G24C, X. *Xenopus laevis*; Y, yeast *S. cerevisiae* wild-type; Y* yeast *S. cerevisiae* sen2-3. The sen2-3 preparation was contaminated with a 3' exonucleolytic activity that partially degraded the 3' end of the precursor, reducing the size of the 3' half product. The sequences of the products of the intron excision reaction have been verified by fingerprinting (data not shown). In the sen2-3 mutant, one residue in loop L7, Gly292, is changed to Glu (Trotta and Abelson, supra, 1999). Loop 7 contains a histidine residue that is absolutely conserved in all tRNA endonucleases, and that probably acts as a general base by deprotonating the nucleophile 2'-hydroxyl group (Trotta and Abelson, supra, 1999). The residues on loop 7 immediately surrounding the conserved histidine residue are not conserved among the tRNA endonucleases. We suggest that these residues have a role in the restructuring of the 5' cleavage site in the eukaryal enzymes.

FIG. 2C is a comparison of models of enzyme-substrate interaction: (a) Pre-tRNA$^{Archeuka}$ Eukaryal enzyme (Trotta and Abelson, supra, 1999), (b) Pre-tRNA$^{Archeuka}$ Archaeal enzyme (Trotta and Abelson, supra, 1999), and (c) BHB Eukaryal enzyme.

A proposal for loss of symmetry during evolution of the intron excision reaction. In Archaea, the recognition element in pre-tRNA is the BHB, which has pseudo-two-fold symmetry (Diener and Moore, supra, 1998; Trotta and Abelson, supra, 1999). Since the endonuclease does not bind to the mature domain of pre-tRNA, the enzyme is oriented in such a ways that both active sites can cleave either of the intron-exon junctions (b). The primary recognition element of the eukaryal endonuclease, on the other hand, is the asymmetrically located mature domain of pre-tRNA; interaction with that domain imposes an orientation of the enzyme on the substrate, so that each active site is specific to one or the other intron-exon junctions. In the absence of a mature domain, as with the mini-BHB (Febbri, et al., supra, 1998), the eukaryal enzyme is free to recognize pseudo-two-fold symmetric elements in the substrate, so that both active sites in the enzyme can bind to either junction (c). However, when a substrate has both a mature domain and a symmetric BHB, as in pre-tRNA$^{Archeuka}$, the eukaryal endonuclease can interact with the mature domain, and the added energy of this binding would be likely to orient the enzyme (a).

We propose that during evolution, once endonucleases were able to recognize the mature domain, the need for a symmetric BHB recognition site diminished; however, the active sites of the eukaryal enzymes were maintained, allowing them to cleave pre-formed BHB structures. Because the orientation of the two cleavage sites in the enzyme remained constant, the eukaryal pre-tRNAs had to maintain the ability to form a BHB-like structure upon binding the eukaryal enzyme; part of that requirement is seen in the -A-I base pairing rule and in the BHL.

The artificial substrate pre-tRNA$^{Archeuka}$ contains both a mature domain and a BHB (FIGS. 1A, 2). The eukaryal enzymes cleave the substrate with a two base-pair insert in the anticodon stem, 2 bpVas (FIGS. 1A, 4), only in the mature-domain independent mode (Fabbri, et al., supra, 1998). The sites of cleavage by the eukaryal enzyme are fixed by recognition of local BHB structure rather than by reference to the mature domain.

The *Xenopus laevis* endonuclease can also cleave in vivo in the mature-domain independent mode. When pre-tRNA$^{Archeuka}$ and pre-tRNA$^{Archeuka}$ 2 bpVas were injected into *Xenopus* oocyte nuclei, both substrates were spliced and ligated. The size of the mature pre-tRNA$^{Archeuka}$ 2 bpVas, which is four bases longer than mature wild-type pre-tRNA$^{Phe}$, indicates that the *Xenopus* enzyme cleaves in the mature-domain independent mode in vivo just as it does in vitro (FIG. 2A). The substantial amounts of each precursor exported before cleavage probably results from saturation of nuclear retention (Arts, et al., *EMBO J.* 17:7430-7441, 1998; Lund and Dahlberg, *Science* 282:2082-2085, 1998).

Some substrates are cleaved in both modes. Pre-tRNA$^{Archeuka}$ 3 bpΔas (FIG. 1B), which has a three base-pair deletion in the anticodon stem, is cleaved in both modes. In this case, the two modes yield distinct product sizes, and both are observed. Two introns are visible in FIG. 1B, lane 1. One of the products is not produced in the C56G mutant reflecting the inability of the enzyme to cleave a substrate that cannot form a normal mature domain in the mature-domain dependent mode.

We now propose that the orientation of the substrate in the active site of the eukaryal enzyme requires the formation of a structure that resembles a BHB; the A-I pair would play a pivotal role in this process, as it represents the closing base pair of one of the bulges. This model predicts that recognition of the mature tRNA domain by a eukaryal tRNA splicing endonuclease allows subsequent formation of a BHB-like cleavage structure.

In addition to the A-I pair (Baldi, et al., supra, 1992), other relics of the archaeal world provide insight into the mechanism of the eukaryal cleavage reaction. Some eukaryal pre-tRNAs present motifs that resemble the BHB. The sequence of the *Caenorhabditis elegans* genome shows the tRNA genes corresponding to three isoacceptor species (Leu, Tyr, Ile) contain introns (The *C. elegans* Sequencing Consortium, 1998). The nematode pre-tRNAs present a motif which we call BHL (FIGS. 1A, 3), which resembles the BHB in that it has the 3' site bulge and the four base-pair helix but the 5' site is in a loop rather than in bulge. These three intron-containing pre-tRNAs of *C. elegans* are cleaved correctly by both yeast and *Xenopus* endonucleases, as well as the *Parascaris equorum* tRNA splicing endonuclease, but not by the archaeal enzyme (data not shown). Thus, the only truly universal substrate is an RNA with a BHB (Fabbri, et al., supra, 1998).

Because they can both cleave the BHB, the archaeal and eukaryal endonucleases are likely to have identical dispositions of active sites, a feature conserved since their divergence from a common ancestor (Trotta and Abelson, supra, 1999; Fabbri, et al., supra, 1998) (FIG. 2C). We suggest that the mature-domain dependent mode arose through specialization of the subunits of the eukaryal enzyme.

We propose that the eukaryal enzymes possess a mature-domain dependent 5' site restructuring activity (Di Nicola, et al., *Cell* 89:859-866, 1997). Such an activity would be required for the last steps of substrate recognition by the eukaryal enzymes, recapitulating the recognition process of their archaeal counterparts. The 5' site restructuring activity is not needed to cleave the BHB because it already has a correctly structured 5' site; however the activity is responsible for improving the efficiency of cleavage at the 5' site in BHL (P. Fruscoloni, M. Zamboni, M. I. Baldi and G. P. Tocchini-Valentini, manuscript in preparation). The *Ascaris* enzyme also has a mature-domain dependent 5' restructuring activity, but it differs from that of *Xenopus* because it is unable to restructure a typical eukaryal pre-tRNA such as yeast pre-tRNA$^{Phe}$ (P. Fruscoloni, M. Zamboni, M. I. Baldi and G. P. Tocchini-Valentini manuscript in preparation).

Our model predicts the existence of mutants of the eukaryal enzyme that lack the 5' restructuring activity. Such mutants would be unable to cleave a eukaryal pre-tRNA at the 5' site, but could cleave at the 3' site. More importantly, these restructuring mutants should cleave precursors that already have a BHB.

The yeast endonuclease is an αβγδ heterotetramer (Trotta, et al., *Cell* 89:849-858, 1997). Homology relationships and other evidence suggest that two subunits of the enzyme, Sen2p and Sen34p, contain distinct active sites, one for the 5' site, the other for the 3' site. The mutant sen2-3 is defective in cleavage of the 5' site (Ho, et al., *EMBO J.* 9:1245-1252, 1990); FIG. 2B shows that sen2-3 extracts cleaves the 3' but not the 5' site of yeast pre-tRNA$^{Phe}$. The same extract, however, cleave pre-tRNA$^{Archeuka}$ at both sites (FIG. 2B). Thus, sen2-3 cleaves the 3' but not the 5' sites in substrates lacking a BHB, as would be expected if it lacked the mature-domain dependent 5' site restructuring activity. This conclusion is reinforced by the fact that pre-tRNA$^{Archeuka}$ 3 bpVBHB, a substrate that can interact with the enzyme only in the mature-domain dependent mode, is cleaved only at the 3' site (FIG. 2B).

It is unlikely that the lack of cleavage at the 5' site of pre-tRNA$^{Phe}$ results simply from inactivation of the catalytic site since the mutated amino acid is not near this site, based on the crystal structure of the enzyme (Li, et al., *Science* 280: 279-284, 1998). Moreover, pre-tRNA$^{Archeuka}$, which has a BHB, is cleaved at both sites even though its mature domain should prevent binding of the sen34 active site to the 5' site (FIG. 2B). Unfortunately, expression of a sen2-3 and sen34 double mutant enzyme is very likely to be lethal, making production of a doubly mutated enzyme impossible.

Example 2

Figure 3:
FIG. 3 depicts cleavage of a non-tRNA molecule by the Xenopus endonuclease.

The ability of the eukaryal enzyme to recognize and cleave independently of the mature domain creates the possibility for cleavage of non-tRNA substrates (FIG. 3). If the eukaryal endonuclease can recognize and cleave substrates in the mature-domain independent mode, any RNA that contains a BHB structure should be able to serve as a substrate. Such a target could be generated in mRNA by adding a suitable RNA oligonucleotide.

FIG. 3 depicts cleavage of a non-tRNA molecule by the *Xenopus* endonuclease. Profilin I mRNA duplexes (cartoon) consisting of 32P-labeled sense strand and cold antisense strand (0.6 nM) were incubated with *Methanococcus jannaschii* endonuclease (MJ for 30 minutes at 65° C.); *Xenopus laevis* endonuclease (XL for 90 minutes at 25° C.); germinal vesicles extract (GV for 90 minutes at 25° C.). The reacted RNA was treated as described (Mattoccia, et al., supra, 1988; Baldi, et al., supra, 1992; Fabbri, et al., supra, 1998) and analyzed in 8M urea polyacrylamide gels. Two fragments were generated from profilin I mRNA (417 nts and 53 nts). The gel shows only the larger fragment. Unrelated 32P-labeled dsRNA (low specific activity) was added where indicated (the concentration was 300× that of the profilin I duplex). C, duplex containing the BHB; C1, full duplex.

FIG. 3 shows that the archaeal and eukaryal enzymes cleave mouse profilin 1 mRNA (Widada, et al., *Nucleic Acids Res.* 17:2855, 1989), when the RNA is complexed with another oligoribonucleotide forming a BHB. This cleavage occurs in a BHB-dependent manner because fully double-stranded molecules (FIG. 3) and molecules presenting an insertion of three base pairs in the helix of the BHB are not cleaved (data not shown). FIG. 3 shows that cleavage also occurs in extracts of germinal vesicles (GV extracts). Again, cleavage is BHB-dependent. However, cleavage in this extract occurred only in the presence of a 100-fold excess of unrelated double-stranded RNA (dsRNA). Pre-tRNA$^{Archeuka}$, on the contrary, is cleaved at high efficiency (data not shown). An explanation for these differences is the presence in GV extracts of adenosine deaminases (ADARs) that convert adenosines to inosines within dsRNA (Bass and Weintraub, *Cell* 35:1089-1098, 1988), thereby causing the RNA duplex to fall apart, disrupting the BHB structure. Presumably, at low concentration of dsRNA, ADARs deaminate the substrate and, as a result of the increased single-stranded character of the molecule, the BHB is destroyed.

Our results indicate that the formation of a BHB is an obligate step in cleavage by the eukaryal endonucleases and explain why the eukaryal endonucleases retain the ability to operate in the mature-domain independent mode when their natural substrates do not have a BHB.

Example 3

This work is disclosed in Deidda, et al., *Nat. Biotechnol.* 12:1499-1504, 2003, incorporated by reference.

RNA Engineering

Various approaches are currently being used to elucidate the principles that underlie the construction and function of eukaryotic cells and organisms. Some of these approaches, such as gene targeting or the gene trap technology, operate at the level of the DNA. Others, like the Tet system, regulate gene expression at the level of transcription. Yet another kind of approach, such as induced dimerization, works at the protein level.

It is becoming clear that processes occurring at the RNA level such as, for example, alternative splicing and editing, play an extremely important role in expanding protein diversity and might therefore be partially responsible for the apparent discrepancy between gene number and complexity. Developing a full catalogue of transcripts corresponding to a single gene and determining each of their functions will be a major challenge of the proteomic era. What is needed is a technology that makes RNA engineering possible.

The BHB is recognized and cleaved by archaeal and eukaryal tRNA endonucleases. It is therefore possible to generate non-tRNA substrates for the enzymes; any RNA that contains a BHB structure is capable of serving as a substrate. Such a target can be generated in mRNA either by inserting a BHB in cis in the coding or untranslated regions, or by adding a suitable RNA oligonucleotide to form a BHB in trans.

In mouse cells, we have found that the halves generated by cleavage of BHB in cis in a mRNA molecule are ligated by an endogenous ligase activity. FIG. 4 shows that, when the BHB is formed in trans by two different RNA molecules, a fusion mRNA may result.

Figure 5:
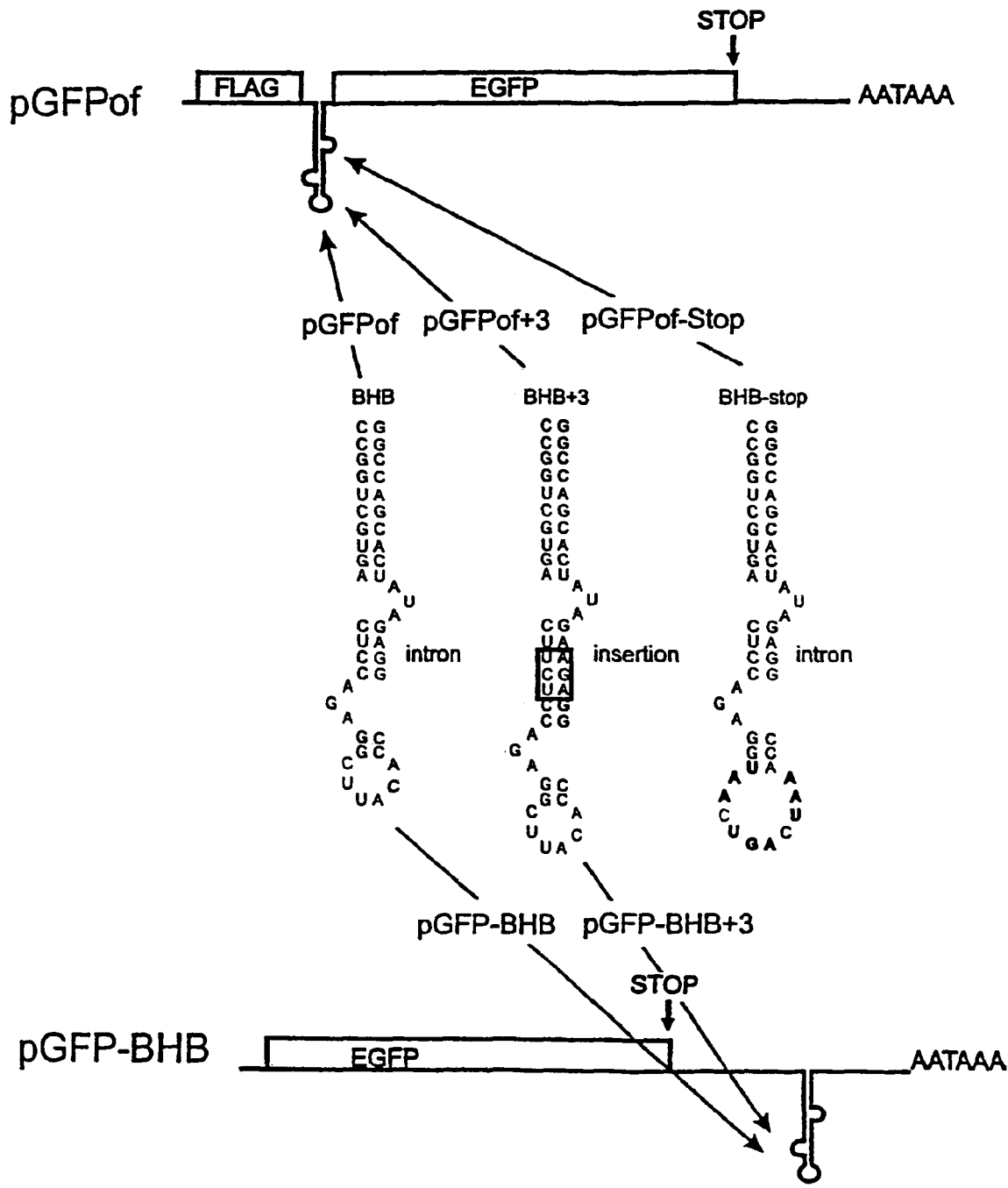
FIG. 5 describes a scheme of BHB (bulge-helix-bulge) insertions in the GFP mRNAs. The upper and lower parts of the figure show the structure of the GFP of and the GFP-BHB genes, as well as the BHB position. In the middle, the different BHB substrates are detailed. The BHB (provided as SEQ ID NO:73 in the sequence listing) and the BHB-stop (provided as SEQ ID NO:74 in the sequence listing) are processed by the MJ-endoribonuclease whereas the BHB+3 (provided as SEQ ID NO:75 in the sequence listing) is MJ-endoribonuclease insensitive. Intronic ribonucleotides are underlined, stop codons blocking all reading frames are in bold face and the base-pair insertion disrupting the canonical BHB structure is boxed in green.

A sequence was inserted in the coding region of the GFP gene so that the transcription of the coding strand yields an mRNA harbouring a canonical BHB (FIG. 5). The mutated GFP gene was named "GFPof," since the presence of the intron in the messenger renders the latter out of frame. Production of GFP requires that the intron be precisely excised and that the exons be subsequently ligated.

Figure 6C:
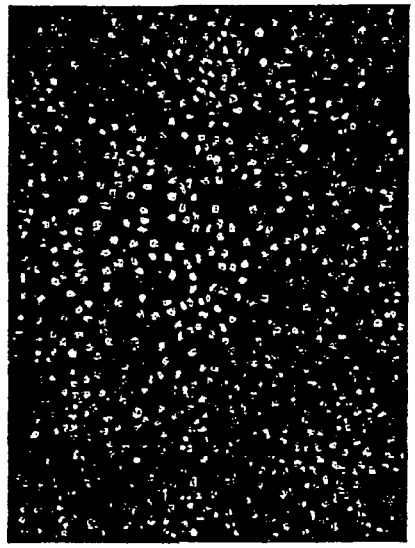
FIG. 6 depicts direct GFP and Hoechst fluorescence of NIH3T3 transiently transfected with different plasmids as indicated in the figure. Transient transfections were performed with (a) 0.5 µg pEGFP-N3 plus 1.5 µg pMJ; (b) 0.5 µg pGFP of plus 1.5 µg of pMJ; (c) 0.5 µg pGFP of plus 1.5 µg put-MJ; (d) 0.5 µg pGFP of +3 plus 1.5 µg pMJ.
Figure 6D:
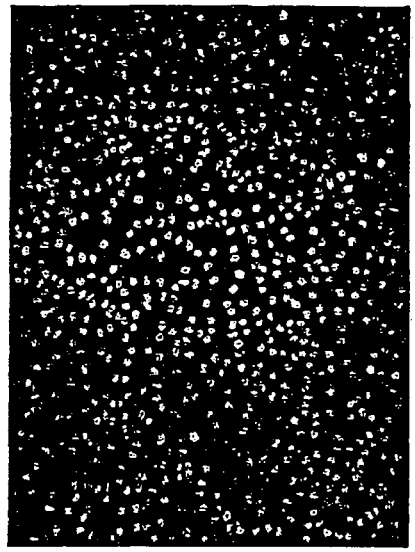
Figure 7A:
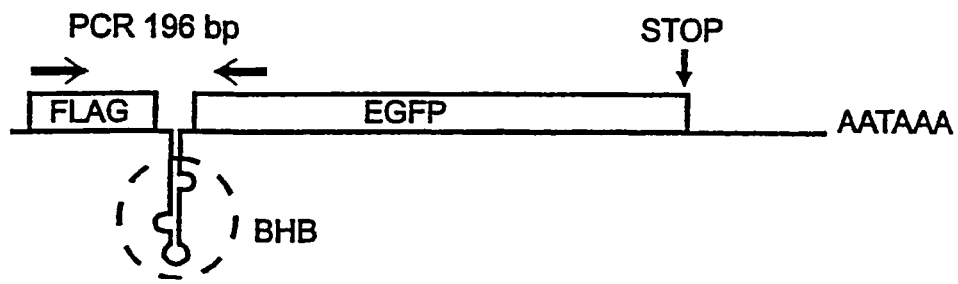
FIG. 7A mRNA structure of pGFPof, pGFPof+3 and pGFPof-STOP target constructs and the PCR primers position.
Figure 7B:
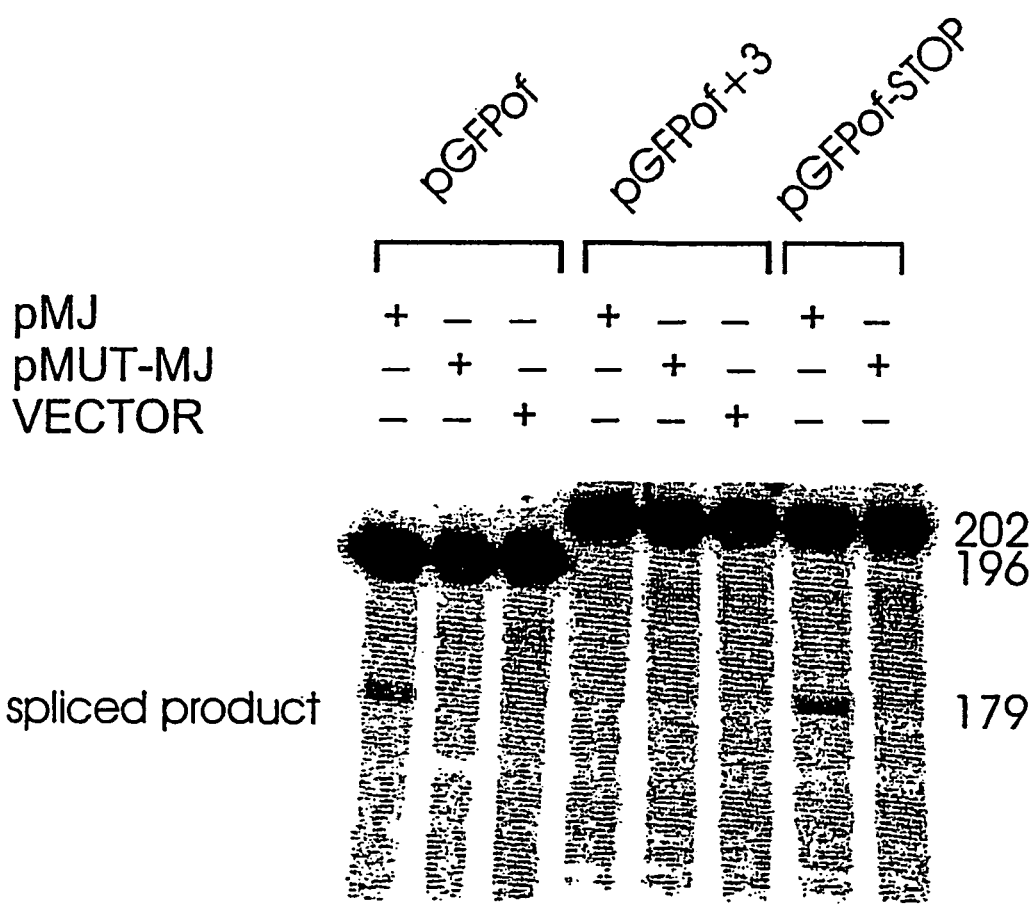
FIG. 7B RT-PCR analysis of different GFP mRNA in the presence or absence of functional MJ enzyme. NIH3T3 were transiently transfected with different plasmids as indicated in the figure. A constant 1:3 molar ration between plasmids coding for target tRNAs and for MJ-endoribonuclease was used.
Figure 8:
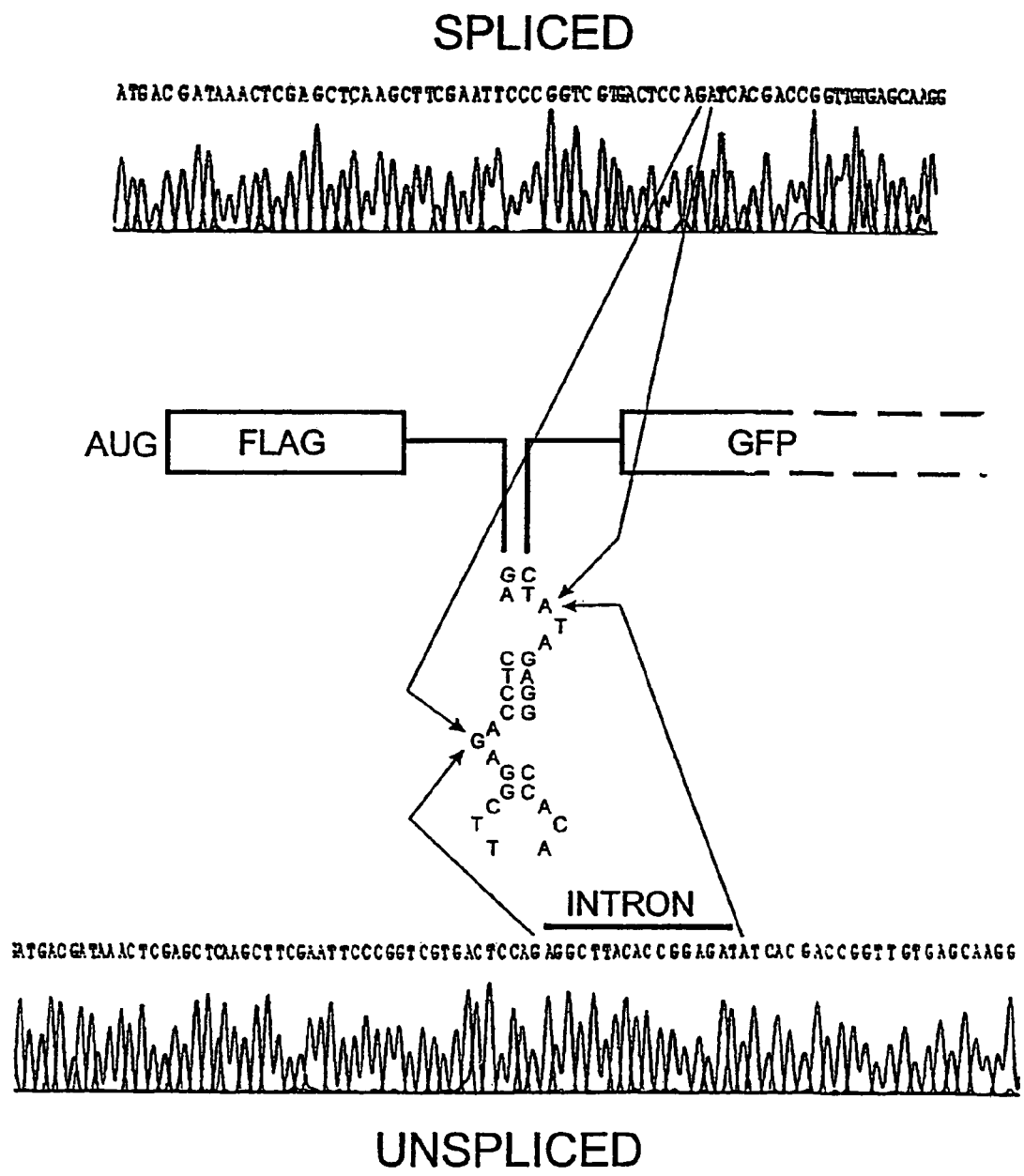
FIG. 8 is a sequence analysis of RT-PCR products derived from NIH3T3 cells transiently transfected with pGFP of and pMJ plasmids. Sequences were performed using RT-PCR products eluted from a gel. In the middle, the arrows indicate the intron-flanking nucleotides. The top spliced sequence, the middle intron sequence, and the bottom unspliced sequence are provided as SEQ ID NO:76, SEQ ID NO:77, and SEQ ID NO:78 in the sequence listing, respectively.

FIG. 6 shows that if 3T3 cells are transiently cotransfected with a plasmid expressing GFPof and a plasmid expressing the *M. jannaschii* endonuclease, GFP is produced. If a plasmid expressing an inactive endonuclease is utilized, GFP is not produced. These results suggest that the *M. jannaschii* endonuclease excises the intron and that an endogenous ligase activity produces a spliced mRNA that is correctly translated. This conclusion is substantiated by the finding that a new RNA species appears (FIG. 7) and that its sequence (FIG. 8) corresponds to that expected for spliced GFP mRNA. In addition, FIG. 7 shows that GFPof+3 mRNA, a transcript characterized by an insertion of three base pairs in the helix of the BHB (FIG. 5), is not spliced. TRNA endonucleases do not tolerate the expansion of the helix of the BHB.

GFPof stop mRNA (FIG. 5), a transcript characterized by a twenty-three base long intron containing three stop codons in the three reading frames, is accurately spliced (FIG. 7).

Figure 9A:
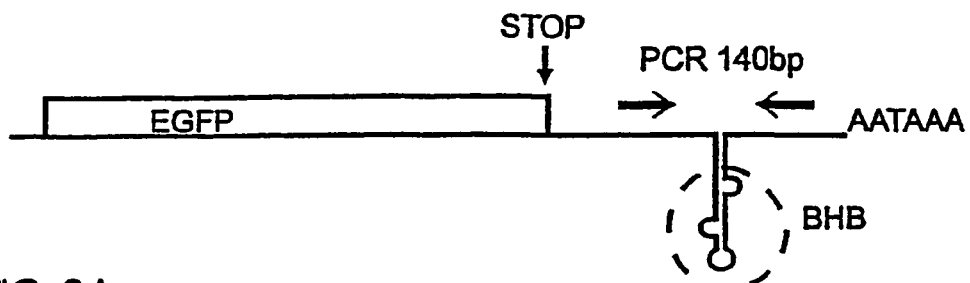
FIG. 9A: mRNA structure of pGFP-BHB+3 target constructs and the PCR primers position.
Figure 9B:
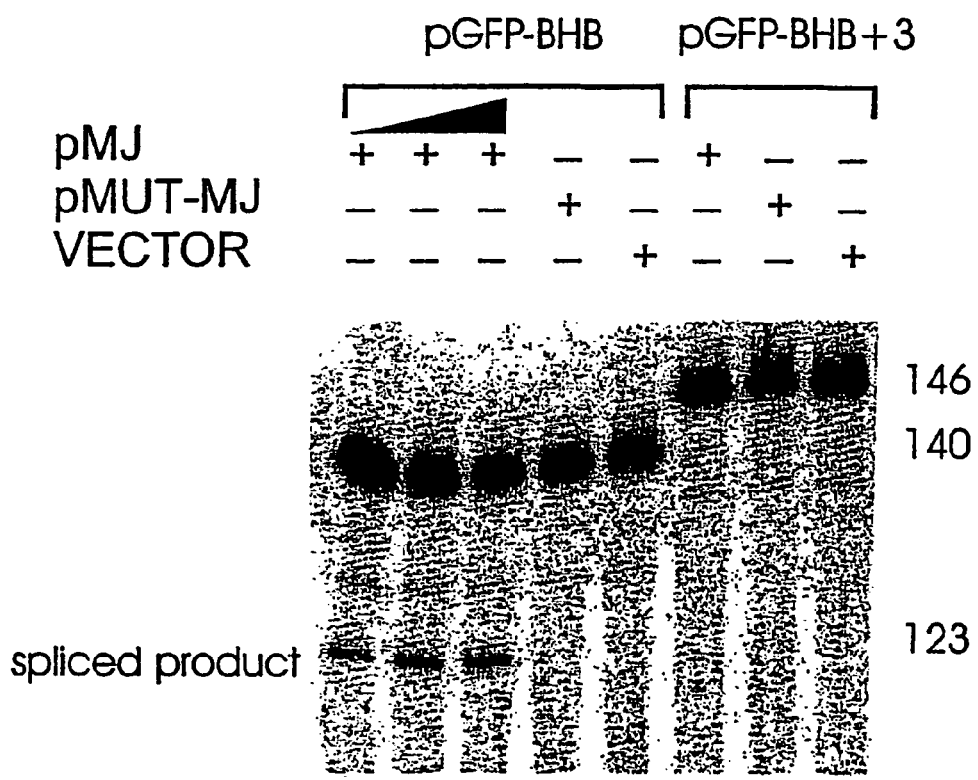
FIG. 9B: RT-PCR analysis of different GFP mRNA in the presence or absence of functional MJ enzyme. NIH3T3 were transiently transfected with different plasmids as indicated in the figure. A constant 1:3 molar ratio between plasmids coding for target TRNAS and for MJ-endoribonuclease was used in lanes 3-8. In lanes 1 and 2 ratios of, respectively, 3:1 and 1:1 were used instead.
Figure 10:
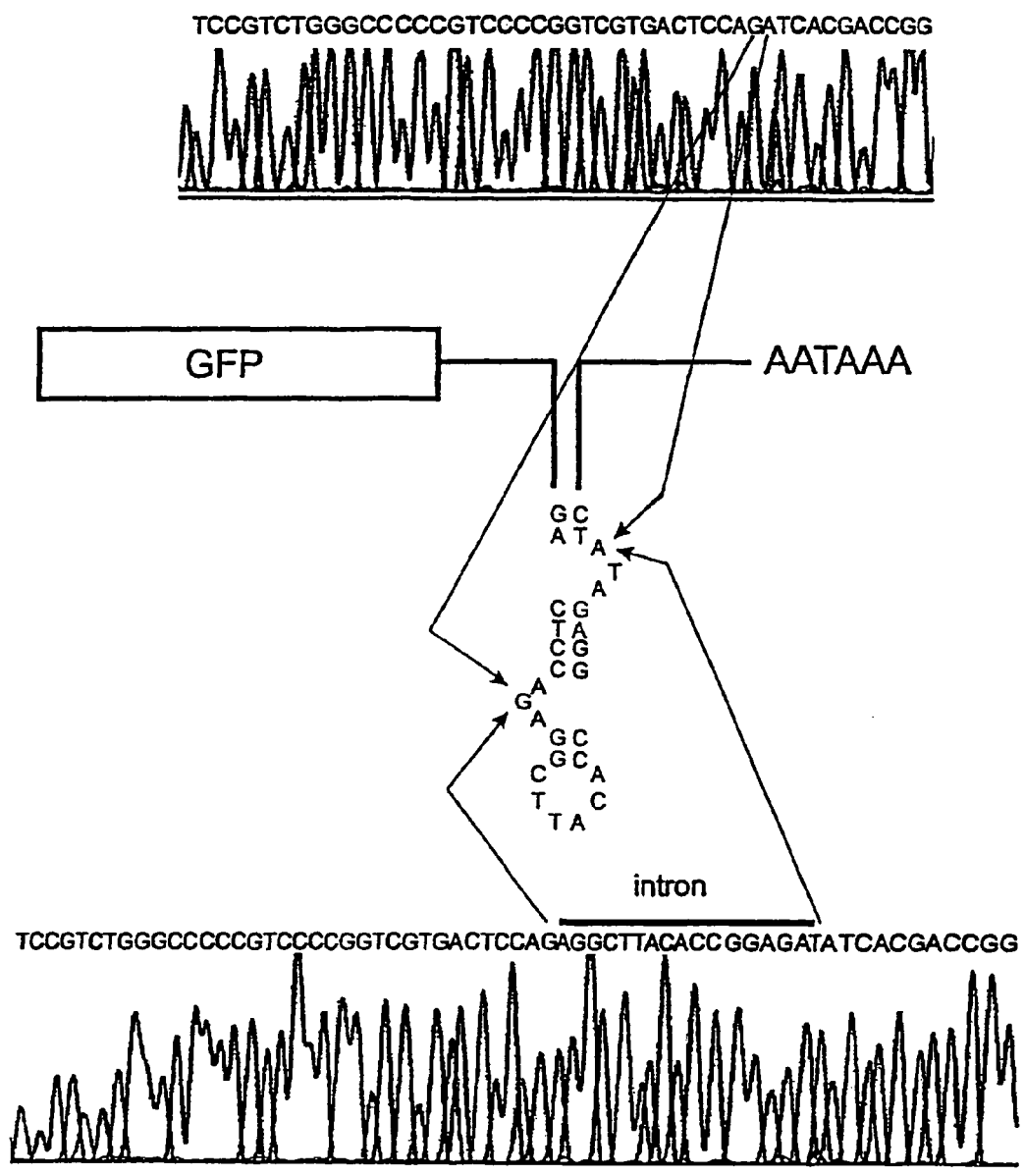
FIG. 10 is a sequence analysis of RT-PCR products derived from NIH3T3 cells transiently transfected with pGF-BHB and pMJ plasmids. Sequences were performed using RT-PCR products eluted from a gel. In the middle, the arrows indicate the intron-flanking nucleotides. The top spliced sequence, the middle intron sequence, and the bottom unspliced sequence are provided as SEQ ID NO:79, SEQ ID NO:80, and SEQ ID NO:81 in the sequence listing, respectively.

A spliced species is also produced when the BHB is not positioned in the coding region. In GFP-BHB mRNA (FIG. 5), the BHB is located in the 3' untranslated region. FIG. 9 shows that if 3T3 cells are transiently cotransfected with a plasmid expressing GFP-BHB and a plasmid expressing the *M. jannaschii* endonuclease, a new RNA species appears whose sequence (FIG. 10) corresponds to that of accurately spliced GFP mRNA.

Structure-Specific Non-Spliceosomal Splicing of mRNA

The *Methanococcus jannaschii* tRNA endonuclease recognizes and cleaves its normal substrates at bulge-helix-bulge (BHB) motifs that define the intron-exon boundaries in archaeal tRNAs and rRNAs. We show that this enzyme also cleaves on either end of a small intron inserted into a eukaryal mRNA encoding the green fluorescent protein (GFP). Moreover, the cleavage products are subsequently ligated together by endogenous RNA ligases in a reaction resembling that described for the HAC1 mRNA.

Introns included in the BHB, located in either the coding region or the 3' UTR, were excised from GFP mRNAs when the gene encoding the *M. janaschii* enzyme was transfected into NIH3T3 cells. Our assays for proper ligation included detection of GFP by fluorescence microscopy and RT-PCR. Disruption of the BHB by extension of the helix results in no splicing.

These experiments demonstrate that the archaeal enzyme can recognize the BHB motif even in the context of a mammalian mRNA. This enzymatic system offers an opportunity to modulate gene expression in vivo.

Materials and Methods

Gene Expression Constructs

Plasmids Coding for mRNAs Containing the BHB Structure.

Splicing-Dependent Translation

GFP-OF was obtained by amplifying the GFP gene from the pEGFP-N3 expression vector (Clontech). The GFP was sequentially amplified with two set of primers: P1 VS P3 and P2 VS P3. A new start codon embedded in a Kozak sequence was inserted and the natural GFP start codon was mutated with the introduction an AgeI site. Moreover, a FLAG epitope coding sequence separated from GFP was separated by the BHB structure. The FLAG and the GFP are coded on two different frames but they switch to the same frame when the BHB is correctly spliced. The modified GFP (GFP-OF) was re-inserted into the BglII-NotI sites of the pEGFP-N3 vector (pGFP-OF).

Plasmids pGFP-OF+3 and pGFP-Stop were obtained by substitution of the EcoRI-AgeI fragment of pGFP-OF with the double stranded oligonucleotides P4 and P5, respectively.

Splicing-Independent Translation

Two different constructs containing the BHB in the 3' UTR were prepared, pGFP-BHB and pGFP-BHB+3. The GFP gene from the pd2EGFP-N1 vector (Clontech) was amplified with the primer pair P2 Vs P8 to add a 35-nucleotide long spacer downstream of the stop codon. The P2-P8 PCR product was then submitted to a new round of PCR with the P2-P6 and P2-P7 primer pairs in order to add the structures BHB and BHB+3, at the 3' end of GFP-BHB and GFP-BHB+3 products. These PCR products were digested with BglII and NotI and cloned back in the original vector.

Plasmids Coding for *Methanococcucs Jannaschii* tRNA Endonuclease.

Construction pMJ Plasmid.

The *M. jannaschii* gene with the FLAG epitope at its 5' end was cloned by PCR from the pET11a bacterial expression vector (Hong Li, et al., *Science* 280:284, 1998) a kind gift of Dr. Christopher Trotta. The MJ-endoribonuclease PCR product was obtained using the primer pair P14 Vs P15 and cloned BglII-NotI in the pd2EGFP-N1 vector after excision of GFP.

The plasmid pMut-MJ was obtained via PCR from pMJ using mutagenic primers. Three aminoacidic substitutions were introduced: His 125 to PHE, LYS 156 to PRO and LYS157 to GLN. The *M. jannaschii* gene was amplified using three different primer pairs: P14 Vs P17, P16 Vs P19 and P18 Vs P5. All PCR products were mixed and re-amplified with P14 Vs P15. The mutagenized product was digested and cloned as was done for pMJ.

TABLE 1

Oligodeoxyribonucleotides (SEQ ID NO: 1)
P1-GAGCTCAAGCTTCGAATTCCCGGTCGT-
GACTCCAGAGGCTTACACCGGAGATATCACGACCGGTTGTGAGCAAGGGCGAG P2-ATCACGAGATCTCCACCATGGACTACAAAGACGATGACGATAAACTCGAGCTCAAGCTTCGAATT (SEQ ID NO: 2)

P3-TCGGGATCCTCTACAAATGTGGTATGGCTG (SEQ ID NO: 3)

(SEQ ID NO: 4)
P4-GCTTCGAATTCCCGGTCGTGACTTCTCCAGAGGCTTACACCGGAGAAGATATCACGACCGGTTGTGA (SEQ ID NO: 5)
P5-GCTTCGAATTCCCGGTCGTGACTCCAGAGGTAACTGACTAAACCGGAGATATCACGACCGGTTGTGA (SEQ ID NO: 6)
P6-ATAAGAATGCGGCCGCCCGGTCGTGATATCTCCGGTGTAAGCCTCTGGAGTCACGACCGGGGACGGG (SEQ ID NO: 7)
P7-ATAAGAATGCGGCCGCCCGGTCGTGATATCTTCTCCGGTGTAAGCCTCTGGAGAAGTCACGACCGGGGACGGG (SEQ ID NO: 8)
P8-TCACGACCGGGGACGGGGGCCCAGACGGAGGGCGAGTCCTTGTAGCGCATCTACACATTGATCCTAGCAGA

P9-CGTCAGATCCGCTAGCGCTAC (SEQ ID NO: 9)

P10-CGTCGCCGTCCAGCTCGACCA (SEQ ID NO: 10)

P11-TAGATGCGCTACAAGGACTCG (SEQ ID NO: 11)

P12-TCGGGATCCTCTACAAATGTGGTATGGCTG (SEQ ID NO: 12)

P14-ATCACGAGATCTCCACCATGGACTACAAAGACGATGACGATAAAATGGTGAGAGATAAAATG (SEQ ID NO: 13)

P15-ATAAGAATGCGGCCGCGGATCCTTATGGTTTTACATAGG (SEQ ID NO: 14)

P16-ATAAAGAATTCTCTGTTTATTTGGTTAAGG (SEQ ID NO: 15)

P17-AACAGAGAATTCTTTATCATGTTAGCTCC (SEQ ID NO: 16)

P18-TCAGTTCGGCCGCAATTACTCATAGCAATC (SEQ ID NO: 17)

P19-GTAATTGCGGCCGAACTGAGTGAGCAACC (SEQ ID NO: 18)

P20-GGCACCACCCCGGTGAACAG (SEQ ID NO: 19)

P21-GTATGGCTGATTATGATCTAG (SEQ ID NO: 20)

Culture Conditions and Cell Transfections

NIH3T3 fibroblasts were grown in Dulbecco's modified medium (DMEM) supplemented with 10% calf serum in a 37° C. incubator with 5% $CO_2$. Cell transfections were carried out using the Lipofectamine 2000 or Lipofectamine Plus (Gibco-BRL) transfection reagent according to the manufacturer's instructions. Each transfection was performed in a 35 mm dish using 4 µg of total plasmid DNA with Lipofectamine 2000 or 2 µg with Lipofectamine Plus.

RNA Preparation and RT-PCR Analysis

Total RNA was isolated from cells 24 hours after transfection using the Trizol reagent (Life Technologies) following the manufacturer's instructions. 10 µg of total RNA were treated with 1 unit RQ1 DNAse RNAse free (Promega M610A) for 30' at 37° C. and phenol/chloroform extracted. Single-strand cDNA was obtained by polyT primed reverse transcription of 3 µg total RNA with SuperScript II RT (Life Technologies 18064-022).

pGFPOF, pGFPOF+3 and pGFPOF-STOP mRNAs splicing analysis was performed by PCR using the primer pair P9 Vs P10, whereas the primer pair P11 Vs P12 was used for pGFP-BHB and pGFP-BHB+3 analysis.

P9 or P12 primers were P32 labeled. PCR products were electrophoresed on a 6% polyacrylamide, 8M urea 20% formamide gel. The gels were dried and exposed to Phosphorimager for 16 hours and visualized by STORM 860 Phosphorimager (Molecular Dynamics).

Sequencing of RT-PCR Products

Spliced and unspliced amplified cDNAs were eluted from non-dried polyacrylamide denaturing gels and submitted to a new round of PCR. The P9-P10 primer pair was used for products derived from pGFPOF, pGFPOF+3 and pGFPOF-STOP mRNAs. P11-P12 was used for products derived from pGFP-BHB and pGFP-BHB+3. Sequence reactions were performed using a Bigdye sequencing kit (Perkin Elemer-Applied Biosystem) primed with P20 for products derived from the first plasmid group and with P21 for those derived from the second plasmid group. Sequences were analyzed on a ABI Prism 310 gentic analyser (Applied Biosystem).

Immunoblotting Analysis

Cell lysates were obtained with RIPA buffer (20 mM hepes PH 7.5, 1% Triton X-100, 150 mM NaCl, 10 mM EDTA), added with complete reagent (protease inhibitor cocktail tablets, Roche cat. 1697-498) and then subjected to SDS-PAGE (15%). Proteins were transferred to a PVDF membrane (immobilon P, Millipore). Membranes were blocked with 5% low-fat milk in TBST and incubated first with mouse anti- FLAG M2 monoclonal antibody (SIGMA F-3165) in Tris Buffered Saline (10 mM tris-Cl at pH 7.5, 150 mM NaCl) containing 0.05% Tween20 and then with HRP-conjugated goat anti-mouse IgG-1(γ) (Caltag M32007). Immunoreactive bands were detected by ECL (Supersignal West Pico Chemiluminescent Substrate, Pierce).

Immunofluorescence

Detection of *Methanococcus jannaschii* tRNA Endonuclease.

Twenty-four hours after plasmid transfection, cells were fixed with 2% paraformaldehyde/0.1% Triton X100 for 20 minutes, washed three times with PBS/1% BSA and incubated with mouse anti-FLAG M2 monoclonal antibody (SIGMA F-3165) in PBS 1% BSA. Cells were then washed and incubated with FITC-conjugated goat anti-mouse IgG-1 (γ) (Caltag cat. M32101).

Visualization of GFP Protein in Transfected Cells.

Forty-eight hours after transfection, cells were fixed with 2% paraformaldehyde/0.1% Triton X100 for 20 minutes, incubated for 10 minutes with 1 µg/ml Hoechst/PBS 1× solution and washed twice with PBS.

All coverslips were mounted with 80% Glycerol/PBS mounting media. The images were taken by fluorescence microscopy (Olympus AX 70) with a Nikon digital camera (Coolpix 990) and processed with Adobe Photoshop version 5.0.

Examples 4-6

This invention also relates to a method for recombining a target RNA molecule that is in the bulge-helix-bulge (BHB) conformation with an exogenous, or targeting, RNA molecule. As described above, the target RNA molecule has been shown to be cleaved within the bulge-helix-bulge. When the cleaved target RNA molecule and the exogenous RNA molecule are exposed to an appropriate ligase, RNA chimeras form, recombining the target RNA molecule and the exogenous RNA molecule across the bulge-helix-bulge. The method of the present invention can be used for recombining RNA molecules can be used for altering RNA function, in that the recombination may be used to destroy RNA function, modify RNA, or even restore RNA function.

Laboratory applications of the present invention include, but are not limited to, tagging proteins and conditional production of RNA hairpins. Clinical applications of the present invention include, but are not limited to, mechanisms for correcting mutations and antiviral therapies.

By expressing an archaeal tRNA endonuclease (the *Methanococcus Jannaschii* endonuclease) in mouse cells, RNAs can be cleaved if they form the BHB (bulge-helix-bulge) structures that are recognized by the enzyme (J. Abelson, et al., *J. Biol. Chem.* 273:12685-8, 1998). The resulting cleavage products are joined together by an endogenous ligase. The utility of this strategy was illustrated with reporter targets EGFP and β-galactosidase mRNAs into which 17-nucleotide introns, flanked by sequences capable of forming BHB structures in cis, were introduced. RNA molecules that can form BHB substrates in trans with targeted mRNAs were also designed. Cotransfection of mouse cells with plasmids expressing these RNAs and the MJ endonuclease led to formation of RNA chimeras in which the target and exogenous RNA were recombined across the BHB. A nonfunctional firefly luciferase mRNA was repaired efficiently by this trans-splicing. This technology is not limited to mRNA, but could in principle be used to destroy, modify or restore the function of a vast repertoire of RNA species or to join selectable tags to target RNAs.

Example 4

In mouse cells, as in other eukaryotic cells, messenger RNA introns are removed by a large ribonucleoprotein assemblage called the spliceosome, using a catalytic mechanism similar to that employed for group II introns. Spliceosomes recognize 5' and 3' splice sites, which are located at exon-intron boundaries. The splicing reaction occurs in two steps. First, the 5' end of the intron is joined to an adenine residue in the branchpoint sequence upstream from the 3' splice site to form a branched intermediate called an intron lariat. In the second step, the exons are ligated and the intron lariat is released (M. J. Moore, et al., The RNA World (Cold Spring Harbor Laboratory Press, New York, 1993). Cis-splicing, converting pre-mRNA to mRNA, is essential for gene expression. An uncommon and less characterized mechanism for RNA processing involves trans-splicing between different pre-mRNA molecules; this process, again catalyzed by the spliceosome, has been demonstrated to form hybrid mRNAs in a number of eukaryotic systems (T. Maniatis and B. Tasic, *Nature* 418:236-243, 2002). The spliceosome places a group of five proteins a few nucleotides proximal to the site where an intron has been cut out and two fragments have been joined. Some of these proteins are stripped away as the RNA exits through the nuclear pore and the remaining proteins can determine the fate of the mRNA. For example, those proteins can trigger NMD (nonsense mediated decay), a proofreading process that results in the specific destabilization of mRNA molecules that contain premature translation termination codons (J. E. Dahlberg, et al., *RNA* 9:1-8, 2003).

Not all mRNA splicing uses a spliceosomal system. A striking example has been described in yeast. HAC1 mRNA, coding for a transcription factor, is spliced by a unique mechanism that does not require the spliceosome (T. N. Gonzalez, et al., *EMBO J.* 18:3119-3132, 1999). The splice junctions of HAC1 pre-mRNA do not conform to the consensus sequences of other yeast pre-mRNAs. The spliceosome is bypassed by a site-specific endoribonuclease that cleaves the precursor specifically at both splice junctions and by the RNA ligase that completes the splicing (C. Sidrauski, et al., *Cell* 87:405413, 1996).

We have engineered a new non-spliceosomal splicing system in mouse cells, utilizing components normally involved in the splicing of archaeal pre-tRNAs. Archaea do not appear to carry the group I introns, group II introns, or nuclear mRNA-type introns that are found in eukaryotes and/or bacteria (J. Abelson, et al., supra, 1998). Instead, they have introns in their tRNA and rRNA genes that are spliced by an apparently archaeal-specific mechanism. All archaeal intron transcripts generate a 'bulge-helix-bulge' motif at the exon-intron junction. The BHB motif consists of two 3-nucleotide bulges on opposite strands of an RNA, separated by a helix of 4 bp (FIG. 11A). An enzyme, the splicing endonuclease, cleaves at symmetrical positions within each of the 3-nt bulges present on the same minor groove face of the central 4-bp helix of the BHB motif, resulting in 2',3'-cyclic phosphate and 5'-OH ends. (J. Abelson, et al., supra, 1998; L. D. Thompson and C. J. Daniels, *J. Biol. Chem.* 265:18104-18111, 1990; J. Lykke-Andersen and R. A. Garrett, *J. Mol. Biol.* 243:846-855, 1994; J. L. Diener and P. B. Moore, *Mol. Cell.* 1:883-894, 1998)

Mutational analyses, secondary structure probing, and sequence analyses have shown that the conformation of the BHB motif is much more important for archaeal endonuclease/RNA recognition than its sequence (J. L. Diener and P. B. Moore, supra, 1998). The addition of one base pair to the central helix results in the loss of accurate endonucleolytic cleavage. The structure of the BHB motif has been determined by NMR spectroscopy. The conformations of the two 3-nt bulges are stabilized by stacking interactions between bulge nucleotides and bases in the adjacent Watson-Crick helices and also by a network of backbone hydrogen bonds. Both bulges are presented on the same minor groove face of the central 4-bp helix, and the overall structure has approximate two-fold symmetry (J. L. Diener and P. B. Moore, supra, 1998), which makes it well-suited for attack by archaeal splicing endonucleases, which are essentially symmetric dimers that can cleave non-tRNA substrates, for example pre-mRNAs, provided they have a BHB.

We chose to express the archeon *Methanococcus jannaschii* tRNA endonuclease in mouse cells. The *M. jannaschii* enzyme is a homotetramer; the monomer is small, consisting of only 179 amino acids. The crystal structure is known and His-125, Tyr-115 and Lys-156 represent the catalytic triad responsible for the cleavage reactions (H. Li, et al., *Science* 280:279-284, 1998). An endogenous mouse ligase ligates the fragments produced by the archaeal endonuclease. We demonstrate both cis and trans non-spliceosomal splicing in mouse cells, catalyzed by the MJ endonuclease. A single pre-mRNA molecule can be subjected to both spliceosomal and non-spliceosomal splicing.

We produced four constructs containing sequences coding for the endonuclease: pMJ, pMUT-MJ, pOPTI-MJ and pOPTI-MUT-MJ. The first, pMJ was obtained by cloning the archaeal endonuclease gene in a mammalian expression vector under the control of the CMV (cytomegalovirus) immediate early promoter. A sequence coding for the FLAG epitope was inserted in order to obtain expression of the epitope at the N terminal of the protein. The second, pMUT-MJ, was derived directly from pMJ by introducing, via PCR, three amino acid changes at positions 125 (H to F), 156 (K to P) and 157 (K to Q). The substitutions, two of which concern the catalytic triad (J. Abelson, et al., supra, 1998), produce an inactive enzyme. The third construct, pOPTI-MJ, permits high expression of the enzyme and codes for a protein identical to that expressed by pMJ. The coding sequence was changed, taking into account the murine codon usage. The fourth construct, pOPTI-MUT-MJ, was derived from pOPTI-MJ by introducing the three amino acid changes described above. We used anti-FLAG antibodies to perform immunofluorescence analysis of NIH3T3 cells, transfected with pMJ, pMUT-MJ, pOPTI-MJ and pOPTI-MUT-MJ. Western blotting showed that all four constructs code for a protein of the correct size (data not shown).

Three different sets of constructs, coding for target RNAs, were produced. The first set includes pGFP-BHB and pGFP-BHB+3. These plasmids code for target RNAs presenting the BHB in the 3' untranslated region (FIG. 11B). pGFP-BHB+3 codes for transcripts characterized by a BHB that presents an expanded helix resulting from the insertion of three base pairs. The altered BHB cannot be cleaved by the endonuclease (J. Abelson, et al., supra, 1998).

The second set includes pGFPof (out of frame), pGFPof+3 and pGFPof-stop. All three code for N-terminal FLAG-EGFP, characterized by the absence of the original ATG at the beginning of the EGFP and by the presence of a new ATG and a Kozak sequence (M. Kozak, *Nucleic Acids Res.* 15:8125-8148, 1987) preceding the sequence coding for the FLAG. In pGFPof, a sequence capable of forming a BHB in the transcript has been inserted between the sequence coding for the FLAG and that coding for the EGFP. As a result of the insertion, the EGFP sequence is out of frame relative to the FLAG sequence. Precise excision of the 17-base intron and subsequent ligation of the halves reconstitutes the correct reading frame.

pGFPof+3 codes for transcripts characterized by a BHB, that, like the one encoded by pGFP-BHB+3, presents an expanded helix resulting from the insertion of three base pairs. The altered BHB cannot be cleaved by the endonuclease. The transcript coded by pGFPof-stop is characterized by an intron containing three stop codons (FIG. 11A), that should block any translation initiating at non-AUG codons eventually induced by the presence of a secondary structure, in this case that of the BHB, just downstream from the alternative initiator codon (M. Kozak, *Proc. Natl. Acad. Sci. USA* 87:8301-8305, 1990).

In order to validate results obtained with the GFP constructs by an independent assay, we created a third type of plasmid coding for target RNA, pBetaGALof. This plasmid codes for a β-galactosidase gene that is out of frame relative to its ATG because it contains a BHB structure as previously described for pGFPof. A spliceosomal intron is also present in the 5' untranslated region of pBeta-GALof mRNA (FIG. 11B).

Our strategy is based on the expectation that the MJ enzyme would cleave the BHB twice and remove the intron sequence, leaving behind two half-molecules. The 5' half-molecule bears a 2'-3'-cyclic phosphate terminus, and the 3' half-molecule bears a 5' hydroxyl terminus (J. Abelson, et al., supra, 1998). Two RNA ligase activities, that could ligate these two half-molecules, have been biochemically identified in mammalian cells. The two RNA ligase activities are mechanistically different. The first activity uses the phosphate from the 2'3'-cyclic phosphodiester to form the 3'-5' phosphodiester linkage at the ligation junction (W. Filipowicz, et al., *Nucleic Acids Res.* 11:1405-1418, 1983; K. K. Perkins, et al., *Proc. Natl. Acad. Sci. USA* 82:684-688, 1985). Although it has been shown to ligate polyribonucleotides in vitro, very little is known about this activity in vivo and, for instance, whether it is able to join non-tRNA substrates. The second mammalian RNA ligase activity incorporates an exogenous phosphate (obtained from a nucleoside triphosphate) at the junction and creates a 2' phosphomonoester, 3'-5' phosphodiester linkage intermediate. A separate 2' phosphatase activity later removes the 2' phosphate moiety. The second mammalian ligase activity is functionally analogous to the only RNA ligase described in yeast (E. M. Phizicky, et al., *J. Biol. Chem.* 261:2978-2986, 1986). The yeast tRNA ligase can ligate substrates other than tRNAs, and has been shown to ligate the HAC1 mRNA, as mentioned above (C. Sidrauski, et al., supra, 1996; J. S. Cox and P. Walter, *Cell* 87:391-404, 1996). Both mammalian RNA ligase activities remain candidates for participation in the ligation of non-tRNA substrates in mouse cells.

Figure 11:
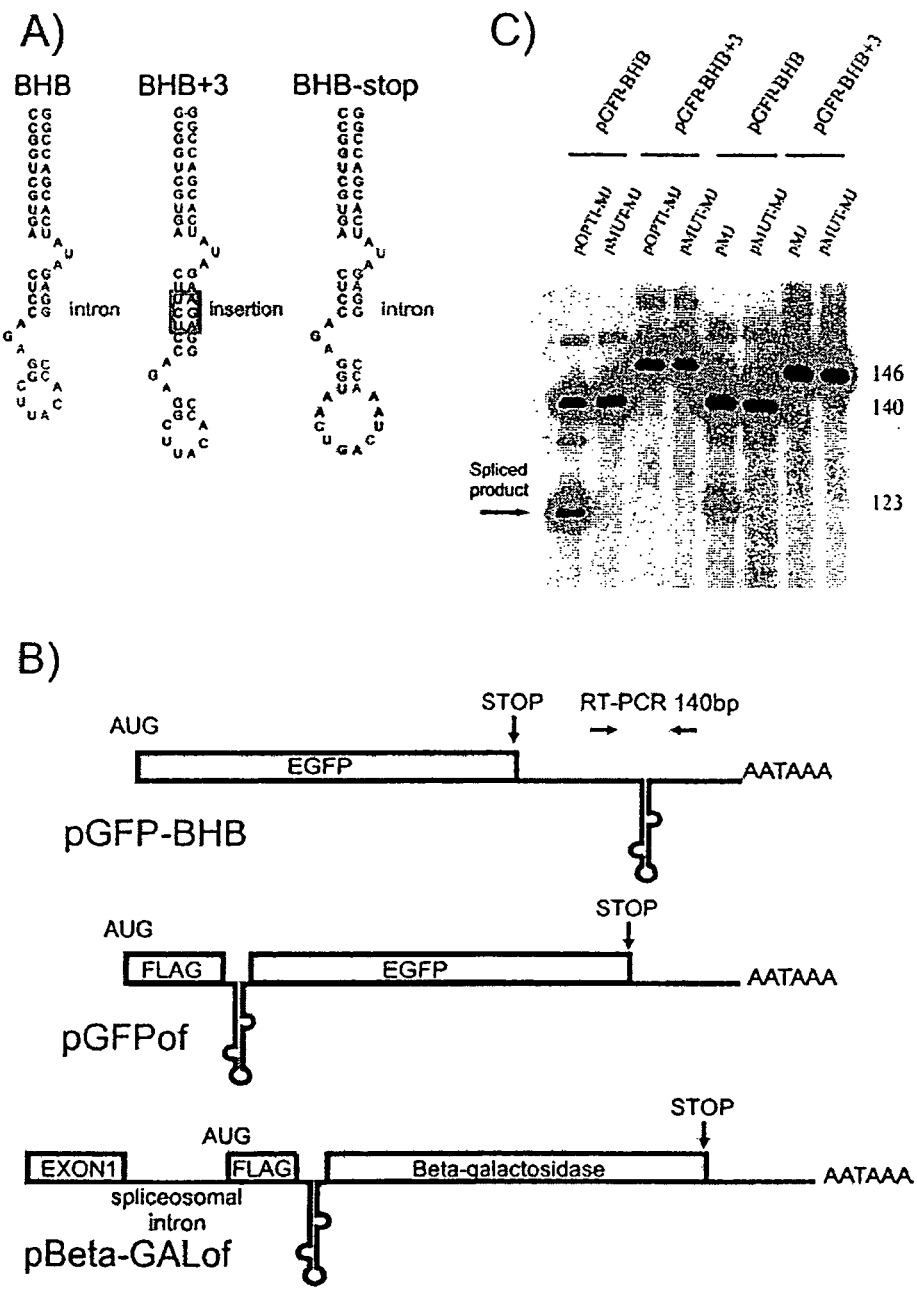
FIG. 11 is a scheme of BHB insertions in reporter mRNAs: (A) the different BHB substrates are detailed. The BHB (provided as SEQ ID NO:73 in the sequence listing) is processed by the MJ endoribonuclease whereas the BHB+3 (provided as SEQ ID NO:75 in the sequence listing) is not. The BHB-stop structure (provided as SEQ ID NO:74 in the sequence listing) contains an intron in which three stop codons, blocking all reading frames, are inserted. (B) structures of the GFP-BHB, GFP of and BetaGAL of genes, showing the positions of the BHB and the RT-PCR primers used for the experiments shown in (C). (C) splicing analysis of mRNAs derived from NIH3T3 cells transfected with plasmids coding for MJ endonuclease and pGFP-BHB or pGFP-BHB+3 target constructs. The figure shows RT-PCR analysis of different GFP mRNAs in the presence or absence of a functional MJ enzyme.

The efficiency and specificity of BHB-mediated splicing was estimated by competitive reverse transcription PCR. RNAs were obtained from NIH3T3 cells cotransfected with plasmids coding for reporter genes and plasmids coding for the endonuclease. The precursor and the spliced product were simultaneously amplified in a single PCR reaction. FIG. 11 shows that when NIH3T3 cells are transiently cotransfected with plasmids expressing pGFP-BHB and plasmids expressing *Methanococcus jannaschii* endonuclease (pOPTI-MJ or pMJ), an RT-PCR product derived from spliced mRNA appears. In contrast, no spliced EGFP RNA is produced in cells cotransfected with plasmids encoding the inactive enzyme (pMUT-MJ) or inactive substrate (pGFP-BHB+3). Splicing efficiency, assessed by a Phosphorimager, increases 10-fold when pOPTI-MJ is used instead of pMJ (FIG. 11C).

Figure 12:
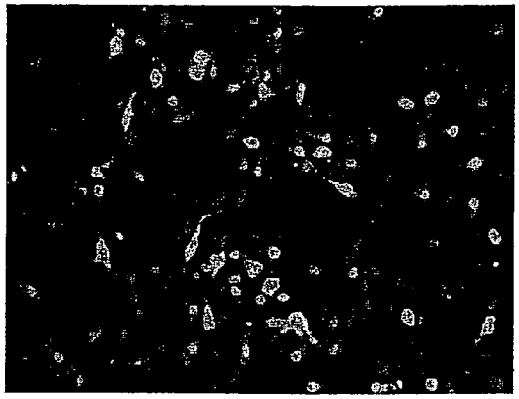
FIG. 12 demonstrates direct GFP fluorescence of transiently transfected NIH3T3 mouse fibroblasts: (A) fluorescence of wt-EGFP, (B) fluorescence of GFPof in presence of the MJ endonuclease, (C) fluorescence of GFPof in presence of the optimized MJ endonuclease, (D) no fluorescence of GFPof is detectable in presence of the inactive endonuclease (MUT-MJ).
Figure 12:
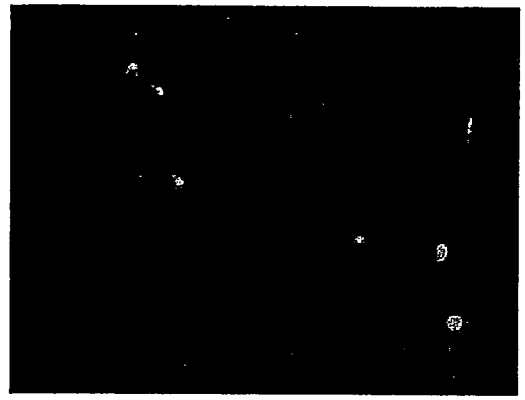
Figure 12:
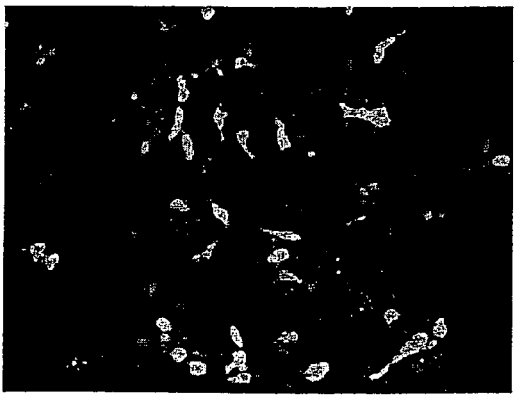
Figure 12:

FIG. 12 shows that when NIH3T3 cells are transiently cotransfected with a plasmid expressing GFPof and a plasmid expressing the *M. jannaschii* endonuclease, EGFP is produced. When a plasmid expressing an inactive endonuclease (pMUT-MJ) is used, EGFP is not produced. These results demonstrate that the *M. jannaschii* endonuclease can excise the intron and that an endogenous ligase activity can produce a spliced mRNA that is correctly translated. Fluorescence analysis substantiates a significant increase in the splicing efficiency when pOPTI-MJ is used instead of pMJ.

To detect β-galactosidase expression via BHB-mediated splicing, NIH3T3 cells were cotransfected with both pBeta-GALof (FIG. 11) and pOPTI-MJ. The β-galactosidase activity does not differ significantly in cells cotransfected with the mutant enzyme (pMUT-MJ) or the control vector without an insert. In contrast, there was a 4- to 5-fold increase in β-galactosidase activity when the cells were cotransfected with pOPTI-MJ. A control experiment was carried out using a pCMV-β (a plasmid coding for the WT β-gal) instead of pBeta-GALof (G. R. MacGregor and C. T. Caskey, *Nucleic Acids Res.* 17:2365, 1989). WT β-galactosidase activity in cells cotransfected with pOPTI-MJ does not differ significantly from that in cells cotransfected with the mutant enzyme (pMUT-MJ) or with the empty vector (data not shown). These experiments confirm that a functional protein can be generated by BHB-mediated mRNA splicing. Since pBeta-GALof also contains a spliceosomal intron, we conclude that both spliceosomal and non-spliceosomal splicing can occur on the same RNA molecule.

Figure 13:
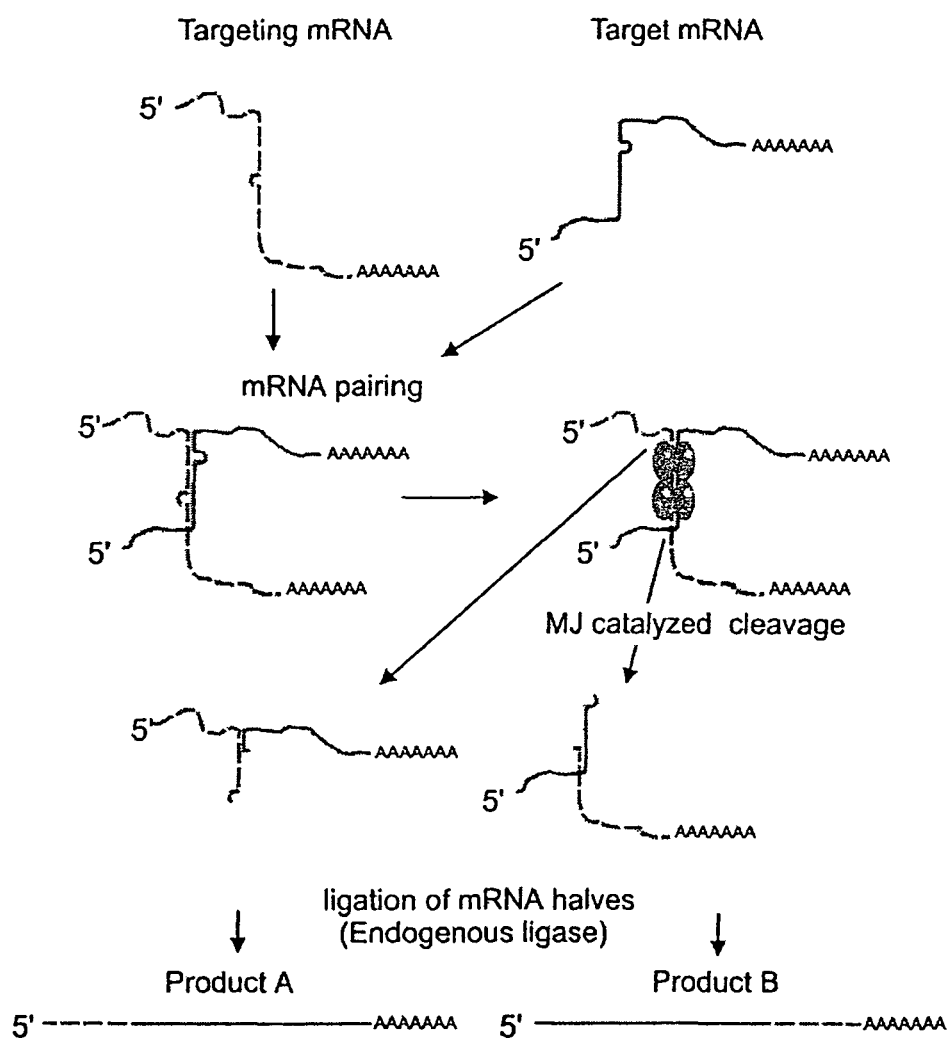
FIG. 13 is a general scheme for BHB-mediated trans-splicing.
Figure 14:
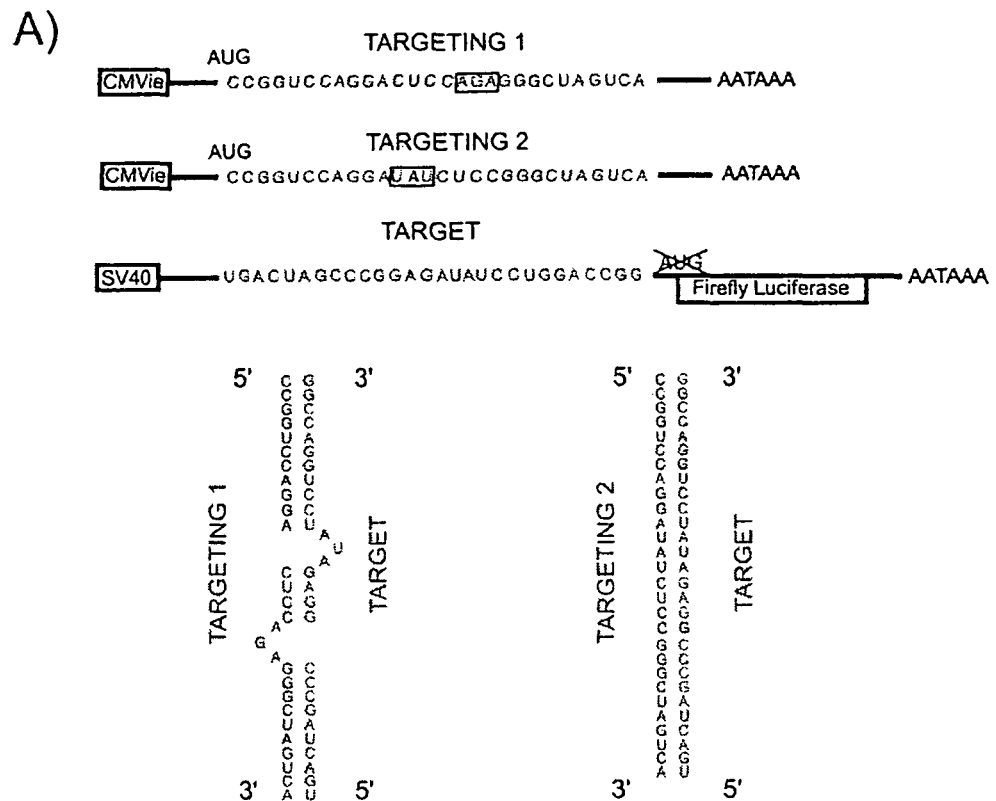
FIG. 14 demonstrates that a defective firefly luciferase mRNA is repaired by BHB-mediated trans-splicing: (A) Targeting and target RNAs. Target RNA (provided as SEQ ID NO:84 in the sequence listing) produces, with Targeting 1 RNA (provided as SEQ ID NO:82 in the sequence listing), a bona fide BHB, with Targeting 2 RNA (provided as SEQ ID NO:83 in the sequence listing) a classical double-stranded RNA. Targeting 1 and Targeting 2 RNAs differ by a total of six nucleotides (in boxes). Both Targeting 1 and Targeting 2 RNAs were transcribed from a CMV immediate early promoter; target RNA was transcribed from a SV40 promoter. (B) RT-PCR analysis shows that both possible recombinant RNAs are generated by the trans-splicing event. (C) Trans-activation of firefly luciferase requires both a bona fide BHB and an optimized MJ endonuclease.
Figure 14:
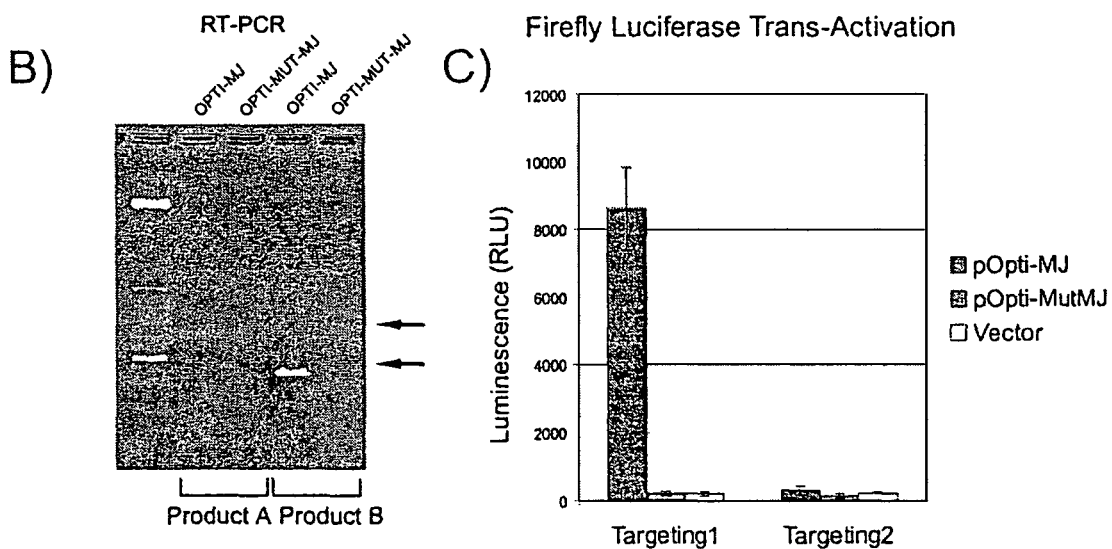

Finally, we designed RNA molecules that can form BHB substrates in trans with targeted mRNAs. A general scheme for a BHB-mediated trans splicing is shown in FIG. 13. This drawing shows the binding of a targeting mRNA, via Watson-Crick base pairing, to a target mRNA followed by MJ endonuclease cleavage and ligation by an endogenous ligase. We used as target a firefly luciferase mRNA characterized by the absence of the original AUG, and a targeting mRNA containing a functional 5' UTR followed by a conventional start codon (FIG. 14A). Cotransfection of NIH3T3 cells with plasmids expressing these RNAs and the MJ endonuclease led to formation of RNA chimeras in which the target and the targeting RNA were recombined across the BHB. RT-PCR experiments demonstrate that both possible RNA recombinants were generated by the trans-splicing event (FIG. 14B). FIG. 14C shows that a defective firefly luciferase mRNA can be repaired by trans-splicing. It is essential that the two interacting RNA molecules form a bona fide BHB structure; if a classical double-stranded RNA is formed no trans-splicing occurs (FIGS. 14A and 14C). These experiments indicate that it is possible to reprogram a target pre-mRNA and, in principle, the possibility exists to achieve a therapeutic result such as correction of a mutation.

Spliceosomal trans-splicing implies the interaction of an intron of one pre-mRNA with an intron of a second pre-mRNA, enhancing the recombination of splice sites between two conventional pre-mRNAs (M. Puttaraju, et al., *Nat. Biotechnol.* 17:246-252, 1999). The various players within the spliceosome recognize the trans-splicing sequences in the targeting RNA rather than the corresponding sequences in the target RNA. A much simpler scenario characterizes BHB-mediated trans-splicing. The interaction to form the BHB in trans does not have to be limited to the introns, but can involve practically any region of the target and the players consist of only two proteins, the archaeal endonuclease and the endogenous ligase.

Various approaches are currently being used to elucidate the principles that underlie the construction and function of eukaryotic cells and organisms. Some of these approaches, such as gene targeting (K. R. Thomas and M. R. Capecchi, *Cell* 51:503-512, 1987) or the gene trap technology (E. Medico, et al., *Nat. Biotechnol.* 19:579-582, 2001), operate at the level of the DNA. Others, like the Tet system, regulate gene expression at the level of transcription (U. Baron and H. Bujard, *Methods Enzymol.* 327:401-421, 2000). Yet another approach, such as induced dimerization, works at the protein level (D. M. Spencer, et al. *Curr. Biol.* 6:839-847, 1996). At the level of the DNA, in mouse, the choice strategy uses the Cre/lox P recombination system of bacteriophage PI (H. Gu, et al., *Cell* 73:1155-1164, 1993; H. Gu, et al., *Science* 265: 103-106, 1994). In this procedure a target gene is flanked with recombinase recognition (lox P) sites; coexpression in the same cell of the Cre recombinase results in the deletion of the lox-P flanked gene segment. The emergent strategy that we report here operates at the RNA level. This strategy also uses prokaryotic elements: the tRNA endonuclease/Bulge-Helix-Bulge (BHB) RNA cleavage system of Archaea. In murine cells, the production of functional RNA can be made dependent upon the presence of an archaeal endonuclease activity.

The type of non-spliceosomal splicing described in this paper permits, in principle, conditional (in space and time) activation of inactive mRNA and mobilization of packets of RNA sequences to reprogram messenger RNAs. It can be used, for example, to repair genetically defective transcripts that contain loss-of-function. BHB-dependent cleavage and ligation is not limited to mRNA, but, in principle, could be applied to destroy, modify or restore the formation of regulatory non-coding RNA sequences such as mRNAs (M. Lagos-Quintana, et al. *Curr. Biol.* 12:735-739, 2002), Xist (A. Wutz, et al., *Nat. Genet.* 30:167-174, 2002) and Air RNAs (F. Sleutels, et al., *Nature* 415:810-813, 2002).

Example 5

A. Plasmids Coding for mRNAs Containing the BHB Structure.

GFPof was obtained by amplifying the EGFP gene from the pEGFP-N3 expression vector (Clontech). The EGFP was sequentially amplified with two sets of primers: P1 and P3, P2 and P3.

A new start codon embedded in a Kozak sequence was inserted and the natural EGFP start codon was mutated with the introduction an AgeI site. The modified EGFP (GFPof) was re-inserted into the BglII-NotI sites of the pEGFP-N3 vector (pGFPof).

Plasmids pGFPof+3 and pGFP-Stop were obtained by substitution of the EcoRI-AgeI fragment of pGFPof respectively with the double stranded oligonucleotides consisting of P4 and its complement and P5 and its complement.

Plasmids pGFP-BHB and pGFP-BHB+3 contain the BHB in the 3'UTR. The EGFP gene was amplified using the primer pair P2 and P8 from the pd2EGFP-N1 vector (Clontech) to add a 35-nucleotide long spacer downstream of the stop codon. The P2-P8 PCR product was then submitted to a new round of PCR with the P2 and P6, P2 and P7 primer pairs, in order to add the BHB and BHB+3 structures, at the 3' end of EGFP gene. These PCR products were digested with BglII and NotI and cloned back into the original vector.

To obtain the Beta-GALof construct, a first PCR fragment containing the BHB domain was originated by amplification of pGFPof with oligonucleotides P9 and P47, and a second PCR fragment containing the altered ATG start of P-gal gene was obtained by amplification of pCMV-P (Clontech) with P45 and P46 primer pair.

These two PCR products were mixed, and re-amplified using the oligonucleotides P9 and P46. The resulting fragment was restricted with BglII, blunt-ended by filling-in and then restricted with EarI. This was ligated to the β-galactosidase EarI-NotI restriction fragment, (from pCMV-β), to obtain Beta-GALof. The WT β-galactosidase gene was replaced by cloning the Beta-GALof sequence into the NotI sites of pCMV-β.

B. Plasmids Coding for *Methanococcus jannaschii* tRNA Endonuclease.

The *M. jannaschii* gene with the FLAG epitope at its 5' end was cloned by PCR from the pET11 a bacterial expression vector (Hong Li, et al., *Science* 280:284, 1998, a kind gift of Dr. Christopher Trotta). The MJ-endoribonuclease PCR product was obtained using the primer pairs P 12 and P 13 and cloned in the BglII-NotI sites of the pd2EGFP-N1 backbone.

The plasmid pMUT-MJ was obtained via PCR from pMJ. Three aminoacidic substitutions were introduced: His 125 to Phe, Lys 156 to Pro and Lys 157 to Gln. The *M. jannaschii* gene was amplified using three different primer pairs: P12 and P15, P14 and P17 and P16 and P13. The three PCR products were mixed, re-amplified with P12 and P13 and cloned in the BglII-NotI sites of the pd2EGFP-N1 backbone.

OPTI-MJ template was obtained by assembling ten oligonucleotides (P20-P29). The OPTI-MJ gene was amplified, utilizing the Pfu DNA Polymerase (Stratagene) and the primers P12 and P3, and cloned in the BglII and NotI sites of the pd2EGFP-NI backbone.

The plasmid pOPTI-MUT-MJ was obtained via PCR from pOPTI-MJ. Three aminoacidic substitutions were introduced: His 125 to Phe, Lys 156 to Pro and Lys 157 to Gln. The *M. jannaschii* gene was amplified using three different primer pairs: P12 and P31, P30 and P33, P32 and P3. The three PCR products were mixed, re-amplified with P12 and P3 and cloned in the pd2EGFP-N1 backbone.

C. Plasmids Coding for Target and Targeting RNAs.

The plasmid coding for target RNA (see FIG. 14) was obtained from pGL3 Control Vector (Promega). A sequence corresponding to one half of the BHB was inserted at the Hind III-NarI sites with consequent elimination of the AUG starting codon of the firefly luciferase gene. To synthesize the fragment to be inserted we amplified oligonucleotide P36 utilizing P34 and P35 as primers. The PCR product was digested with HindIII and NarI and cloned in pGL3 Control Vector (Promega).

The plasmid coding for Targeting-1 RNA (see FIG. 14) was obtained from pcDNA3 (Invitrogen) by inserting at the BamHI-XhoI sites a double stranded fragment obtained by annealing P37 and P38 and subsequent digestion with BamHI-XhoI. The insert codes for an AUG, included in a Kozak sequence, followed by half BHB.

The plasmid coding for Targeting-2 RNA (see FIG. 14) was obtained from pcDNA3 (Invitrogen) by inserting at the BamHI-XhoI sites a double stranded fragment obtained by annealing P39 and P40 and subsequent digestion with BamHI-XhoI. The insert codes for an AUG, included in a Kozak sequence, followed by a sequence complementary to the half BHB inserted in the target RNA.

D. Culture Conditions and Cell Transfections.

NIH3T3 fibroblasts were grown in Dulbecco's modified medium (DMEM) supplemented with 10% calf serum in a 37° C. incubator with 5% $CO_2$. Cell transfections were carried out using the Lipofectamine 2000 or Lipofectamine Plus (Gibco-BRL) transfection reagent according to the manufacturer's instructions. Each transfection was performed in a 35 mm dish using 4 μg of total plasmid DNA with Lipofectamine 2000 or 2 μg with Lipofectamine Plus.

E. RNA Preparation and RT-PCR Analysis.

Total RNA was isolated from cells 24 hours after transfection using the Trizol reagent (Life Technologies) following the manufacturers instructions. 10 μg of total RNA were treated with 1 unit of RQ1 DNAse RNAse free (Promega M610A) for 30' at 37° C. and phenol/chloroform extracted. Single stranded cDNA was obtained by poly-dT primed reverse transcription of 3 μg total RNA with SuperScript II RT (Life Technologies 18064-022).

pGFPof, pGFPof+3 and pGFPof-stop mRNAs splicing analysis was performed by PCR using the primer pair P9 and P10, whereas the primer pair P11 and P3 was used for pGFP-BHB and pGFP-BHB+3 analysis.

P9 or P3 primers were P32 labeled. PCR products were electrophoresed on a 6% polyacrylamide, 8M urea, 30% formamide gel. The gels were dried and exposed to Phosphorimager for 16 hours and visualized by STORM 860 Phosphorimager (Molecular Dynamics).

cDNAs derived by trans-spliced mRNAs were submitted to 36 cycles PCR using Accuprime Taq DNA Polymerase System (Invitrogen) with the primer pair P41-P42 and P43-P44, and analyzed by agarose gel electrophoresis.

F. Sequencing of RT-PCR Products.

Spliced and unspliced amplified cDNAs were eluted from non-dried polyacrylamide denaturing gels and submitted to a new round of PCR. The P9-P10 primer pair was used for products derived from pGFPof, pGFPof+3 and pGFPof-stop mRNAs. P11-P3 was used for products derived from pGFP-BHB and pGFP-BHB+3. Sequence reactions were performed using the Bigdye Sequencing Kit (Perkin Elmer-Applied Biosystem) primed with P18 for products derived from the first plasmid group and with P19 for those derived from the second plasmid group. Sequences were analyzed on an ABI Prism 310 genetic analyser (Applied Biosystem).

G. Visualization of EGFP Protein in Transfected Cells.

Forty-eight hours after transfection, cells were fixed with 2% paraformaldehyde/0.1% Triton X100 for 20 minutes, incubated for 10 minutes with lug/ml Hoechst/PBS 1× solution and washed twice with PBS. All coverslips were mounted with 80% Glycerol/PBS mounting media. The images were taken by fluorescence microscopy (Olympus AX 70) with a Nikon digital camera (Coolpix 990) and processed with Adobe Photoshop version 5.0.

H. Beta Galactosidase Assay.

Forty-eight hours after Beta-GALof transfection, the cells were washed with phosphate-buffered saline and harvested in Passive Lysis Buffer (Promega). After two freeze-thaw cycles, the lysates were centrifuged and the supernatants were collected.

β-gal activities were expressed as the ratio of reporter activity (β-galactosidase) to internal control activity (firefly luciferase). The β-galactosidase and luciferase activities were determined with the standard O-nitrophenil-D-galacto-pyranoside method (β-Gal Assay Kit, Invitrogen) and Luciferase Assay System (Promega), respectively.

I. Luciferase Assay.

To evaluate the trans-activation of the firefly luciferase gene, cells were transfected with a mixture of target and targeting plasmids. To normalize luciferase activity, the *Renilla* luciferase expression vector pRL (Promega) was added to the transfection mixture as control reporter.

Forty-eight hours after transfection, the cells were washed with phosphate-buffered saline and harvested in Passive Lysis Buffer (Promega). After two freeze-thaw cycles, the lysates were centrifuged and the supernatants were collected. Luciferase activity was determined using the Dual Luciferase Reporter Assay System (Promega), according to manufacturer's instructions. The instrumentation used was a Lumat LB 9507 luminometer (EG & G Berthold).

Example 6

The tRNA endonuclease of the archeobacterium *Metahnococcus Jannaschii* (MJ), when expressed in an eucaryotic organism, can be used to modulate gene expression at the post-transcriptional level. The endonuclease recognizes and splices RNA molecules when the latter have Bulge-Helix-Bulge (BHB) structures. Since the ends that the endonuclease creates are ligated by an endogenous RNA ligase, it is possible to activate, inactivate and fuse RNA molecules. Here we describe the creation of a line of transgenic mice that expresses the tRNA endonuclease of MJ in a manner that is constitutive in various tissues.

Background

The tRNA endonuclease of *Metahnococcus Jannaschii* expressed in cell cultures recognizes and splices with a high specificity BHB structures that are inserted in a target mRNA, provoking the removal of small introns followed by the junction of RNA termini by an endogenous ligase. This intron-splicing process is independent of the spliceosomes. The endonuclease has the capacity to recognize and cut BHB structures even when the latter are created in trans or, in other words, by two distinct RNA molecules. Since the splicing reaction of a BHB in trans is followed by the joining of the termini to form hybrid RNA molecules, it is possible to construct plasmids that, when transfected in mammalian cells, will express "targeting" RNAs that are capable of forming, by way of a conventional coupling of complementary bases, a Bulge-Helix-Bulge structure in various "target" RNAs. This technology has been tested on cell models, using GFP and Firefly Luciferase as target genes (ref. The BHB-mediated splicing reactions have been evidenced by means of RT-PCR at the messenger RNA level and, in the case of Firefly Luciferase, by measuring gene reporter activity with the specific assay.

In brief, the ability of the MJ tRNA endonuclease to recognize and splice BHB structures in trans allows one to design RNA molecules that, through a trans-splicing reaction, can modify endogenous RNAs without altering the genomic structure of the receiving organism.

Given that this technology, which up to now has been applied to cell cultures, is potentially relevant to the modulation and analysis of genes, and to the correction of genetic defects in mouse models, and given that the creation of such technologies for the modification of specific RNA targets requires the use of animals that express the tRNA endonuclease of MJ, we created transgenic lines in which the gene that codifies for the enzyme had been inserted in the mouse genome.

The sequence that codes for the endonuclease was modified so as to adapt it to the mouse codon usage, and then cloned downstream of a chicken beta actin promoter preceded by the CMV enhancer.

The analysis of the expression levels of a typical transgene has shown that an adequate expression took place.

Though the analysis carried out using RT-PCR has shown that expression occurred in all of the tissues examined (brain, heart, skeletal muscle, lung, kidney and liver), northern blot analysis has revealed appreciable levels of mRNA in the heart, muscle and, to a lesser extent, also in the liver.

Figure 15:
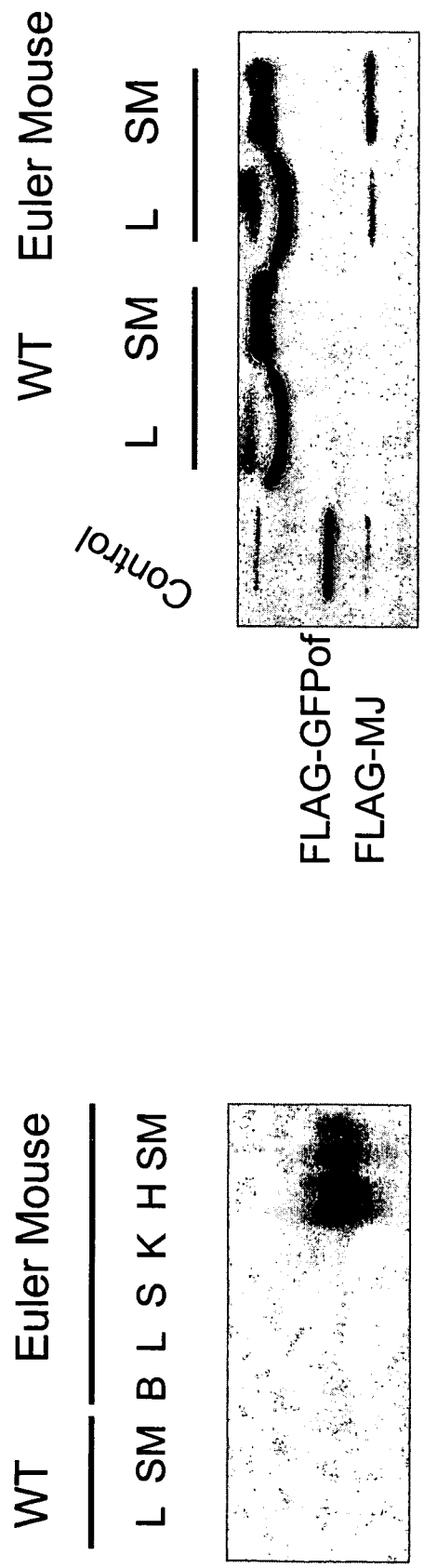
FIGS. 15A and B are demonstrations of the presence of the archaeal endonuclease in various tissues of the transgenic mouse.
FIG. 15B is an immunopurification and western blot analysis.
Figure 16:
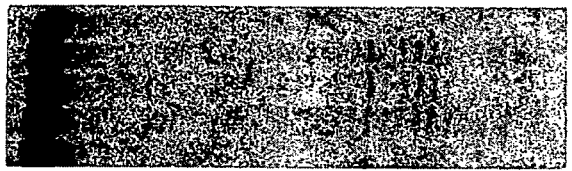
FIG. 16 is a functional analysis of the archaeal tRNA endonuclease obtained from the transgenic mouse (FIG. 16B) and structure and sequence (provided as SEQ ID NO:85 in the sequence listing) of the substrate utilized in the assay (FIG. 16A).
Figure 16:
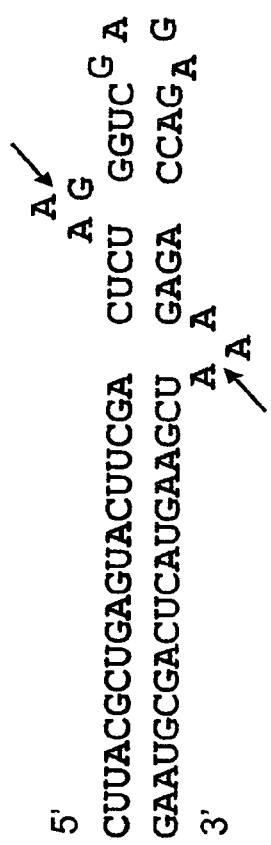
Figure 17:
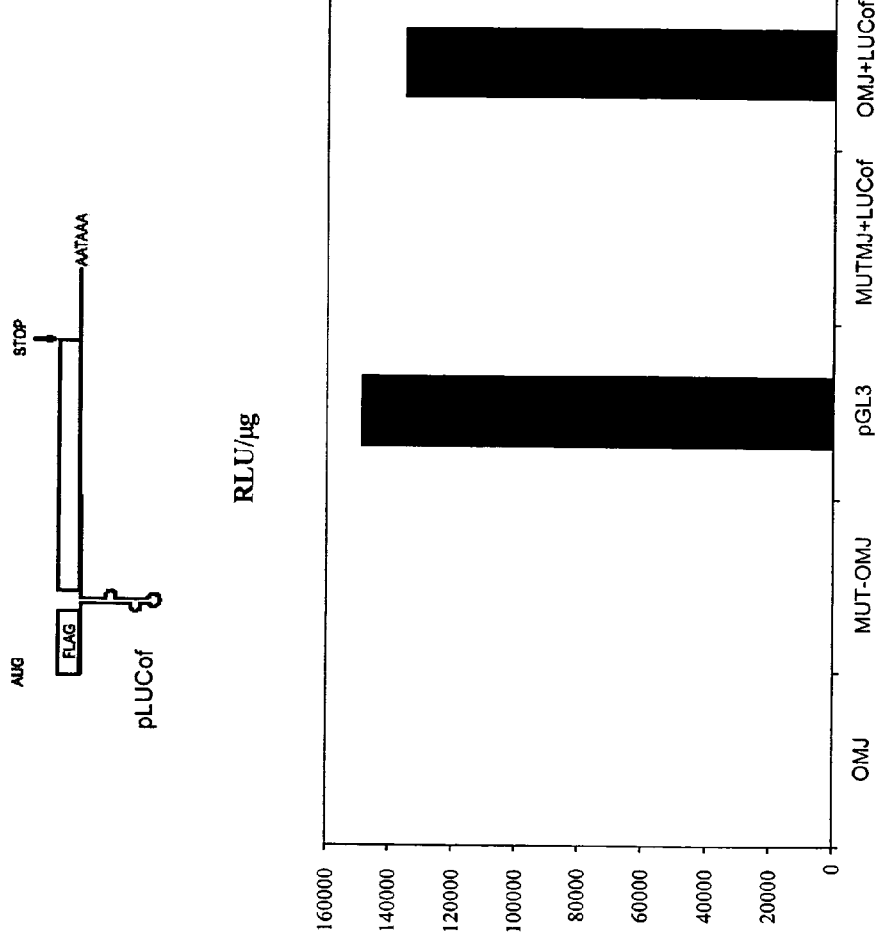
FIG. 17 is a luminescence analysis of hepatic tissue lyates obtained from mice.

The expression of the transgene and the consequent production of the MJ endonuclease was further validated by means of immunoprecipitation and western blotting experiments (FIG. 15). The functionality of the enzyme produced in the tissues of transgenic mice was analyzed by assaying its activity in vitro on RNA substrates that contained BHB structures (FIG. 16). We also observed BHB-mediated splicing following delivery of naked plasmids, via the tail vein, in mice (FIG. 17).

Results and Materials and Methods

Creation of the Construct

Before building the definitive construct, we created an intermediate one in order to endow the *Metahnococcus Jannaschii* tRNA endonuclease's coding sequence with the BGH's polyadenylization tail.

To create that construct we resynthesized the entire coding sequence of the enzyme in accordance with the codon usage of mice. We also inserted the sequence that codes for the FLAG epitope at the enzyme's N-terminal extremity. The enzyme FLAG sequence was obtained from pOPTI-MJ (see patent XX) inserted in PUC18 as a NheI-BamHI fragment (pUC-MJ). Downstream of the MJ coding sequence, we inserted the BGH's polyadenylization tail. The latter was obtained by way of amplification with the BGH1 and BGH2 primers from the pcDNA3 plasmidic vector. The fragment thus produced was digested with the BamHI and XbaI restriction enzymes and cloned in the BamHI and XbaI sites of pUCMJ.

The MJ-BGHpA fusion was then excised by digestion with the BglII enzyme and cloned in the polylinker of the commercial vector pTriEX-1.1 Neo (Novagen) digested with the restriction enzyme BglII. In the construct thus obtained (pTriEX-MJ), the MJ endonuclease is under the control of the chicken beta actin promoter preceded by the human CMVie enhancer.

PTrieX-MJ was linearized with the XhoI enzyme and then injected in mouse oocytes.

```
BGH1 (SEQ ID NO: 21)
5'- ttg acg agt tct tctgaggggatccat tcctag agctcgctg atcagcc-3'

BGH2 (SEQ ID NO: 22)
5'- agg acc tct aga aga tct gcc tgc tat tgt ctt ccc a-3'
```

Injection in the Oocytes

The oocytes were injected with a solution containing the construct linearized with the XhoI enzyme at a concentration of 2-5 ng/µl, transferred in the XX terrain, maintained in culture for xx, and reimplanted in pseudopregnant FVB/N females.

Four transgenic founders were identified by PCR on DNA extracted from the tails (primers MJ1 and MJ2). (The amplified product is 693 bp on genomic DNA).

```
MJ1 (SEQ ID NO: 23)
5'- CTC TGA CTG ACC GCG TTA CTC-3'

MJ2 (SEQ ID NO: 24)
5'-TGC CGT TCT TGT CGA ACA CG-3'
```

Characterization by Means of Southern Blotting

The genomic DNA was extracted from the tail of each founder and results were confirmed using DNA extracted from the brain and liver of transgenic F1 mice (obtained from the re-crossing founder X FVB/N). Extraction was carried out using the salting out method (ref. Miller, S. A., et al., *NAR* 6(3):1215, 1988). The DNA thus obtained was digested with the BglII, NheI and AflI enzymes, electrophoresed and transferred on Hybond N+ (Hamersham). Filters were hybridized with a base probe specific for optimized *Methanococcus Jannaschii* that was obtained by digesting pTrieX-MJ with BglII.

Analysis of Transgene Expression

All transgenes were analyzed for their expression by means of southern blotting. The RNAs were obtained from the liver, heart, skeletal muscle, lung, spleen, brain and kidney. The organs were taken from mice that resulted from the third re-crossing with FVB/N and two mice were analyzed for each transgene.

30 μg of total RNA from each tissue were gel electrophoresed and blotted on Hybond N+ according to the protocol provided by the supplier. The northern blots that were obtained were hybridized with the MJ probe (BglII fragment).

Only mice derived from MJ1224 yielded a positive signal in the lanes corresponding to the heart, skeletal muscle, brain and liver.

The RNAs derived from MJ1224 mice were also analyzed by means of RT-PCR using MJ1 and MJ2 primers. Those primers amplify a 435 bp fragment on cDNA.

RT-PCR analysis showed some expression, albeit a minimal one, also in those tissues that had yielded negative results upon northern blotting testing.

Referring to FIG. 15A, northern blotting analysis of the expression of the archaeal endonuclease in various tissues of the transgenic mouse is demonstrated.

Immunopurification

The tRNA endonuclease of MJ was purified from a homogeneous mixture of heart, skeletal muscle and liver obtained from two transgenic mice (F1) by means of immunopurification on anti-FLAG monoclonal antibodies combined with agarose (Ezview Red ANTI-FLAG M2 Affinity Gel, Sigma).

The homogenous mixture contained 450 mg of liver and the entire heart in a lysis buffer according to the protocol suggested by the producer of the resin. The entire lysate obtained from the transgenic mouse tissue and FVB/N was incubated with 40 μg of resin O/N at 4° C. The enzyme was eluted for competition with the 3× FLAG peptide according to instructions. The entire eluate was utilized for the in vitro assay.

Referring to FIG. 15B, the enzyme is prevalently expressed in the heart and in the skeletal muscle. Immunopurification and western blotting of the archaeal enzyme from liver and skeletal muscle are also demonstrated. The control, immunopurification and western blotting of the archaeal enzyme and of FLAG-GFPof from NIH3T3 cells cotransfected with plasmids coding for the two proteins, is also disclosed.

Functional Assay on BHB Substrates

The tRNA endonuclease of MJ was purified by immunoprecipitation from the heart, muscle and liver.

As a negative control, the same procedure was repeated on FVB/N mice.

As a positive control, a purified and dialyzed recombinant MJ endonuclease produced from the bacterial strain (Trotta) was employed.

The substrate that was used for the enzymatic in vitro assay is represented by a RNA marked by means of in vitro transcription with $\alpha UTP^{32}$, which represents a BHB structure recognized by the enzyme.

The precursor was incubated for 3 hours at 37° C. after addition to the total resin eluate, which corresponded to 100 μl, of 50 μl JB70 buffer ($NH_4Cl$ 70 mM, $MgCl_2$ 7 mM, EDTA 0.1 mM, DTT 2.5 mM, Glycerol 10%) and 30 fmoles of substrate (1 μl).

As a positive control, 2 μl of purified MJ, corresponding to a total of 0.4 μl, were utilized.

At the end of the enzymatic assay, the samples (RNA) were extracted with phenol and precipitated in ethanol utilizing a tRNA carrier. After having been resuspended in RNA MIX buffer (Urea, Sucrose, 0.5% BBF, 0.5% XFF, TBE 10×), the samples were run on a 12% acrylamide 8M urea gel.

The result was analyzed using STORM 860 (Molecular Dynamics).

Results

FIGS. 15, 16 and 17 summarize results obtained from the above-described experiments.

FIG. 16A discloses functional analysis of the archaeal tRNA endonuclease obtained from the transgenic mouse. FIG. 16B shows the structure and sequence of the substrate utilized in the assay.

FIG. 17 illustrates a luminescence analysis of hepatic tissue lysates obtained from mice that were injected in the tail vein. The archaeal enzyme and the endogenous lysate produce a spliced messenger coding for luciferase. Referring to FIG. 17, pOMJ: The mice were injected with a naked plasmid coding for the archaeal endonuclease. pMUT-OMJ: The mice were injected with a naked plasmid coding for the mutant archaeal endonuclease. pGL3: The mice were injected with a naked plasmid coding for wild-type firefly luciferase (Promega). pLUCof, pMUT-OMJ: The mice were co-injected with a naked plasmid coding for LUCof mRNA (this RNA contains an archaeal intron that renders the latter out of frame) and a naked plasmid coding for the mutant enzyme. PLUCof, pOMJ: The mice were co-injected with a naked plasmid coding for LUCof mRNA (excision of the intron and ligation of the exons results in the production of a functional luciferase mRNA) and a naked plasmid coding for the archaeal enzyme. Twenty μg of the indicated naked plasmid were injected in 1, 2, and 3. Twenty μg of plasmid coding for the archaeal enzyme or its mutant version and 20 μg of a plasmid coding for pLUCof were injected in the tail vein of mice in 4 and 5.

TABLE 2

| Oligodeoxyribonucleotides |
| --- |
| P1 5'-GAGCTCAAGCTTCGAATTCCCGGTCGTGACTCCAGAGGCTTACACCGGAGATATCACGACCGGTTGTGAGCAAGGGCGAG-3' (SEQ ID NO: 25) |
| P2 5'-ATCACGAGATCTCCACCATGGACTACAAAGACGATGACGATAAACTCGAGCTCAAGCTTCGAATT-3' (SEQ ID NO: 26) |
| P3 5'-TCGGGATCCTCTACAAATGTGGTATGGCTG-3' (SEQ ID NO: 27) |
| P4 5'-GCTTCGAATTCCCGGTCGTGACTTCTCCAGAGGCTTACACCGGAGAAGATATCACGACCGGTTGTGA-3' (SEQ ID NO: 28) |

TABLE 2-continued

Oligodeoxyribonucleotides

P5 5'-GCTTCGAATTCCCGGTCGTGACTCCAGAGGTAACTGACTAAACCGGAGATATCACGACCGGTTGTGA-3' (SEQ ID NO: 29)

P6 5'-ATAAGAATGCGGCCGCCCGGTCGTGATATCTCCGGTGTAAGCCTCTGGAGTCACGACCGGGACGGG-3' (SEQ ID NO: 30)

(SEQ ID NO: 31)
P7 5'-ATAAGAATGCGGCCGCCCGGTCGTGATATCTTCTCCGGTGTAAGCCTCTGGAGAAGTCACGACCGGGGACGGG-3'

(SEQ ID NO: 32)
P8 5'-TCACGACCGGGGACGGGGGCCCAGACGGAGGGCGAGTCCTTGTAGCGCATCTACACATTGATCCTAGCAGA-3'

P9 5'-CGTCAGATCCGCTAGCGCTAC-3' (SEQ ID NO: 33)

P10 5'-CGTCGCCGTCCAGCTCGACCA-3' (SEQ ID NO: 34)

P11 5'-TAGATGCGCTACAAGGACTCG-3' (SEQ ID NO: 35)

P12 5'-ATCACGAGATCTCCACCATGGACTACAAAGACGATGACGATAAAATGGTGAGAGATAAAATG-3' (SEQ ID NO: 36)

P13 5'-ATAAGAATGCGGCCGCGGATCCTTATGGTTTTACATAGG-3' (SEQ ID NO: 37)

P14 5'-ATAAAGAATTCTCTGTTTATTTGGTTAAGG-3' (SEQ ID NO: 38)

P15 5'-AACAGAGAATTCTTTATCATGTTAGCTCC-3' (SEQ ID NO: 39)

P16 5'-TCAGTTCGGCCGCAATTACTCATAGCAATC-3' (SEQ ID NO: 40)

P17 5'-GTAATTGCGGCCGAACTGAGTGAGCAACC-3' (SEQ ID NO: 41)

P18 5'-GGCACCACCCCGGTGAACAG-3' (SEQ ID NO: 42)

P19 5'-GTATGGCTGATTATGATCTAG-3' (SEQ ID NO: 43)

(SEQ ID NO: 44)
P20 5'-GACTCAGATCTCCACCATGGACTACAAAGACGATGACGATAAAGCCGGCAGAGATAAAATGGGCAAGAAGATCACCGGT-3'

(SEQ ID NO: 45)
P21 5'-GGCGCTCAGCTTGCTGATGCCGTTCTTGTCGAACACGATCACTCTGTCGCCGTCCAGCAGACCGGTGATCTTCTTGCCCAT-3'

(SEQ ID NO: 46)
P22 5'-GGCATCAGCAAGCTGAGCGCCAGGCACTATGGCAATGTGGAAGGCAATTTCCTGAGCCTGAGCCTGGTGGAAGCCCTGTAC-3'

(SEQ ID NO: 47)
P23 5'-TTCGAAGCTCAGGGGCTTGTTGTCCTTATACTTCACCTCCAGCCAGCCCAGGTTGATCAGGTACAGGGCTTCCACCAGGCT-3'

(SEQ ID NO: 48)
P24 5'-AACAAGCCCCTGAGCTTCGAAGAGCTGTATGAATATGCCAGGAACGTGGAGGAAAGACTGTGTCTGAAGTACCTGGTGTAT-3'

(SEQ ID NO: 49)
P25 5'-GAAGTCGGCGCCATACTTCAGGCCGGTCTTCACGATATAGCCCCTGGTCCTCAGGTCCTTATACACCAGGTACTTCAGACA-3'

(SEQ ID NO: 50)
P26 5'-CTGAAGTATGGCGCCGACTTCAGACTGTACGAAAGGGGCGCCAACATCGACAAGGAGCACAGCGTGTATCTGGTGAAGGTG-3'

(SEQ ID NO: 51)
P27 5'-GTGGGCCACTCTCACGAAGCCGGTCAGCTCGCTCAGCAGGAAGCTGCTGTCTTCAGGGAACACCTTCACCAGATACACGCT-3'

(SEQ ID NO: 52)
P28 5'-GGCTTCGTGAGAGTGGCCCACAGCGTGAGAAAGAAGCTGCTGATCGCCATCGTGGACGCCGACGGCGACATCGTGTATTAC-3'

(SEQ ID NO: 53)
P29 5'-CCTCTACAAATGTGGTATGGCTGC-
TACGCGGCCGCGGATCCTTAAGGCTTCACATAGGTCATATTGTAATACACGATGTCGCCG
TC-3'

P30 5'-ATCGACAAGGAGTTCAGCGTGTATCTGGTG-3' (SEQ ID NO: 54)

P31 5'-CAGATACACGCTGAACTCCTTGTCGATGTT-3' (SEQ ID NO: 55)

P32 5'-GCCCACAGCGTGAGACCTCAGCTGCTGATCGCCATC-3' (SEQ ID NO: 56)

TABLE 2-continued

Oligodeoxyribonucleotides

P33 5'-GATGGCGATCAGCAGCTGAGGTCTCACGCTGTGGGC-3' (SEQ ID NO: 57)

P34 5'-TAGGGAAGCTTCGTCAGATCCGCTAGCGC-3' (SEQ ID NO: 58)

P35 5'-AGAATGGCGCCGGGCCTTTCTTTATGTTTTGGCGTC-3' (SEQ ID NO: 59)

(SEQ ID NO: 60)
P36 5'-CGTCAGATCCGCTAGCGCTACCGGACT-
CAGATCAATTCGCTGACTAGCCCGGAGATATCCTGGACCGGTTGAAGACGCCAAAAA
CATAAAG-3'

P37 5'-GATCTGGATCCACCATGGTCCGGTCCAGGACTCCAGAGGGCTAGTCACTCGAGATCTA-3' (SEQ ID NO: 61)

P38 5'-TAGATCTCGAGTGACTAGCCCTCTGGAGTCCTGGACCGGACCATGGTGGATCCAGATC-3' (SEQ ID NO: 62)

P39 5'-GATCTGGATCCACCATGGTCCGGTCCAGGATATCTCCGGGCTAGTCACTCGAGATCTA-3' (SEQ ID NO: 63)

P40 5'-TAGATCTCGAGTGACTAGCCCGGAGATATCCTGGACCGGACCATGGTGGATCCAGATC-3' (SEQ ID NO: 64)

P41 5'-CCCACTGCTTACTGGCTTATCG-3' (SEQ ID NO: 65)

P42 5'-CCCATACTGTTGAGCAATTCACG-3' (SEQ ID NO: 66)

P43 5'-TGAGCTATTCCAGAAGTAGTG-3' (SEQ ID NO: 67)

P44 5'-GGGAGTGGCACCTTCCAGGGTC-3' (SEQ ID NO: 68)

P45 5'-GATATCACGACCGGTTTCGTTTACTTTGACCAACAAGA-3' (SEQ ID NO: 69)

P46 5'-TTCAGGCTGCGCAACTGTTGG-3' (SEQ ID NO: 70)

P47 5'-TCTTGTTGGTCAAAGTAAACGAAACCGGTCGTGATATC-3' (SEQ ID NO: 71)

REFERENCES

Abelson, J., "RNA processing and the intervening sequence problem," *Annu. Rev. Biochem.* 48:1035-1069 (1979).
Abelson, J., Trotta, C. R. and Li, H., "tRNA splicing," *J. Biol. Chem.* 273:12685-12688 (1998).
Baldi, M. I., Mattoccia, E., Ciafrè, S., Gandini-Attardi, D. and Tocchini-Valentini, G. P., "Binding and cleavage of pre-tRNA by the *Xenopus* splicing endonuclease: two separate steps in the intron excision reaction," *Cell* 47:965-971 (1986).
Baldi, M. I., Mattoccia, E., Bufardeci, E., Fabbri, S. and Tocchini-Valentini, G. P., "Participation of the intron in the reaction catalyzed by the *Xenopus* tRNA splicing endonuclease," *Science* 255:1404-1408 (1992).
Baron, U. and Bujard, H., "Tet repressor-based system for regulated gene expression in eukaryotic cells: principles and advances," *Methods Enzymol.* 327:401-421 (2000).
Behlen, L. S., Sampson, J. R., Di Renzo, A. B. and Uhlenbeck, O. C., "Lead-catalyzed cleavage of yeast tRNAPhe mutants," *Biochemistry* 29:2515-2523 (1990).
Bufardeci, E., Fabbri, S., Baldi, M. I., Mattoccia, E. and Tocchini-Valentini, G. P., "In vitro genetic analysis of the structural features of the pre-tRNA required for determination of the 3' splice site in the intron excision reaction," *EMBO J.* 12:4697-4704 (1993).
Carrara, G., Calandra, P., Fuscoloni, P. and Tocchini-Valentini, G. P., "Two helices plus a linker: a small model substrate for eukaryotic Rnase P," *Proc. Natl. Acad. Sci. USA* 92:2627-2631 (1995).
Cox, J. S. and Walter, P., "A novel mechanism for regulating activity of a transcription factor that controls the unfolded protein response," *Cell* 87:391-404 (1996).
Dahlberg, J. E., Lund, E. and Goodwin, E. B., "Nuclear translation: What is the evidence?" *RNA* 9:1-8 (2003).
Deidda, et al., *Nat. Biotechnol.* 12:1499-1504, 2003

Diener, J. L. and Moore, P. B., "Solution structure of a substrate for the archaeal pre-tRNA splicing endonucleases: the bulge-belix-bulge motif," *Mol. Cell.* 1:883-894 (1998).
Filipowicz, W., Konarska, M., Gross, H. J. and Shatkin, A. J., "RNA 3'-terminal phosphate cyclase activity and RNA ligation in HeLa cell extract," *Nucleic Acids Res.* 11:1405-1418 (1983).
Gandini-Attardi, D., Margarit, I. and Tocchini-Valentini, G. P., "Structural alteration in mutant precursors of the yeast tRNALeu3 gene which behave as defective substrates for a highly purified splicing endoribonuclease," *EMBO J.* 4:3289-3297 (1985).
Gandini-Attardi, D., Baldi, M. I., Mattoccia, E. and Tocchini-Valentini, G. P., "Transfer RNA splicing endonuclease from *Xenopus laevis*," *Methods Enzymology* 181:510-517 (1989).
Gonzalez, T. N., Sidrauski, C., Dorfler, S. and Walter, P., "Mechanism of nonspliceosomal mRNA splicing in the unfolded protein response pathway," *EMBO J.* 18:3119-3132 (1999).
Gu, H., Zou, Y. R. and Rajewsky, K., "Independent control of immunoglobulin switch recombination at individual switch regions evidenced through Cre-loxP-mediated gene targeting," *Cell* 73:1155-1164 (1993).
Gu, H., Marth, J. D., Orban, P. C., Mossmann, H. and Rajewsky, K., "Deletion of a DNA polymerase beta gene segment in T cells using cell type-specific gene targeting," *Science* 265:103-106 (1994).
Haselbeck, R. C. and Greer, C. L., "Minimum intron requirements for tRNA splicing and nuclear transport in *Xenopus* oocytes," *Biochemistry* 32:8575-8581 (1993).
Kozak, M. "An analysis of 5'-noncoding sequences from 699 vertebrate messenger RNAs," *Nucleic Acids Res.* 15:8125-8148 (1987).
Kozak, M., "Downstream secondary structure facilitates recognition of initiator codons by eukaryotic ribosomes," *Proc. Natl. Acad. Sci. USA* 87:8301-8305 (1990).

Lagos-Quintana, M., et al., "Identification of tissue-specific microRNAs from mouse," *Curr. Biol.* 12:735-739 (2002).

Li, H., Trotta, C. R. and Abelson, J., "Crystal structure and evolution of a transfer RNA splicing enzyme," *Science* 280:279-284 (1998).

Kierzek, R., "Nonenzymatic hydrolysis of oligoribonucleotides," *Nucleic Acids Res.* 20:5079-5084 (1992).

Kim, S. H., Quickley, G. J., Suddath, F. L., Mc Pherson, A., Sneden, D., Kim, J J., Weinzierl, J. and Rich, A., "Three-dimensional structure of yeast Phenylalanine transfer RNA: folding of the polynucleotide chain," *Science* 179:285-288 (1973).

Kleman-Leyer, K., Arbruster, D. A. and Daniels, C. J., "Characterization of the *Haloferax volcanii* tRNA intron endonuclease gene reveals a relationship between the archaeal and eucaryal tRNA intron processing systems," *Cell* (accompanying paper).

Lee, M. C. and Knapp, G., "Transfer RNA splicing in *Saccharomyces cerevisiae*. Secondary and tertiary structures of the substrates," *J. Biol. Chem.* 260:3108-3115 (1985).

Lykke-Andersen, J. and Garrett, R. A., "Structural characteristics of the stable RNA introns of archaealhyperthermophiles and their splicing junctions," *J. Mol. Biol.* 243:846-855 (1994).

MacGregor, G. R. and Caskey, C. T., "Construction of plasmids that express *E. coli* betagalactosidase in mammalian cells," *Nucleic Acids Res.* 17:2365 (1989).

Maniatis, T. and Tasic, B., Alternative pre-mRNA splicing and proteome expansion in metazoans," *Nature* 418:236-243 (2002).

Mattoccia, E., Baldi, M. I., Gandini-Attardi, D., Ciafrè, S. and Tocchini-Valentini, G. P., "Site selection by the tRNA splicing endonuclease of *Xenopus laevis*," *Cell* 55:731-738 (1988).

Medico, E., Gambarotta, G., Gentile, A., Comoglio, P. M. & Soriano, P., "A gene trap vector system for identifying transcriptionally responsive genes," *Nat. Biotechnol.* 19:579-82 (2001).

Milligan, J. F. and Uhlenbeck, O. C., "Synthesis of small RNAs using T7 polymerase," *Methods Enzymol.* 180:51-62 (1989).

Miao, F. and Abelson, J., "Yeast tRNA-splicing endonuclease cleaves precursor tRNA in a random pathway," *J. Biol. Chem.* 268:672-677 (1993).

Moore, M. J., et al., "The RNA World" (Cold Spring Harbor Laboratory Press, New York, 1993).

Nazarenko, I. A., Harrington, K. M. and Uhlenbeck, O. C., "Many of the conserved nucleotides of tRNA$^{Phe}$ are not essential for ternary complex formation and peptide elongation," *EMBO J.* 13:2464-2471 (1994).

Otsuka, A., De Paolis, A and Tocchini-Valentini, G. P., "Ribonuclease "XIaI", an activity from *Xenopus laevis* oocytes that excises intervening sequences from yeast transfer ribonucleic acid precursors," *Mol. Cell. Biol.* 1:269-280 (1981).

Pan, T. and Uhlenbeck, O. C., "A small metalloribozyme with a two step mechanism," *Nature* 358:560-563 (1992).

Perkins, K. K., Furneaux, H. and Hurwitz, J., "Isolation and characterization of an RNA ligase from HeLa cells," *Proc. Natl. Acad. Sci. USA* 82:684-688 (1985).

Phizicky, E. M., Schwartz, R. C. and Abelson, J., "*Saccharomyces cerevisiae* tRNA ligase. Purification of the protein and isolation of the structural gene," *J. Biol. Chem.* 261:2978-2986 (1986).

Puttaraju, M, Jamison, S. F., Mansfield, S. G., Garcia-Blanco, M. A. and Mitchell, L. G., "Spliceosome-mediated RNA trans-splicing as a tool for gene therapy," *Nat. Biotechnol.* 17:246-252 (1999).

Reyes, V. M. and Abelson, J., "A synthetic substrate for tRNA splicing," *Anal. Biochem.* 166:90-106 (1987).

Reyes, V. M. and Abelson, J., "Substrate recognition and splice site determination in yeast tRNA splicing," *Cell* 55:719-730 (1988).

Sidrauski, C., Cox, J. S., and Walter, P., "tRNA ligase is required for regulated mRNA splicing in the unfolded protein response," *Cell* 87:405-413 (1996).

Sleutels, F., Zwart, R. and Barlow, D. P., "The non-coding Air RNA is required for silencing autosomal imprinted genes," *Nature* 415:810-813 (2002).

Spencer, D. M., et al., "Functional analysis of Fas signaling in vivo using synthetic inducers of dimerization," *Curr. Biol.* 6:839-847 (1996).

Swerdlow, H. and Guthrie, C., "Structure of intron-containing tRNA precursors. Analysis of solution conformation using chemical and enzymatic probes," *J. Biol. Chem.* 259:5197-5207 (1984).

Thompson, L. D. and Daniels, C. J., "Recognition of exon-intron boundaries by the *Halobacterium volcanii* tRNA intron endonuclease," *J. Biol. Chem.* 265:18104-18111 (1990).

Thomas, K. R. and Capecchi, M R., "Site-directed mutagenesis by gene targeting in mouse embryo-derived stem cells," *Cell* 51:503-512 (1987).

Tinoco, I., Jr., Borer, P. N., Dengler, B., Levine, M., Uhlenbeck, O. C., Crothers, D. M. and Gralla, J., "Improved estimation of secondary structure in RNAs," *Nature New Biol.* 246:40-41 (1973).

Trotta, C. R., Miao, F., Arn, E. A., Stevens, S. W., Ho, C. K., Rauhut, R. and Abelson, J. N., "The yeast tRNA splicing endonuclease: a tetrameric enzyme with two active site subunits homologous to the Archeal tRNA splicing endonculeases," Cell (accompanying paper).

Tuerk, C. and Gold, L., "Systematic evolution of ligands by Exponential enrichment: RNA ligands to bacteriophage T4 DNA polymerase," *Science* 249:505-510 (1990).

Westaway, S. K. and Abelson, J., "Splicing of tRNA Precursors. In tRNA: Structure, Biosynthesis, and Function," D. Soll and U. L. RajBhandary, eds (Washington, D.C.: ASM Press), pp. 79-92 (1995).

Wrede, P., Wurst, R., Vournakis, J. and Rich, A., "Conformational changes of yeast tRNA$^{Phe}$ and *E. coli* tRNAGlu as indicated by different nuclease digestion patterns," *J. Biol. Chem.* 254:9608-9616 (1979).

Wutz, A., Rasmussen, T. P. and Jaenisch, R., "Chromosomal silencing and localization are mediated by different domains of Xist RNA," *Nat. Genet.* 30:167-174 (2002).

We claim:

1. A method of cleaving an exogenous non-tRNA target RNA molecule in vitro comprising the steps of:
   (a) providing a first RNA molecule within a mammalian cell, the first RNA molecule being the exogenous non-tRNA target RNA molecule;
   (b) contacting the first RNA molecule with a second RNA molecule, wherein the second RNA molecule comprises a targeting region consisting of:
      (i) a core region that is 7 nucleotides in length, the core region consisting of a 4-nucleotide sequence that is complementary to a 4-nucleotide sequence on the first RNA molecule, and a 3-nucleotide sequence that is directly 3' or 5' to the 4-nucleotide sequence, wherein the 3-nucleotide sequence is not complementary to the 3-nucleotide sequence that is directly 5' or 3' to the complementary 4-nucleotide sequence on the first RNA molecule;
      (ii) a 5' flanking region that is directly 5' to the core region and a 3' flanking region that is directly 3' to the core region, wherein each flanking region consists of a nucleotide sequence that is complementary to a nucleotide sequence on the first RNA molecule that is directly 3' or 5' to the 4-nucleotide sequence of (i), with the proviso that for the flanking region that is on the end of the core region having the 4-nucleotide sequence, the flanking region is complementary to the nucleotide sequence on the first RNA molecule beginning with the fourth nucleotide from the complementary 4-nucleotide sequence,
   whereby the first RNA molecule and the second RNA molecule form an RNA complex comprising a 3-nucleotide unpaired bulge-4-nucleotide paired helix-3-nucleotide unpaired bulge conformation, wherein one bulge has a guanine/adenine dinucleotide and the other bulge has a uracil/adenine dinucleotide; and
   (c) exposing the RNA complex to a heterologous archaeal *Methanococcus jannaschii* tRNA splicing endonuclease, wherein the target RNA molecule is cleaved.

2. The method of claim 1, wherein the first and the second RNA molecules are both mRNA molecules.

3. The method of claim 1 additionally comprising the step of ligating cleavage products from the first RNA molecule and the second RNA molecule, wherein a fusion RNA is formed comprising at least one cleavage product from the first RNA molecule and at least one cleavage product from the second RNA molecule.

4. The method of claim 1 wherein the second RNA molecule is an oligonucleotide of 50-70 nucleotides in length.

5. The method of claim 4 wherein the second RNA molecule comprises at least 20 nucleotides on either side of the core region.

6. The method of claim 1 wherein the 3' and 5' flanking regions of the targeting region of the second RNA molecule are at least 10 nucleotides in length.

* * * * *

UNITED STATES PATENT AND TRADEMARK OFFICE
CERTIFICATE OF CORRECTION

PATENT NO. : 8,512,945 B2  
APPLICATION NO. : 10/821777  
DATED : August 20, 2013  
INVENTOR(S) : Tocchini-Valentini et al.

Page 1 of 1

It is certified that error appears in the above-identified patent and that said Letters Patent is hereby corrected as shown below:

In the specifications

| | |
|---|---|
| Column 3, line 9 | "GFP of" should be -- GFPof -- |
| Column 3, line 25 | "pGFP of" should be -- pGFPof -- |
| Column 3, line 38 | "pGFP of" should be -- pGFPof -- |
| Column 4, line 5 | "GFP of" should be -- GFPof -- |
| Column 4, line 5 | "BetaGAL of" should be -- BetaGALof -- |
| Column 9, line 18 | "pre4RNA" should be -- pre-tRNA -- |
| Column 18, line 45 | "405413" should be -- 405-413 -- |
| Column 22, line 35 | "mRNAs" should be -- miRNAs -- |

Signed and Sealed this  
Twenty-eighth Day of January, 2014

Michelle K. Lee  
*Deputy Director of the United States Patent and Trademark Office*